US011000426B2

(12) United States Patent
Wise et al.

(10) Patent No.: US 11,000,426 B2
(45) Date of Patent: May 11, 2021

(54) DISPOSABLE ABSORBENT ARTICLES HAVING CUFFS OF IMPROVED STRETCH LAMINATE STRUCTURE

(71) Applicant: The Procter & Gamble Company, Cincinnati, OH (US)

(72) Inventors: Brandon Ellis Wise, Cincinnati, OH (US); Gary Dean LaVon, Liberty Township, OH (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 371 days.

(21) Appl. No.: 15/846,349

(22) Filed: Dec. 19, 2017

(65) Prior Publication Data
US 2018/0168891 A1    Jun. 21, 2018

Related U.S. Application Data

(60) Provisional application No. 62/436,589, filed on Dec. 20, 2016, provisional application No. 62/483,965, (Continued)

(51) Int. Cl.
*A61F 13/49* (2006.01)
*A61F 13/15* (2006.01)
(Continued)

(52) U.S. Cl.
CPC .... *A61F 13/4902* (2013.01); *A61F 13/15593* (2013.01); *A61F 13/49061* (2013.01);
(Continued)

(58) Field of Classification Search
CPC .......... A61F 13/15593; A61F 13/51478; A61F 13/51464; A61F 13/49017; A61F 13/4902;
(Continued)

(56) References Cited

U.S. PATENT DOCUMENTS

| 3,113,225 A | 12/1963 | Kleesattel et al. |
| 3,434,189 A | 3/1969 | Buck et al. |

(Continued)

FOREIGN PATENT DOCUMENTS

| CA | 2158790 | 3/1996 |
| CN | 1276196 | 6/1999 |

(Continued)

OTHER PUBLICATIONS

U.S. Appl. No. 15/832,929, filed Dec. 6, 2017, Schneider.
(Continued)

*Primary Examiner* — Susan S Su
(74) *Attorney, Agent, or Firm* — Charles R. Matson; William E. Gallagher

(57) ABSTRACT

An absorbent article having longitudinal cuffs of improved structure is disclosed. The improved cuffs may be elasticized by a plurality of elastic strands that are substantially greater in number, closer in spacing, lower in pre-strain, and lower in decitex, or any combination of these, as compared with those in conventional articles. This combination of features results in ruffles or gathers of cuff material joined to the elastic strands that are substantially greater in machine-direction frequency and substantially lesser in z-direction amplitude, than those in conventional articles. As a result, the cuff structure lies more closely and evenly against the wearer's skin, has an improved, more cloth-like appearance, provides improved gasketing, and provides improved wearer comfort, as compared with cuff structures in conventional articles. A method for manufacturing articles with such cuff structures, utilizing a warp beam as a supply mechanism, is also disclosed.

33 Claims, 32 Drawing Sheets

Related U.S. Application Data filed on Apr. 11, 2017, provisional application No. 62/553,149, filed on Sep. 1, 2017, provisional application No. 62/553,171, filed on Sep. 1, 2017, provisional application No. 62/553,538, filed on Sep. 1, 2017, provisional application No. 62/581,278, filed on Nov. 3, 2017.

(51) Int. Cl.

| | | |
|---|---|---|
| B32B 27/12 | (2006.01) | |
| D01F 6/04 | (2006.01) | |
| D01D 5/08 | (2006.01) | |
| B29C 65/08 | (2006.01) | |
| B29C 65/48 | (2006.01) | |
| B29L 31/48 | (2006.01) | |
| B05C 1/08 | (2006.01) | |
| B32B 37/14 | (2006.01) | |
| B65H 39/16 | (2006.01) | |
| B65H 51/30 | (2006.01) | |
| B29C 65/00 | (2006.01) | |
| B29C 65/74 | (2006.01) | |
| B29K 701/12 | (2006.01) | |
| A61F 13/53 | (2006.01) | |
| A61F 13/64 | (2006.01) | |
| A61F 13/84 | (2006.01) | |
| B32B 5/04 | (2006.01) | |
| B32B 37/00 | (2006.01) | |
| B32B 37/12 | (2006.01) | |
| D04H 3/12 | (2006.01) | |
| A61F 13/56 | (2006.01) | |
| B32B 37/22 | (2006.01) | |
| A61F 13/513 | (2006.01) | |

(52) U.S. Cl.
CPC ... *A61F 13/15601* (2013.01); *A61F 13/15699* (2013.01); *A61F 13/15739* (2013.01); *A61F 13/15764* (2013.01); *A61F 13/49012* (2013.01); *A61F 13/49015* (2013.01); *A61F 13/49017* (2013.01); *A61F 13/49019* (2013.01); *A61F 13/53* (2013.01); *A61F 13/5622* (2013.01); *A61F 13/64* (2013.01); *A61F 2013/1591* (2013.01); *A61F 2013/15292* (2013.01); *A61F 2013/15373* (2013.01); *A61F 2013/15406* (2013.01); *A61F 2013/15447* (2013.01); *A61F 2013/15552* (2013.01); *A61F 2013/15869* (2013.01); *A61F 2013/15918* (2013.01); *A61F 2013/15959* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 2013/530343* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/01* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *C08J 2300/26* (2013.01); *D01D 5/08* (2013.01); *D01F 6/04* (2013.01); *D04H 3/12* (2013.01)

(58) Field of Classification Search
CPC .......... A61F 13/49014; A61F 13/49015; A61F 13/49012; A61F 13/49019; A61F 2013/15447; A61F 2013/15373; A61F 2013/15292; A61F 13/15699; B32B 37/22; B32B 5/022; D04H 3/12; B29C 66/344

See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long et al. |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa et al. |
| 4,525,905 A | 7/1985 | Bogucki-Land |
| 4,610,678 A | 9/1986 | Weisman et al. |
| 4,640,859 A | 2/1987 | Hansen et al. |
| 4,657,539 A | 4/1987 | Hasse |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,776,911 A | 10/1988 | Uda et al. |
| 4,795,454 A * | 1/1989 | Dragoo ............... A61F 13/4942 604/385.28 |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,984,584 A | 1/1991 | Hansen et al. |
| 5,003,676 A | 4/1991 | McFalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |
| 5,334,289 A | 8/1994 | Trokhan et al. |
| 5,342,341 A | 8/1994 | Igaue et al. |
| 5,360,420 A | 11/1994 | Cook et al. |
| 5,393,360 A | 2/1995 | Bridges et al. |
| 5,413,849 A | 5/1995 | Austin et al. |
| 5,514,523 A | 5/1996 | Trokhan et al. |
| 5,531,729 A | 7/1996 | Coles et al. |
| 5,558,658 A | 9/1996 | Menard et al. |
| 5,562,646 A | 10/1996 | Goldman et al. |
| 5,569,234 A | 10/1996 | Buell et al. |
| 5,575,874 A | 11/1996 | Griesbach, III et al. |
| 5,599,335 A | 2/1997 | Goldman et al. |
| 5,599,420 A | 2/1997 | Yeo et al. |
| 5,628,097 A | 5/1997 | Benson et al. |
| 5,643,588 A | 7/1997 | Roe et al. |
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |
| 5,775,380 A | 7/1998 | Roelstraete et al. |
| 5,827,259 A * | 10/1998 | Laux ................ A61F 13/49011 604/385.29 |
| 5,858,504 A | 1/1999 | Steven |
| 5,887,322 A | 3/1999 | Hartzheim et al. |
| 5,895,623 A | 4/1999 | Trokhan et al. |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |

(56) References Cited

U.S. PATENT DOCUMENTS

| | | |
|---|---|---|
| 5,993,433 A | 11/1999 | St. Louis et al. |
| 5,997,521 A | 12/1999 | Robles et al. |
| 6,036,796 A | 3/2000 | Halbert et al. |
| 6,043,168 A | 3/2000 | Colman et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,139,941 A | 10/2000 | Jankevics et al. |
| 6,153,209 A | 11/2000 | Vega et al. |
| 6,248,195 B1 | 6/2001 | Schmitz |
| 6,248,197 B1 | 6/2001 | Nakanishi et al. |
| 6,291,039 B1 | 9/2001 | Combe et al. |
| 6,319,239 B1 | 11/2001 | Daniels et al. |
| 6,383,431 B1 | 5/2002 | Dobrin et al. |
| 6,395,957 B1 | 5/2002 | Chen et al. |
| 6,410,129 B2 | 6/2002 | Zhang et al. |
| 6,426,444 B2 | 7/2002 | Roe et al. |
| 6,475,600 B1 | 11/2002 | Morman et al. |
| 6,478,785 B1 * | 11/2002 | Ashton ............. A61F 13/49011 604/385.01 |
| 6,482,191 B1 | 11/2002 | Roe et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie et al. |
| 6,645,330 B2 | 11/2003 | Pargass et al. |
| 6,673,418 B1 | 1/2004 | DeOlivera et al. |
| 6,676,054 B2 | 1/2004 | Heaney et al. |
| 6,702,798 B2 | 3/2004 | Christoffel et al. |
| 6,790,798 B1 | 9/2004 | Suzuki et al. |
| 6,821,301 B2 | 11/2004 | Azuse et al. |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 * | 10/2006 | Wu ........................... B05C 3/12 604/385.29 |
| 7,465,367 B2 | 12/2008 | Day |
| 7,569,039 B2 | 8/2009 | Matsuda et al. |
| 7,582,348 B2 | 9/2009 | Ando et al. |
| 7,642,398 B2 | 1/2010 | Järpenberg et al. |
| 7,708,849 B2 | 5/2010 | McCabe |
| 7,777,094 B2 | 8/2010 | Mori et al. |
| 7,861,756 B2 | 1/2011 | Jenquin et al. |
| 7,878,447 B2 | 2/2011 | Hartzheim |
| 7,901,393 B2 | 3/2011 | Matsuda et al. |
| 7,905,446 B2 | 3/2011 | Hartzheim |
| 7,954,213 B2 | 6/2011 | Mizutani et al. |
| 8,093,161 B2 | 1/2012 | Bansal et al. |
| 8,143,177 B2 | 3/2012 | Noda et al. |
| 8,186,296 B2 | 5/2012 | Brown et al. |
| 8,226,625 B2 | 7/2012 | Turner et al. |
| 8,308,706 B2 | 11/2012 | Fukae |
| 8,377,554 B2 | 2/2013 | Martin et al. |
| 8,388,594 B2 | 3/2013 | Turner et al. |
| 8,440,043 B1 | 5/2013 | Schneider et al. |
| 8,585,666 B2 | 11/2013 | Weisman et al. |
| 8,647,319 B2 | 2/2014 | Een et al. |
| 8,729,332 B2 | 5/2014 | Takahashi et al. |
| 8,778,127 B2 | 7/2014 | Schneider et al. |
| 8,853,108 B2 | 10/2014 | Ahoniemi et al. |
| 8,906,275 B2 | 12/2014 | Davis et al. |
| 8,939,957 B2 | 1/2015 | Raycheck et al. |
| 9,005,392 B2 | 4/2015 | Schneider et al. |
| 9,039,855 B2 | 5/2015 | Schneider et al. |
| 9,050,213 B2 | 6/2015 | LaVon et al. |
| 9,156,648 B2 | 10/2015 | Yamamoto |
| 9,168,182 B2 | 10/2015 | Hargett et al. |
| 9,198,804 B2 | 12/2015 | Nakamura et al. |
| 9,226,861 B2 | 1/2016 | LaVon et al. |
| 9,248,054 B2 | 2/2016 | Brown et al. |
| 9,265,672 B2 | 2/2016 | Brown et al. |
| 9,295,590 B2 | 3/2016 | Brown et al. |
| 9,370,775 B2 | 6/2016 | Harvey et al. |
| 9,440,043 B2 | 9/2016 | Schneider et al. |
| 9,453,303 B2 | 9/2016 | Aberg et al. |
| 9,539,735 B2 | 1/2017 | Ferguson et al. |
| 9,732,454 B2 | 8/2017 | Davis et al. |
| 9,758,339 B2 | 9/2017 | Yanez, Jr. et al. |
| 9,795,520 B2 | 10/2017 | Kaneko et al. |
| 9,877,876 B2 | 1/2018 | Huang et al. |
| 1,019,024 A1 | 1/2019 | Ashraf et al. |
| 1,059,604 A1 | 3/2020 | Koshijima et al. |
| 1,079,219 A1 | 10/2020 | Hohm et al. |
| 2001/0030014 A1 | 10/2001 | Kwok |
| 2002/0026660 A1 | 3/2002 | Goda |
| 2002/0046802 A1 | 4/2002 | Tachibana et al. |
| 2002/0072723 A1 | 6/2002 | Ronn et al. |
| 2002/0099347 A1 | 7/2002 | Chen et al. |
| 2002/0103469 A1 | 8/2002 | Chen et al. |
| 2002/0134067 A1 | 9/2002 | Heaney et al. |
| 2002/0153271 A1 | 10/2002 | McManus et al. |
| 2002/0177829 A1 | 11/2002 | Fell et al. |
| 2003/0044585 A1 | 3/2003 | Taylor et al. |
| 2003/0070780 A1 | 4/2003 | Chen et al. |
| 2003/0087056 A1 | 5/2003 | Ducker et al. |
| 2003/0093045 A1 | 5/2003 | Jensen |
| 2003/0119404 A1 | 6/2003 | Belau et al. |
| 2003/0125687 A1 | 7/2003 | Gubernick et al. |
| 2003/0144643 A1 | 7/2003 | Järpenberg et al. |
| 2003/0203162 A1 | 10/2003 | Christopher et al. |
| 2003/0233082 A1 | 12/2003 | Kline et al. |
| 2004/0006323 A1 * | 1/2004 | Hall ................ A61F 13/15593 604/385.24 |
| 2004/0030317 A1 | 2/2004 | Torigoshi |
| 2004/0059309 A1 | 3/2004 | Nortman |
| 2004/0097895 A1 | 5/2004 | Busam et al. |
| 2004/0127881 A1 | 7/2004 | Stevens et al. |
| 2004/0133180 A1 * | 7/2004 | Mori ................ A61F 13/49019 604/385.25 |
| 2004/0158212 A1 | 8/2004 | Ponomarenko et al. |
| 2004/0158217 A1 | 8/2004 | Wu et al. |
| 2004/0219854 A1 * | 11/2004 | Groitzsch ............. A61F 13/622 442/328 |
| 2004/0230171 A1 | 11/2004 | Ando et al. |
| 2005/0013975 A1 | 1/2005 | Brock et al. |
| 2005/0107764 A1 | 5/2005 | Matsuda et al. |
| 2005/0148971 A1 | 7/2005 | Kuroda et al. |
| 2005/0230037 A1 | 10/2005 | Jenquin et al. |
| 2005/0244640 A1 | 11/2005 | Riswick et al. |
| 2005/0267431 A1 | 12/2005 | Sasaki et al. |
| 2006/0047260 A1 | 3/2006 | Ashton et al. |
| 2006/0069373 A1 | 3/2006 | Schlinz et al. |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0228969 A1 | 10/2006 | Erdman |
| 2006/0270302 A1 | 11/2006 | Ando et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0179466 A1 | 8/2007 | Tremblay et al. |
| 2007/0196650 A1 | 8/2007 | Yamamoto et al. |
| 2008/0134487 A1 | 6/2008 | Hartono |
| 2008/0149292 A1 | 6/2008 | Scherb |
| 2008/0161768 A1 | 7/2008 | Baba et al. |
| 2008/0287897 A1 | 11/2008 | Guzman et al. |
| 2009/0177176 A1 * | 7/2009 | Saito ................ A61F 13/49017 604/385.29 |
| 2009/0204093 A1 | 8/2009 | Vasic et al. |
| 2009/0312730 A1 | 12/2009 | LaVon et al. |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1 | 3/2010 | Hayase et al. |
| 2010/0248575 A1 | 9/2010 | Malz |
| 2010/0307668 A1 | 12/2010 | Lange et al. |

(56) References Cited

U.S. PATENT DOCUMENTS

| | | |
|---|---|---|
| 2011/0092943 A1 | 4/2011 | Bishop et al. |
| 2011/0118689 A1 | 5/2011 | Een et al. |
| 2011/0120897 A1 | 5/2011 | Takahashi |
| 2011/0250378 A1 | 10/2011 | Eaton et al. |
| 2012/0004633 A1 | 1/2012 | Marcelo et al. |
| 2012/0061015 A1 | 3/2012 | Lavon et al. |
| 2012/0061016 A1 | 3/2012 | Lavon et al. |
| 2012/0071852 A1 | 3/2012 | Tsang et al. |
| 2012/0095429 A1 | 4/2012 | Kobayashi et al. |
| 2012/0271267 A1 | 10/2012 | Love et al. |
| 2012/0277713 A1 | 11/2012 | Raycheck et al. |
| 2012/0323206 A1* | 12/2012 | McMorrow ....... A61F 13/49413 604/385.24 |
| 2013/0032656 A1 | 2/2013 | Yamamoto |
| 2013/0072887 A1 | 3/2013 | Lavon et al. |
| 2013/0102982 A1* | 4/2013 | Nakano ............. A61F 13/49019 604/365 |
| 2013/0112584 A1 | 5/2013 | Gaspari et al. |
| 2013/0139960 A1 | 6/2013 | Maruyama et al. |
| 2013/0171421 A1 | 7/2013 | Weisman et al. |
| 2013/0199696 A1 | 8/2013 | Schneider et al. |
| 2013/0199707 A1 | 8/2013 | Schneider |
| 2013/0211356 A1 | 8/2013 | Nishikawa et al. |
| 2013/0211363 A1* | 8/2013 | LaVon ............... A61F 13/49019 604/385.3 |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0306226 A1 | 11/2013 | Zink et al. |
| 2014/0000794 A1 | 1/2014 | Hamilton et al. |
| 2014/0005621 A1* | 1/2014 | Roe ..................... A61F 13/5644 604/365 |
| 2014/0018759 A1 | 1/2014 | Jayasinghe et al. |
| 2014/0041797 A1 | 2/2014 | Schneider |
| 2014/0107605 A1* | 4/2014 | Schroer, Jr. ....... A61F 13/49017 604/385.22 |
| 2014/0127460 A1 | 5/2014 | Xu et al. |
| 2014/0136893 A1 | 5/2014 | Xie et al. |
| 2014/0148773 A1 | 5/2014 | Brown et al. |
| 2014/0234575 A1 | 8/2014 | Mitsuno et al. |
| 2014/0235127 A1 | 8/2014 | DeJesus et al. |
| 2014/0257231 A1 | 9/2014 | Wang et al. |
| 2014/0276517 A1 | 9/2014 | Chester et al. |
| 2014/0288521 A1 | 9/2014 | Wade et al. |
| 2014/0296815 A1 | 10/2014 | Takken et al. |
| 2014/0302286 A1 | 10/2014 | Okuda et al. |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0126956 A1 | 5/2015 | Raycheck et al. |
| 2015/0136893 A1 | 5/2015 | Koskol |
| 2015/0164708 A1* | 6/2015 | Hashimoto ......... A61F 13/4942 604/385.26 |
| 2015/0167207 A1 | 6/2015 | Bongartz et al. |
| 2015/0173967 A1 | 6/2015 | Kreuzer et al. |
| 2015/0230995 A1 | 8/2015 | Kaneko et al. |
| 2015/0245958 A1 | 9/2015 | Chmielewski et al. |
| 2015/0257941 A1 | 9/2015 | Eckstein et al. |
| 2015/0282999 A1 | 10/2015 | Arizti et al. |
| 2015/0320612 A1 | 11/2015 | Seitz et al. |
| 2015/0320613 A1 | 11/2015 | Seitz et al. |
| 2015/0320619 A1 | 11/2015 | Seitz et al. |
| 2015/0320620 A1 | 11/2015 | Seitz et al. |
| 2015/0320622 A1 | 11/2015 | Seitz et al. |
| 2015/0328056 A1* | 11/2015 | Een .................... A61F 13/15699 604/385.3 |
| 2015/0351972 A1 | 12/2015 | Bing-Wo |
| 2016/0015574 A1* | 1/2016 | Okubo ............. A61F 13/49011 604/385.27 |
| 2016/0058624 A1 | 3/2016 | Hohm et al. |
| 2016/0058627 A1 | 3/2016 | Barnes et al. |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0228305 A1 | 8/2016 | Gualtieri et al. |
| 2016/0270977 A1 | 9/2016 | Surushi et al. |
| 2016/0331600 A1 | 11/2016 | Polidori et al. |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0191198 A1 | 7/2017 | Ashraf et al. |
| 2017/0258650 A1 | 9/2017 | Rosati et al. |
| 2017/0319403 A1 | 11/2017 | Bewick-Sonntag et al. |
| 2017/0348163 A1 | 12/2017 | Lakso et al. |
| 2018/0092784 A1 | 4/2018 | Wade et al. |
| 2018/0140473 A1 | 5/2018 | Koshijima et al. |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |
| 2018/0168878 A1 | 6/2018 | Schneider et al. |
| 2018/0168879 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168888 A1* | 6/2018 | Zink .................... A61F 13/512 |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0333311 A1* | 11/2018 | Maki ..................... A61F 13/49 |
| 2019/0003079 A1 | 1/2019 | Ashraf et al. |
| 2019/0003080 A1 | 1/2019 | Ashraf et al. |
| 2019/0070041 A1 | 3/2019 | Schneider et al. |
| 2019/0070042 A1 | 3/2019 | LaVon et al. |
| 2019/0112737 A1 | 4/2019 | Ashraf et al. |
| 2019/0254881 A1 | 8/2019 | Ishikawa et al. |
| 2019/0298586 A1 | 10/2019 | Ashraf et al. |
| 2019/0298587 A1 | 10/2019 | Ashraf et al. |
| 2019/0246196 A1 | 12/2019 | Han et al. |
| 2019/0374392 A1 | 12/2019 | Ninomiya et al. |
| 2019/0374404 A1 | 12/2019 | Ninomiya et al. |
| 2020/0155370 A1 | 5/2020 | Ohtsubo et al. |
| 2020/0155371 A1 | 5/2020 | Ohtsubo et al. |
| 2020/0206040 A1 | 7/2020 | Andrews et al. |
| 2020/0214901 A1 | 7/2020 | Andrews et al. |
| 2020/0298545 A1 | 9/2020 | Andrews et al. |

FOREIGN PATENT DOCUMENTS

| | | |
|---|---|---|
| CN | 1685099 | 10/2005 |
| CN | 101746057 | 6/2010 |
| CN | 105997351 | 10/2016 |
| EP | 0989218 | 3/2000 |
| EP | 1305248 | 5/2003 |
| EP | 1452157 | 9/2004 |
| EP | 1473148 | 11/2004 |
| EP | 1393701 | 7/2013 |
| EP | 3056176 | 8/2016 |

(56) References Cited

FOREIGN PATENT DOCUMENTS

| | | |
|---|---|---|
| EP | 3092997 | 8/2017 |
| EP | 3251642 | 12/2017 |
| EP | 3257488 | 12/2017 |
| EP | 3563817 A1 | 11/2019 |
| JP | 3213543 A | 9/1991 |
| JP | H 03213543 | 9/1991 |
| JP | H 04030847 | 2/1992 |
| JP | H 06254117 | 9/1994 |
| JP | 8071107 A | 3/1996 |
| JP | H 08071107 | 3/1996 |
| JP | H 08132576 | 5/1996 |
| JP | 2000026015 | 1/2000 |
| JP | 2000160460 | 6/2000 |
| JP | 3086141 B2 | 9/2000 |
| JP | 2002035029 | 2/2002 |
| JP | 2002178428 | 6/2002 |
| JP | 2002248127 | 9/2002 |
| JP | 2003521949 | 7/2003 |
| JP | 2004081365 | 3/2004 |
| JP | 2004229857 | 8/2004 |
| JP | 2004237410 | 8/2004 |
| JP | 2004254862 | 9/2004 |
| JP | 2004298362 | 10/2004 |
| JP | 2005320636 | 11/2005 |
| JP | 2006149747 | 6/2006 |
| JP | 2006149749 | 6/2006 |
| JP | 2006204673 | 12/2006 |
| JP | 2007190397 | 8/2007 |
| JP | 2008029749 | 2/2008 |
| JP | 2008055198 | 3/2008 |
| JP | 2008104853 | 5/2008 |
| JP | 2008105425 | 5/2008 |
| JP | 2008154998 | 5/2008 |
| JP | 2008148942 | 7/2008 |
| JP | 2008179128 | 8/2008 |
| JP | 2008194493 | 8/2008 |
| JP | 2008229006 | 10/2008 |
| JP | 2008229007 | 10/2008 |
| JP | 2008253290 | 10/2008 |
| JP | 2008260131 | 10/2008 |
| JP | 2008264480 | 11/2008 |
| JP | 2008272250 | 11/2008 |
| JP | 2008272253 | 11/2008 |
| JP | 2008296585 | 12/2008 |
| JP | 2009000161 | 1/2009 |
| JP | 2009039341 | 2/2009 |
| JP | 2009056156 | 3/2009 |
| JP | 2009106667 | 5/2009 |
| JP | 2009172231 | 8/2009 |
| JP | 2009240804 | 10/2009 |
| JP | 2009241607 | 10/2009 |
| JP | 2010131833 | 6/2010 |
| JP | 2011015707 | 1/2011 |
| JP | 2011111165 | 6/2011 |
| JP | 2011178124 | 9/2011 |
| JP | 2011225000 | 11/2011 |
| JP | 2012050882 | 3/2012 |
| JP | 2012050883 | 3/2012 |
| JP | 2012115358 | 6/2012 |
| JP | 2012521498 | 9/2012 |
| JP | 5124187 | 11/2012 |
| JP | 5124188 | 11/2012 |
| JP | 2013138795 | 7/2013 |
| JP | 2014097257 | 5/2014 |
| JP | 2014111222 | 6/2014 |
| JP | 2014188042 | 10/2014 |
| JP | 2015510831 | 4/2015 |
| JP | 2015521499 | 7/2015 |
| JP | 2016013687 | 1/2016 |
| JP | 2016016536 | 2/2016 |
| JP | 5942819 | 6/2016 |
| JP | 2016193199 | 11/2016 |
| JP | 6149635 | 6/2017 |
| JP | 2020054741 A | 4/2018 |
| JP | 2020054742 A | 4/2018 |
| JP | 2020054744 A | 4/2018 |
| JP | 2020054745 A | 4/2018 |
| JP | 2019081304 | 5/2019 |
| JP | 2019166804 | 10/2019 |
| JP | 2019181807 | 10/2019 |
| WO | WO 9925296 | 5/1999 |
| WO | WO 20030059603 | 7/2003 |
| WO | WO 20080123348 | 10/2008 |
| WO | WO 20030015681 | 2/2013 |
| WO | WO 20130084977 | 6/2013 |
| WO | WO 20140084168 | 6/2014 |
| WO | WO2014196669 A2 | 12/2014 |
| WO | WO 20160056092 | 4/2016 |
| WO | WO 20160056093 | 4/2016 |
| WO | WO 20160063346 | 4/2016 |
| WO | WO 20160067387 | 5/2016 |
| WO | WO 20160071981 | 5/2016 |
| WO | WO 20160075974 | 5/2016 |
| WO | WO 20160098416 | 6/2016 |
| WO | WO 20160104412 | 6/2016 |
| WO | WO 20160104422 | 6/2016 |
| WO | WO 20160158499 | 10/2016 |
| WO | WO 20160158746 | 10/2016 |
| WO | WO 20160208502 | 12/2016 |
| WO | WO 20160208513 | 12/2016 |
| WO | WO 20170105997 | 6/2017 |
| WO | WO 2018061288 | 4/2018 |
| WO | WO 2018084145 | 5/2018 |
| WO | WO 2018154680 A1 | 8/2018 |
| WO | WO 2018154682 A1 | 8/2018 |
| WO | WO 2018167836 A1 | 8/2018 |
| WO | WO 2019046363 | 3/2019 |
| WO | WO 2019111203 | 6/2019 |
| WO | WO 2019150802 A1 | 8/2019 |
| WO | WO 2020006996 | 1/2020 |

OTHER PUBLICATIONS

U.S. Appl. No. 15/833,057, filed Dec. 6, 2017, Schneider.
3D Nonwovens Developments for textured nonwovens; Detlef Frey; http://web.archive.org/web/20170919080326/https://www.reicofil.com/en/pages/3d_nonwovens, Sep. 19, 2017.
American Cancer Society—What Cancer Patients Their Families and Caregivers Need to Know About COVID 19—Is Impacting Our Patient Services, printed Mar. 31, 2020.
ASTM—Standard Tables of Body Measurements for Adult Females Misses Figure Type Size Range 00-20, printed Mar. 13, 2020.
ASTM—Standard Tables of Body Measurements for Children Infant Size—Preemie to 24 Months, printed Mar. 30, 2020.
PCT International Search Report for PCT/US2017/067255, dated Apr. 12, 2018 (6 pages).
All Office Actions, U.S. Appl. No. 15/831,448, 2019-2020.
All Office Actions, U.S. Appl. No. 15/831,464, 2019-2020.
All Office Actions, U.S. Appl. No. 15/832,929, 2019-2020.
All Office Actions, U.S. Appl. No. 15/833,057, 2019-2020.
All Office Actions, U.S. Appl. No. 15/846,745, 2020.
All Office Actions, U.S. Appl. No. 15/838,405, 2019-2020.
All Office Actions, U.S. Appl. No. 15/839,896, 2019-2020.
All Office Actions, U.S. Appl. No. 15/846,382, 2019-2020.
All Office Actions, U.S. Appl. No. 15/846,341, 2020.
All Office Actions, U.S. Appl. No. 15/846,360, 2020.
All Office Actions, U.S. Appl. No. 15/846,371, 2020.
All Office Actions, U.S. Appl. No. 15/846,391, 2020.
All Office Actions, U.S. Appl. No. 15/846,409, 2020.
All Office Actions, U.S. Appl. No. 15/846,433, 2020.
All Office Actions, U.S. Appl. No. 16/117,579, 2020.
All Office Actions, U.S. Appl. No. 16/115,617, 2020.

* cited by examiner

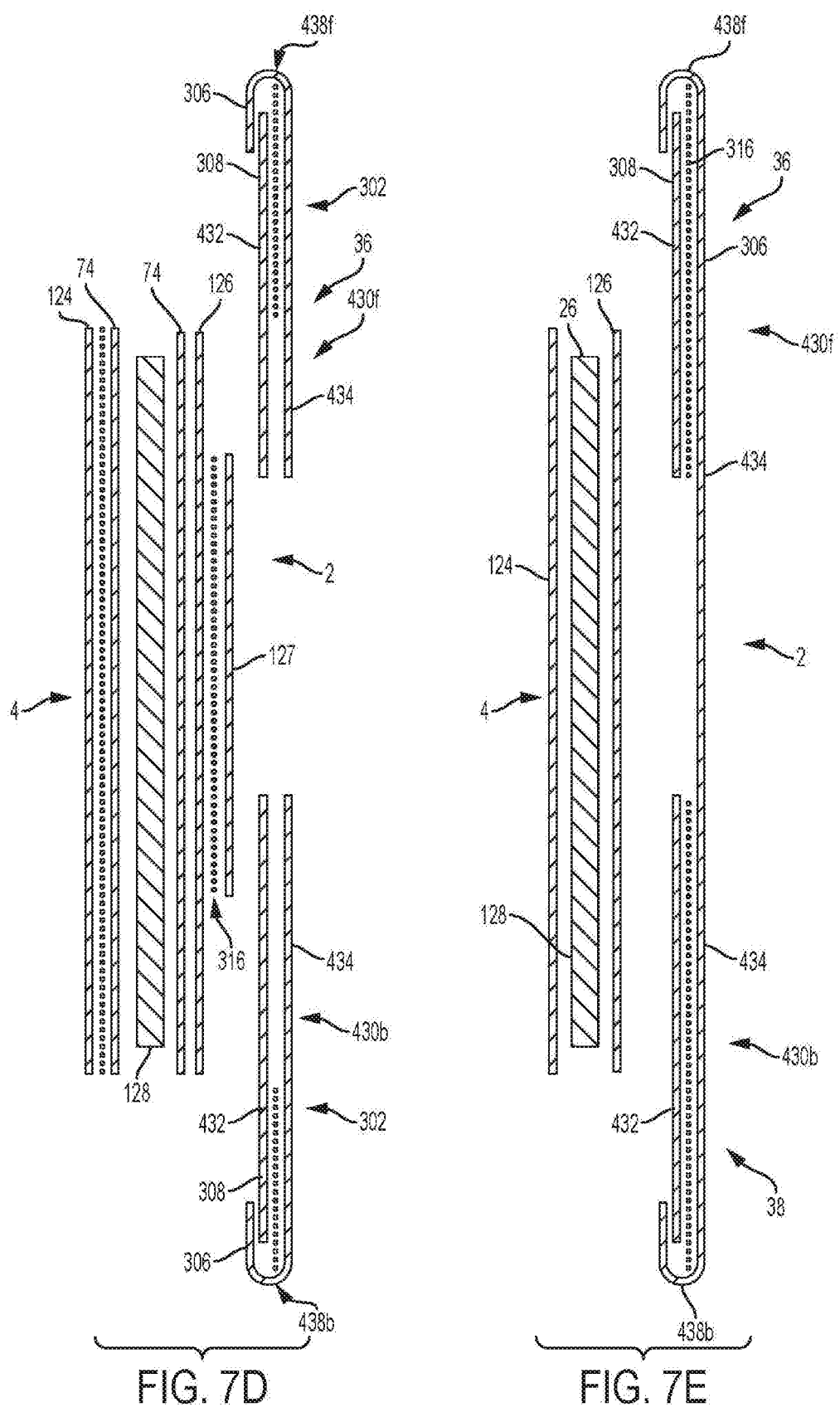

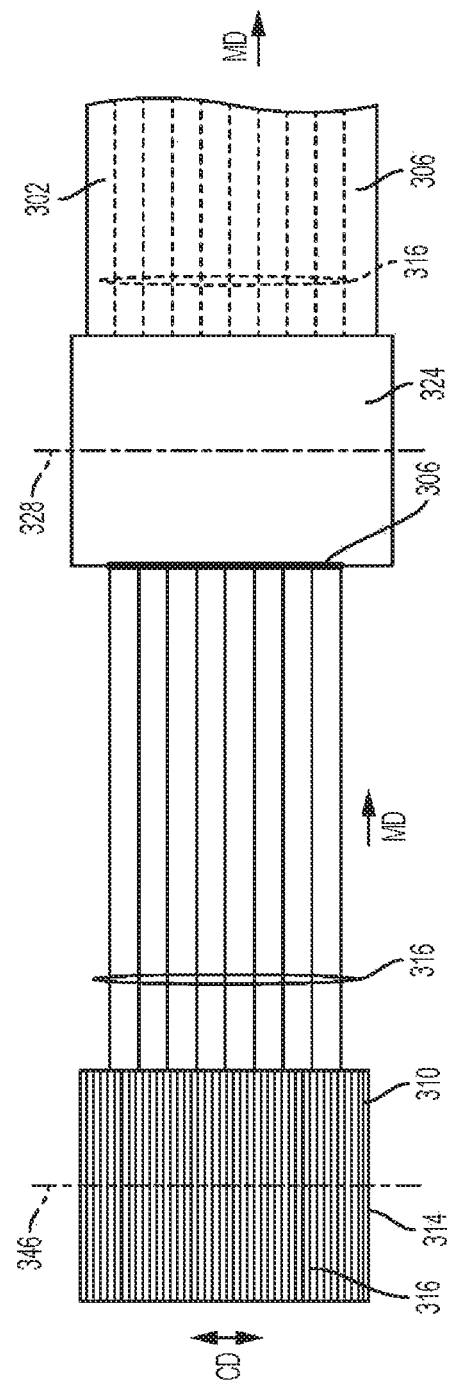

DISPOSABLE ABSORBENT ARTICLES HAVING CUFFS OF IMPROVED STRETCH LAMINATE STRUCTURE

CROSS-REFERENCE TO RELATED APPLICATIONS

This application claims the benefit, under 35 USC 119(e), to U.S. Provisional Patent Application No. 62/436,589, filed on Dec. 20, 2016 (P&G 14618P); U.S. Provisional Patent Application No. 62/483,965, filed on Apr. 11, 2017 (P&G 14778P); U.S. Provisional Patent Application No. 62/553,149, filed on Sep. 1, 2017 (P&G 14917P); U.S. Provisional Patent Application No. 62/553,171, filed on Sep. 1, 2017 (P&G 14918P); U.S. Provisional Patent Application No. 62/553,538, filed on Sep. 1, 2017 (P&G 14921P); and U.S. Provisional Patent Application No. 62/581,278, filed on Nov. 3, 2017 (P&G 15007P); each of which are herein incorporated by reference in their entirety.

FIELD OF THE INVENTION

The present disclosure relates to absorbent articles, more particularly, to disposable absorbent articles including improved elastic laminates configured to perform in various components of the disposable absorbent articles.

BACKGROUND OF THE INVENTION

Elasticized laminates, also known as stretch laminates, are frequently used as components of absorbent articles such as diapers and absorbent pants. Stretch laminates may be used to form, for example, elastically stretchable back ears or fastening members of diapers, elastically stretchable side panels of bicycle-style absorbent pants, and elastically stretchable waist belt structures in belt- or balloon-style absorbent pants.

As used in these products, stretch laminates are typically formed of an elastic film or array of parallel elastic strands, sandwiched between two layers of relatively non-elastic nonwoven web material. To impart the laminate with elastic stretchability and contractibility, the elastic material is typically incorporated into the laminate under a desired amount of pre-strain along the direction of the desired stretchability of the laminate. Upon completion of manufacture, the elastic material relaxes and contracts along the direction of the pre-strain toward its unstrained dimension, causing the sandwiching nonwoven materials to form corrugations or ruffles of gathered material. The ruffles of gathered material help impart the laminate with substantially nondestructive elastic stretchability by an amount approximately corresponding to the amount of pre-strain, along the direction of the pre-strain.

Depending upon their structure, stretch laminates of the prior art may have appearance and/or performance characteristics that consumers of wearable products including these laminates as components may perceive negatively. For example, suitable laminates incorporating elastic strands typically include an array of elastic strands of a decitex (also referred to herein as "dtex"), strand spacing, and pre-strain level, that in combination may result in concentrations of pressure beneath the individual strands against the wearer's skin, and clearly visible, somewhat irregularly distributed rugosities (formed of material gathered along the direction of pre-strain of the strands) in the laminate. These features can cause skin marking and reduced comfort for the wearer, as well as impart the laminate (and the article) with bulky, mottled, ruffled, non-garment-like (e.g., diaper-like) appearance.

Traditional strand-based laminates typically include elastic strands spaced apart by a minimum distance, primarily due to manufacturing and material handling limitations. Each elastic strand is supplied on an individual spool. During manufacture of the laminate, each strand must be unwound from its own spool using equipment to control tension in the strand and guide it to position as it is introduced to the other layers to make up the laminate. This creates a practical constraint on the number of strands that may be incorporated into a laminate per unit cross-direction width of the laminate and in total. Strand-based stretch laminates with cross-direction strand spacing less than about 4.0 mm are not believed to have appeared in the market.

Additionally, extruded elastic strands and/or extruded elastic scrim materials typically include thermoplastic materials that undergo substantial stress relaxation over time when stretched, and thus may not maintain the desired tensile forces about the wearer's body—e.g., the waist and legs, to provide sustained desired fit and gasketing (i.e., protection against leakage of bodily exudates) over the entire intended time of wear of the article in which the stretch laminate is incorporated. This effect becomes more substantial as the level of pre-strain imparted to the strands during manufacture of the laminate is increased.

Elastic film-based laminates are typically substantially more occlusive (i.e., less breathable, with greatly reduced air permeability) than strand-based laminates. As a consequence, articles having such laminates as components may for the wearer feel hot and sticky against the skin, and may cause greater hydration of the skin, and as a result, reduced comfort and increased marking and potential for irritation, associated with overly hydrated skin.

Additionally, elastic film-based elasticized laminates typically have a higher modulus versus strand-based elasticized laminates; this can make articles in which they are components comparatively more difficult to apply to a wearer (making it difficult to open for donning). In turn, the manufacturer may be compelled to manufacture the article with an elastic film of sufficient caliper to impart the desired degree of elasticity and contractive force, thereby involving relatively greater use of the relatively expensive resins used to form elasticizing components.

As a result of the issues described above there has been a long-standing and unmet need to provide an improved stretch laminate suitable for use for forming various components of products such as disposable diapers, disposable training pants and adult incontinence pads and pants, that reduces areas of localized pressure on the wearer's skin, provides a high level of breathability, provides adequate force for sustained and comfortable fit, low modulus, high extensibility, low stress relaxation and a smooth, cloth-like texture. The desired stretch laminate would have good breathability and minimized areas of localized pressure for skin comfort, minimized skin marking and hydration, uniform and generous elastic extensibility and contraction for ease of donning and removal of the article, improved sustained fit, and improved body conformity and wearer comfort.

BRIEF DESCRIPTION OF THE DRAWINGS

FIG. 7D is a cross section view of an alternate embodiment of the pant of FIG. 7 taken along the longitudinal axis 42, showing longitudinally opposing discrete belts, wherein a plurality of elastics 316 are oriented parallel with the lateral axis 44 between the core wrap 74 and the topsheet 124 and oriented parallel with the lateral axis 44 between the backsheet film 126 and the backsheet nonwoven 127. FIG. 7E is a cross section view of an alternate embodiment of the belt pant of FIG. 7 taken along the longitudinal axis 42, showing longitudinally opposing discrete inner belt layers 432 and a common outer belt layer 434, and showing a plurality of elastics 316 extending continuously across the core.

FIG. 14A is a view of the converting apparatus of FIG. 14 taken along line 14A-14A.

DETAILED DESCRIPTION

Figure 1:
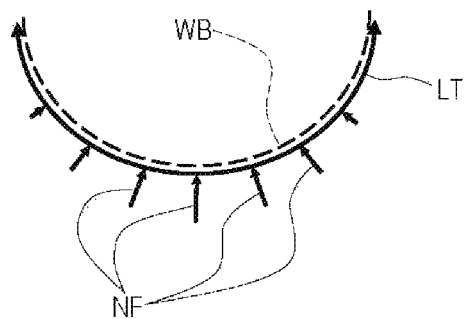
FIG. 1 is a schematic illustration of forces in an elasticized cuff structure acting about and upon a wearer, from a side view perspective.

The present disclosure details improved elastic laminates (also referred to as "beamed elastic laminates" including "beamed elastics") including a greater number of elastic strands having a greater fineness (i.e., lower decitex) and a closer spacing than has been previously disclosed or practiced in disposable absorbent articles. These improved elastic laminates can be used as disposable absorbent article (for, example, taped diapers, pants, pads, and liners) components for fit and gasketing at the waist, legs, crotch and sides of the wearer to generally provide the greatest level of extensibility, the most comfortable wearing conditions, improved leakage protection and a better fit.

The following term explanations may be useful in understanding the present disclosure:

"Disposable," in reference to absorbent articles, means that the absorbent articles, are generally not intended to be laundered or otherwise restored or reused as absorbent articles (i.e., they are intended to be discarded after a single use and, preferably, to be recycled, composted or otherwise discarded in an environmentally compatible manner). Disposable absorbent articles often include adhesive between the layers and/or a plurality of elastics to hold the article together (e.g., ear panels, side panels, and belts are joined to the chassis via adhesive and the layers of the ear panels, side panels, belts, and chassis are joined together using adhesive). Alternatively, heat and/or pressure bonding are used with the adhesive or in place of the adhesive. In such instances portions of the material layers may become partially melted and pressed together such that once cooled they are physically bonded together. Nonwovens (including, for example, polypropylene, polyethylene, etc.) adhesives (including, for example, styrenic block copolymers (e.g., SIS, SBS)), and absorbent gelling material (AGM 51—see FIGS. 7 and 7B) make up more than 50%, more than 75%, and often more than 90% of the disposable absorbent article weight. And, a core including the AGM 51 is often held within the chassis in a manner that would encapsulate and contain the AGM 51 under normal conditions. Such disposable absorbent articles typically have an absorbent capacity of greater than about 100 mL of fluid and can have capacities of up to about 500 mL of fluid or more. Stitching (including the use of thread) and/or woven materials are typically not used to make a disposable absorbent article. If stitching or woven materials are used, they make up an extremely small percentage of the disposable absorbent article. Some landing zones of disposable absorbent articles for fasteners can include a woven material, but no other part of a disposable absorbent article typically includes woven materials.

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, feminine pads, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal axis than the distal edge of the same element is located relative to the same longitudinal axis).

"Inboard" and "outboard" are relative terms that indicate the location of a first feature relative the location of a second feature, and relative a longitudinal axis of an absorbent article. A first feature is inboard of a second feature, and the second feature is outboard of the first feature, when the first feature is closer to the longitudinal axis than the second feature.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

With respect to a disposable absorbent article adapted to be worn about a wearer's lower torso, "longitudinal" and forms thereof refer to a direction substantially perpendicular to the forward and rearward edges (sometimes called the front and rear waist edges) of the article at their midpoints.

With respect to a disposable absorbent article adapted to be worn about a wearer's lower torso, "lateral" and forms thereof refer to a direction substantially parallel to the forward and rearward edges (sometimes called the front and rear waist edges) of the article at their midpoints, or substantially perpendicular to the longitudinal direction.

"Disposed" refers to an element being located in a particular place or position.

"Joined" encompasses configurations whereby an element is directly secured to another element by affixing the element directly to the other element, and configurations whereby an element is indirectly secured to another element by affixing the element to intermediate member(s), which, in turn are affixed to the other element.

"Liquid-permeable" and "liquid-impermeable" refer to the penetrability of materials in the context of the intended usage of disposable absorbent articles. Specifically, the term "liquid-permeable" refers to a layer or a layered structure having pores, openings, and/or interconnected void spaces that permit aqueous liquid such as water, urine, or synthetic urine to pass through its thickness in the absence of a forcing pressure. Conversely, the term "liquid-impermeable" refers to a layer or a layered structure through the thickness of which aqueous liquid such as water, urine, or synthetic urine cannot pass in the absence of a forcing pressure (aside from natural forces such as gravity). A layer or a layered structure that is liquid-impermeable according to this definition may be permeable to liquid vapor, i.e., may be "vapor-permeable."

"Elastic," "elastomer," or "elastomeric" refers to a material or combination of materials exhibiting elastic properties, by which, upon application of a tensile force to its relaxed, initial length, the material or combination of materials can stretch or elongate to an elongated length more than 10% greater than its initial length, and following such elongation and upon release of the applied tensile force, will contract back toward its initial length by at least 50% of the elongation. Elastomeric materials may include elastomeric films, scrims, nonwovens, ribbons, strands, and other sheet-like structures, and stretch laminates.

"Pre-strain" refers to the strain imposed on an elastic or elastomeric material prior to combining it with another element of an elastic laminate or the absorbent article. Pre-strain is determined by the following equation:

$$\text{Pre-strain} = 100\% \times \frac{\left[\begin{array}{c}(\text{extended length of the material}) - \\ (\text{relaxed length of the material})\end{array}\right]}{(\text{relaxed length of the material})}$$

"Decitex" also known as "dtex" is a unit used in the textile industry used to express linear mass density of fibers and yarns. 1 decitex=1 gram per 10,000 meters. For example, if 10,000 linear meters of a yarn or filament weighs 500 grams, it is 500 decitex.

"Substrate" is used herein to describe a material which is primarily two-dimensional (i.e. in an X-Y plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, films and foils such as polymeric films or metallic foils. These materials may be used alone or may include two or more layers laminated together. As such, a web is a substrate.

"Nonwoven" refers herein to a cloth-like web material made from a consolidated deposition of continuous (long) filaments (fibers) and/or discontinuous (short) filaments (fibers) by processes such as spunbonding, meltblowing, carding, and other methods that do not include weaving or knitting to consolidate the filaments or fibers into a web.

"Machine direction" (MD) is used herein to refer to the direction of material movement through equipment used to effect a process. In addition, relative placement and movement of material can be described as moving in the machine direction through the equipment from upstream in the process to downstream in the process.

"Cross direction" (CD) is used herein to refer to a direction that is generally perpendicular to the machine direction.

"Taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be pre-formed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be pre-formed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Closed-form" means opposing waist regions are joined, as packaged, either permanently or refastenably to form a continuous waist opening and leg openings.

"Open-form" means opposing waist regions are not initially joined to form a continuous waist opening and leg openings but include a closure means such as a fastening system to join the waist regions to form the waist and leg openings before or during application to a wearer of the article.

The term "channel," as used herein, is an elongate region or zone in an absorbent material layer that has a substantially lower basis weight (e.g., less than 50%, less than 70%, less than 90%) than the surrounding material in the material layer. The channel may be a region in a material layer that is substantially absorbent material-free (e.g., 90% absorbent material-free, 95% absorbent material-free, or 99% absorbent material-free, or completely absorbent material-free). A channel may extend through one or more absorbent material layers.

Herein, an "elastic strand" or "strand" refers to a yarn-like bundle of a plurality of individual filaments each spun or extruded of elastomeric material, combined together into an effectively unitary structure. The filaments may or may not be twisted about each other, as in the fiber or filament constituents of a twisted multi-fiber and/or multi-filament yarn. The low-decitex elastic strands contemplated for use herein as beamed elastic strands may have no more than 30 filaments, no more than 20 filaments, no more than 15 filaments or even no more than 10 filaments per strand.

"z-direction," with respect to a web component of an absorbent article, means the direction orthogonal to an x-y plane occupied by the web component when it is laid out flat.

"Average-Pre-Strain" of a plurality of elastic strands within a stretch laminate is determined according to the Average-Pre-Strain measurement method set forth herein.

"Average Decitex" or "Average Dtex" of a plurality of elastic strands within a stretch laminate is determined according to the Average Decitex measurement method set forth herein.

"Average-Strand-Spacing" of a plurality of elastic strands within a stretch laminate is determined according to the Average-Strand-Spacing measurement method set forth herein.

"Manufacturing Pre-Strain" means the average amount, specified by the manufacturer of an article or stretch laminate component thereof, by which a plurality of elastic strands of an elasticized band are elongated together as they are unwound from a single warp beam, from their relaxed length, as they are first joined to one or more web materials in a process to form a stretch laminate. Manufacturing Pre-Strain may be specified directly, or it may be specified indirectly, e.g., by tensile force under which the strands are placed as they are joined with the web material. Where not specified directly, Manufacturing Pre-Strain may be calculated and/or determined based upon, e.g., the Manufacturing Decitex, material modulus, number of strands, and applied tensile force specified by the manufacturer for manufacturing the laminate.

"Manufacturing Decitex" or "Manufacturing Dtex" means the average decitex of a plurality of elastic strands, specified by the manufacturer of an article or stretch laminate component thereof, that are supplied on and unwound from a single warp beam and joined to one or more web materials to form the stretch laminate.

"Manufacturing Strand Spacing" means the average center-to-center spacing among a plurality of elastic strands, specified by the manufacturer of an article or stretch laminate component thereof, that are unwound from a single warp beam and joined to one or more web materials to form the stretch laminate, at the time they are first joined to the one or more materials.

Examples of Absorbent Articles Contemplated

Products including elastic laminates contemplated herein may include absorbent articles of differing structure and/or form that are generally designed and configured to manage bodily exudates such as urine, menses, and/or feces, such as disposable taped and pants, including baby and adult disposable absorbent articles.

Figure 3:
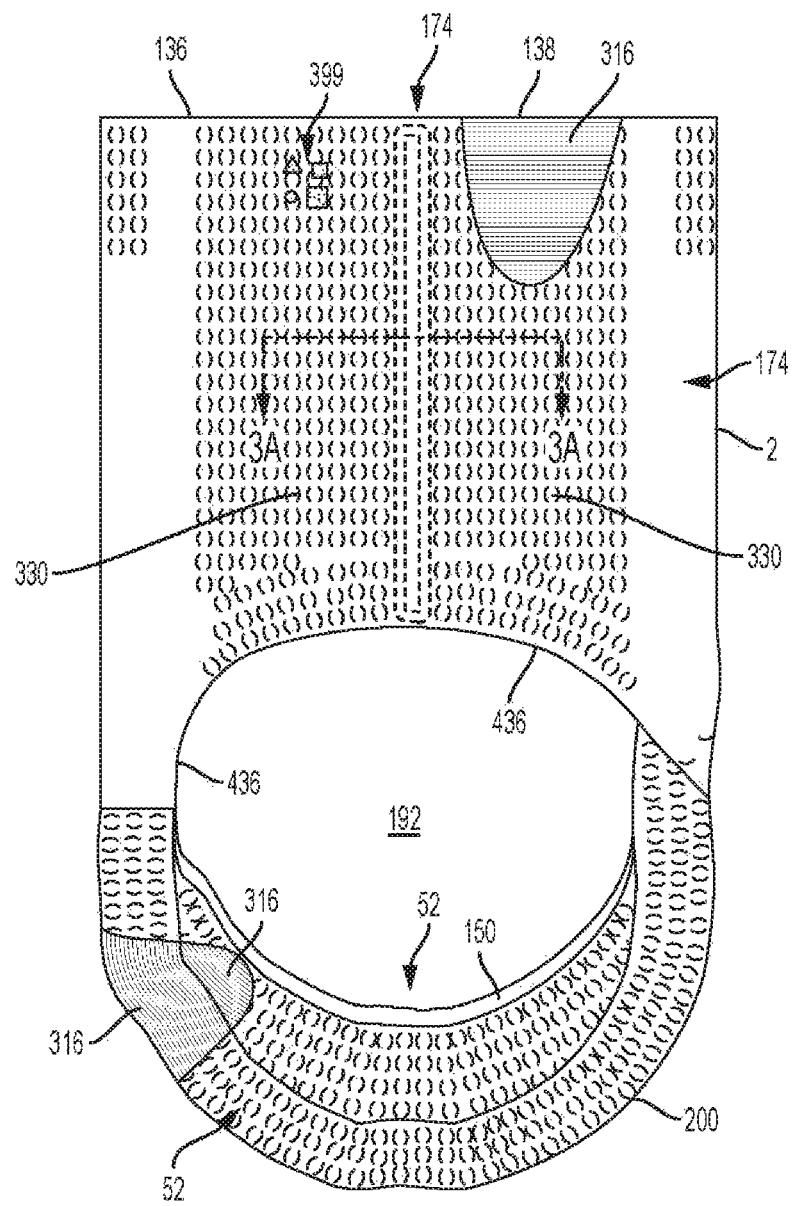
FIG. 3 is a side view of a pant including side panels with refastenable side seams.
Figure 3A:
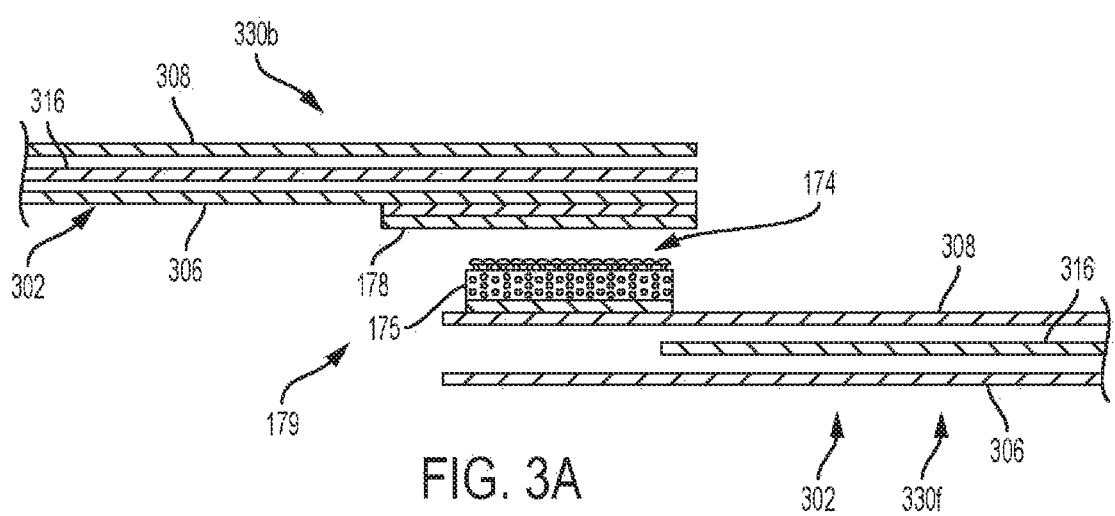
FIG. 3A is a cross section view of a refastenable seam taken along line 3A-3A of the pant of FIG. 3.
Figure 3B:
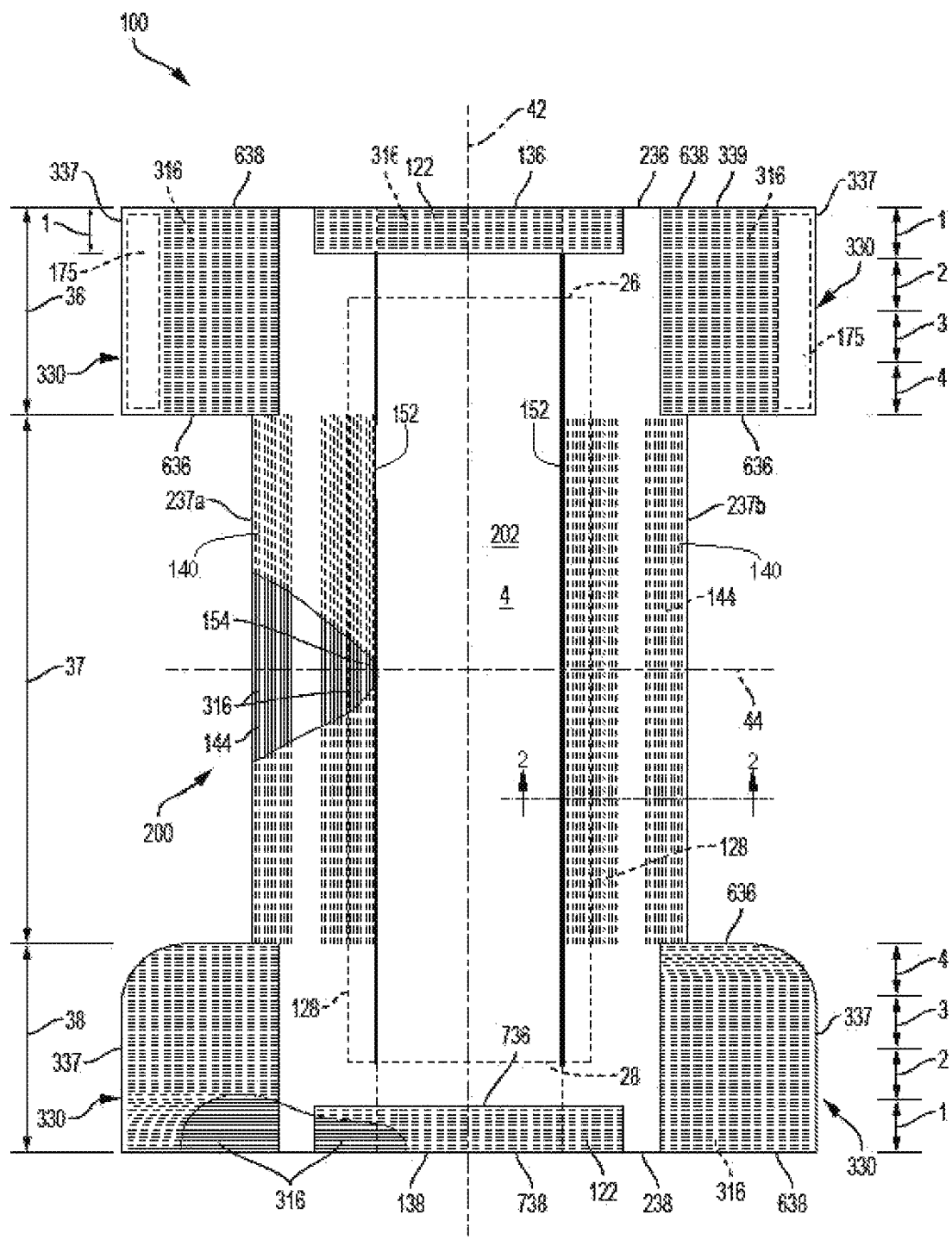
FIG. 3B is a plan view of the pant illustrated in FIG. 3, prior to joining the side panels to form the waist and leg openings.

As shown in FIG. 3B, an absorbent article 100 may include a chassis 200 including a topsheet 124, a backsheet 125, and an absorbent core 128 disposed at least partially between the topsheet 124 and the backsheet 125. The chassis 200 may further include an inner barrier leg cuff 150 and an outer leg cuff 140 (the cuffs generally referred to as 52).

One end portion of an absorbent article 100 may be configured as a front waist region 36 and the longitudinally opposing end portion may be configured as a back waist region 38. An intermediate portion of the absorbent article 100 extending longitudinally between the front waist region 36 and the back waist region 38 may be configured as a crotch region 37. The length of each of the front waist region 36, the back waist region 38 and the crotch region 37 may be about ⅓ of the length of the absorbent article 100, for example (see, for example, FIGS. 9 and 10). Alternatively, the length of each of the front waist region 36, the back waist region 38, and the crotch region 37 may have other dimensions (e.g., defined by the belt or ear panel or side panel dimensions—see, for example, FIGS. 3B, 4, and 7). The absorbent article 100 may have a laterally extending front waist end edge 136 in the front waist region 36 and a longitudinally opposing and laterally extending back waist end edge 138 in the back waist region 38.

The chassis 200 of the absorbent article 100 may include a first longitudinally extending side edge 237a and a laterally opposing and second longitudinally extending side edge 237b. Both of the side edges 237 may extend longitudinally between the front waist end edge 136 and the back waist end edge 138. The chassis 200 may form a portion of the laterally extending front waist end edge 136 in the front waist region 36 and a portion of the longitudinally opposing and laterally extending back waist end edge 138 in the back waist region 38. Furthermore, the chassis 200 may include a chassis interior surface 202 (forming at least a portion of the wearer-facing surface 4), a chassis exterior surface 204 (forming at least a portion of the garment-facing surface 2), a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 237a and through a midpoint of the second side edge 237b.

Figure 7:
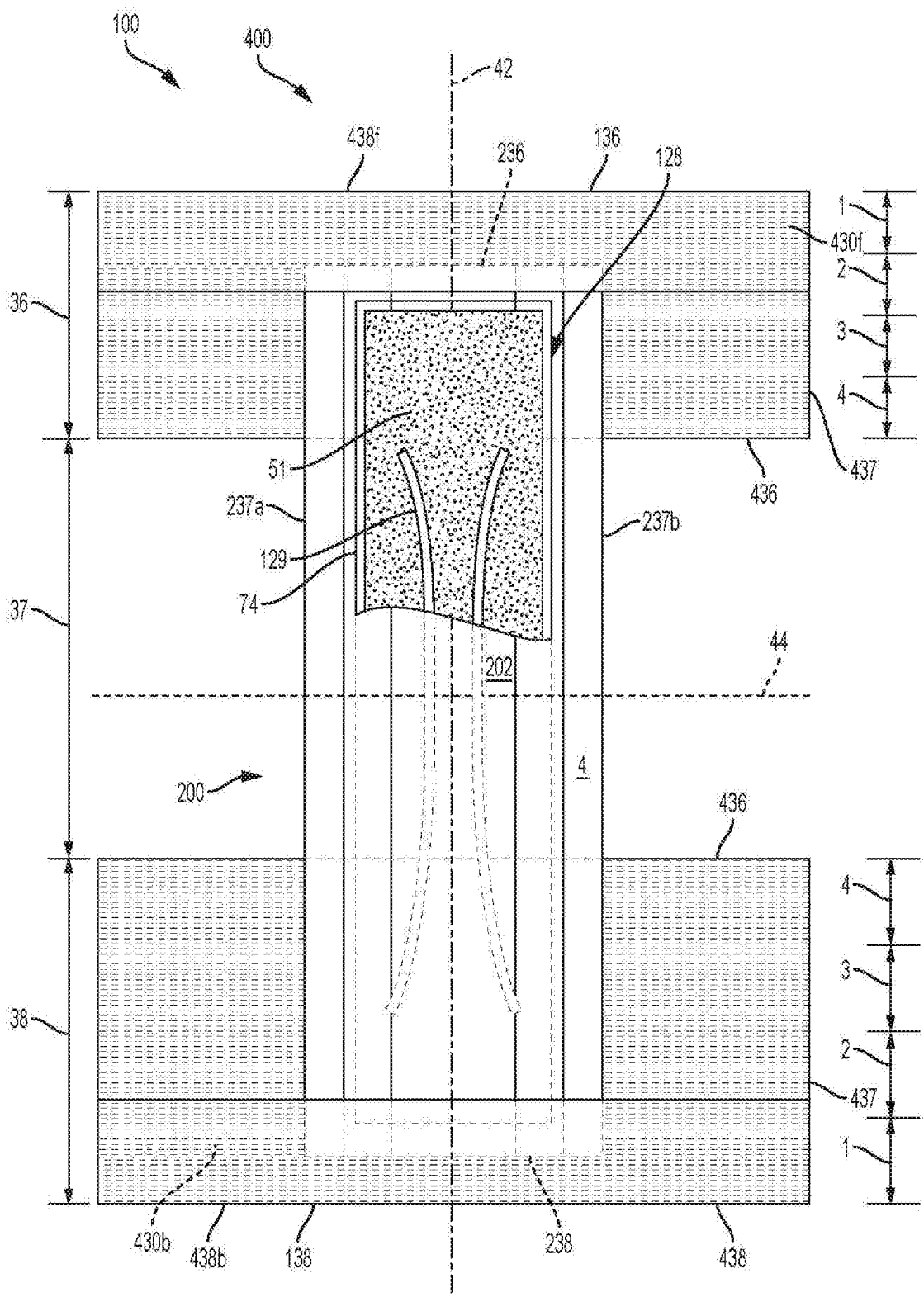
FIG. 7 is a plan view of the pant of FIG. 6, prior to joining side edges of the belt to form the waist and leg openings.

Referring to FIG. 7, often true for belted absorbent articles, the chassis 200 may have a length measured along the longitudinal axis 42 that is less than the length of the absorbent article 100. Both of the side edges 237 of the chassis 200 may not extend longitudinally to one or both of the front waist end edge 136 and the back waist end edge 138. The chassis 200 may not form a portion of one or both of the laterally extending front waist end edge 136 in the front waist region 36 and the longitudinally opposing and laterally extending back waist end edge 138 in the back waist region 38.

Figure 7A:
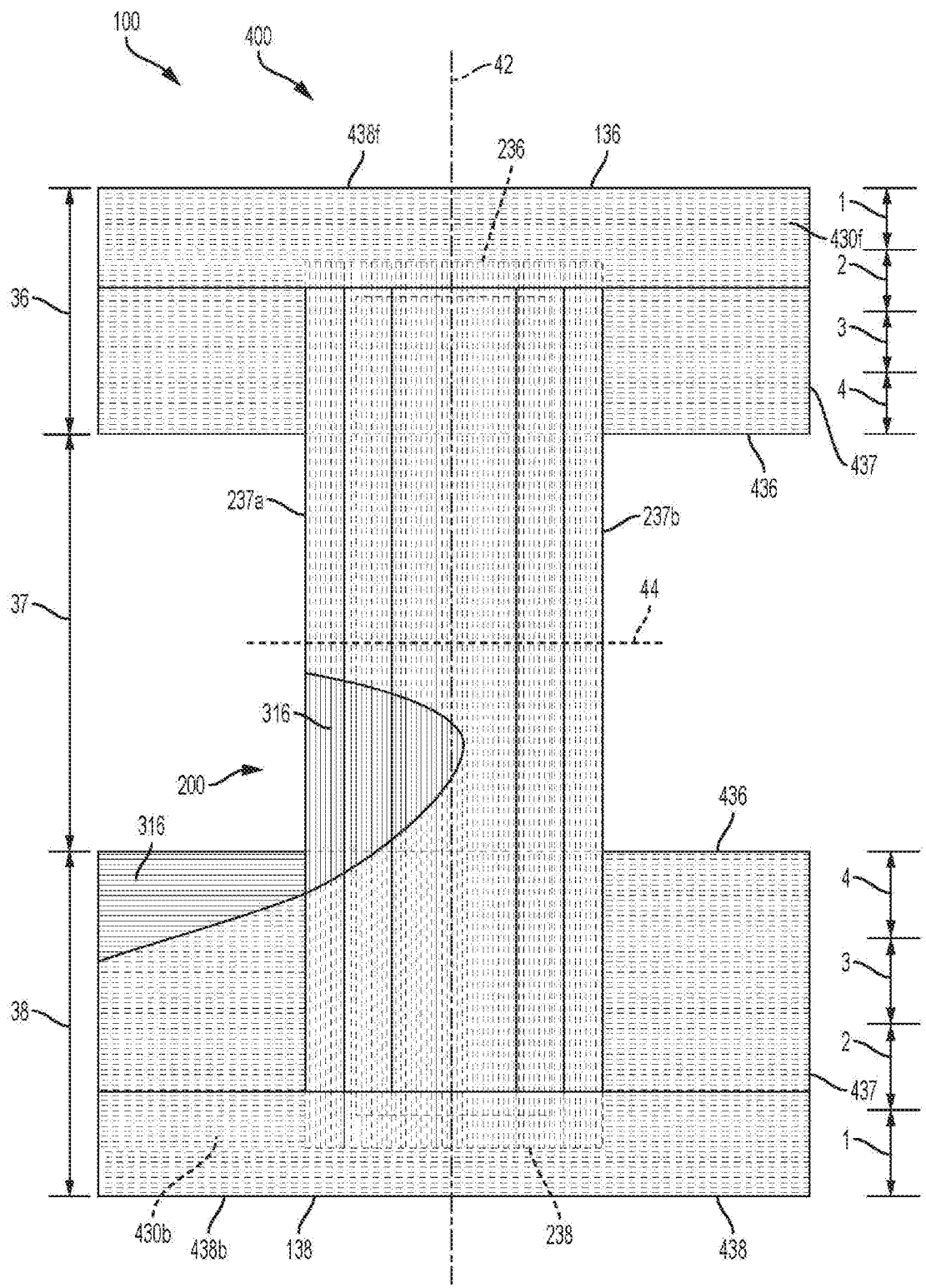
FIG. 7A is a plan view of an alternate embodiment of the belt pant of FIG. 7 illustrating an elasticized topsheet and an elasticized backsheet.
Figure 7B:
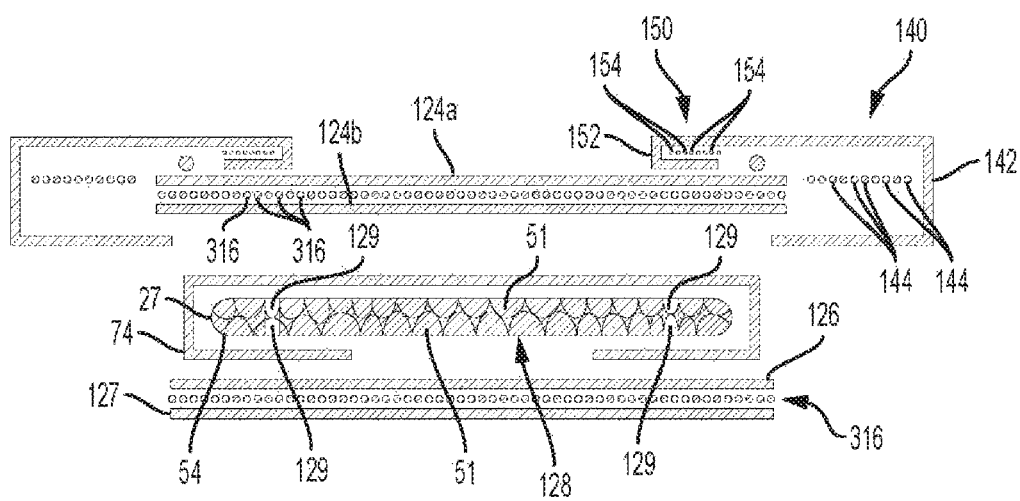
FIG. 7B is a cross section view of the pant of FIG. 7A taken along the transverse axis, illustrating the elasticized topsheet (showing a plurality of elastics 316 oriented parallel with the longitudinal axis 42) and the elasticized backsheet (showing a plurality of elastics 316 oriented parallel with the longitudinal axis 42).
Figure 7C:
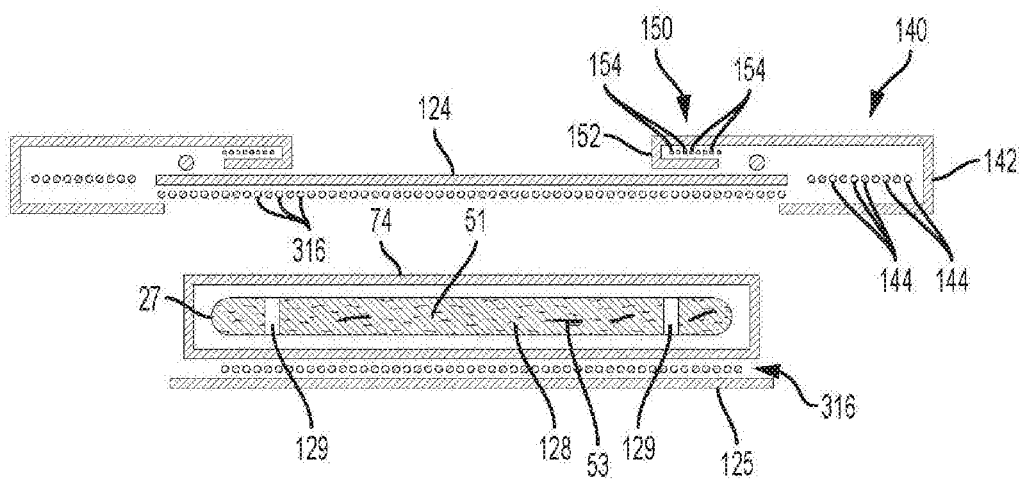
FIG. 7C is a cross section view of an alternate embodiment of the pant of FIG. 7A taken along the transverse axis, wherein the core wrap completely surrounds the core 128, wherein a plurality of elastics 316 are oriented parallel with the longitudinal axis 42 between the core wrap 74 and the backsheet 125 and oriented parallel with the longitudinal axis 42 between the core wrap 74 and the topsheet 124, and wherein the core 128 includes AGM 51 mixed with pulp 53.

Referring to FIG. 7B, the chassis 200 may include a plurality of elastics 316 are oriented parallel with the longitudinal axis 42 between the backsheet nonwoven 127 and backsheet film 126. FIG. 7C shows an alternate embodiment than FIG. 7B, where the chassis 200 has a plurality of elastics 316 oriented parallel with the longitudinal axis 42 between the core wrap 74 and the backsheet 125. Still further, FIG. 7D shows another alternative embodiment where the chassis 200 includes a plurality of elastics 316 oriented parallel with the lateral axis 44 between the backsheet film 126 and the backsheet nonwoven 127. FIG. 7B also shows a plurality of elastics 316 oriented parallel with the longitudinal axis 42 between a first topsheet layer 124a and a second topsheet layer 124b, whereas FIG. 7C shows an alternate embodiment where the plurality of elastics 316 are between the topsheet 124 and the core wrap 74. Still further, FIG. 7D shows a plurality of elastics 316 oriented parallel with the lateral axis 44 between the topsheet 124 and the core wrap 74.

Figure 12:
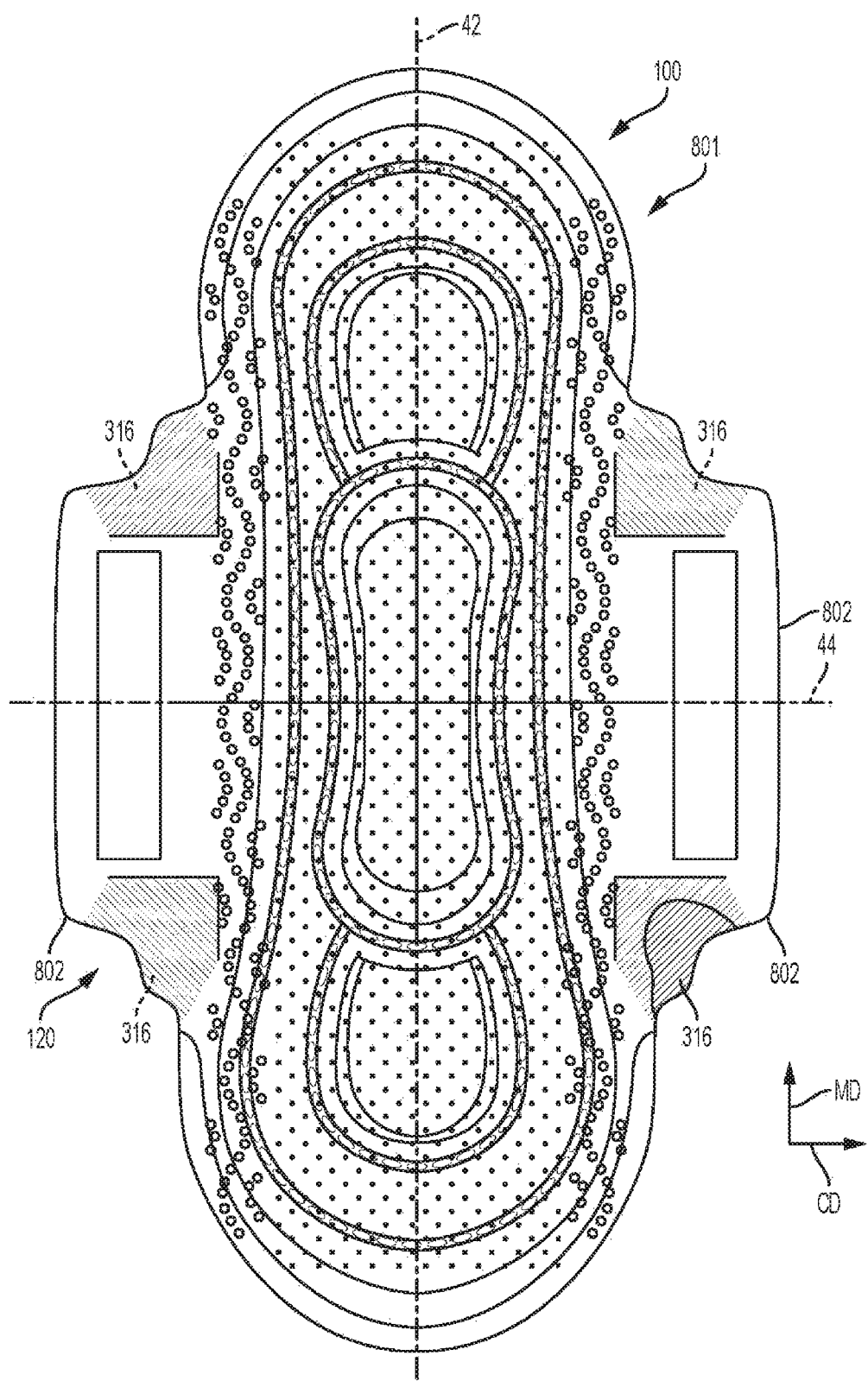
FIG. 12 is an interior plan view of a feminine hygiene article 801, specifically a pad, illustrating elasticized wings 802, where the plurality of elastics 316 are at approximately 45 degree angles relative to the longitudinal axis 42 and lateral axis 44.
Figure 12A:
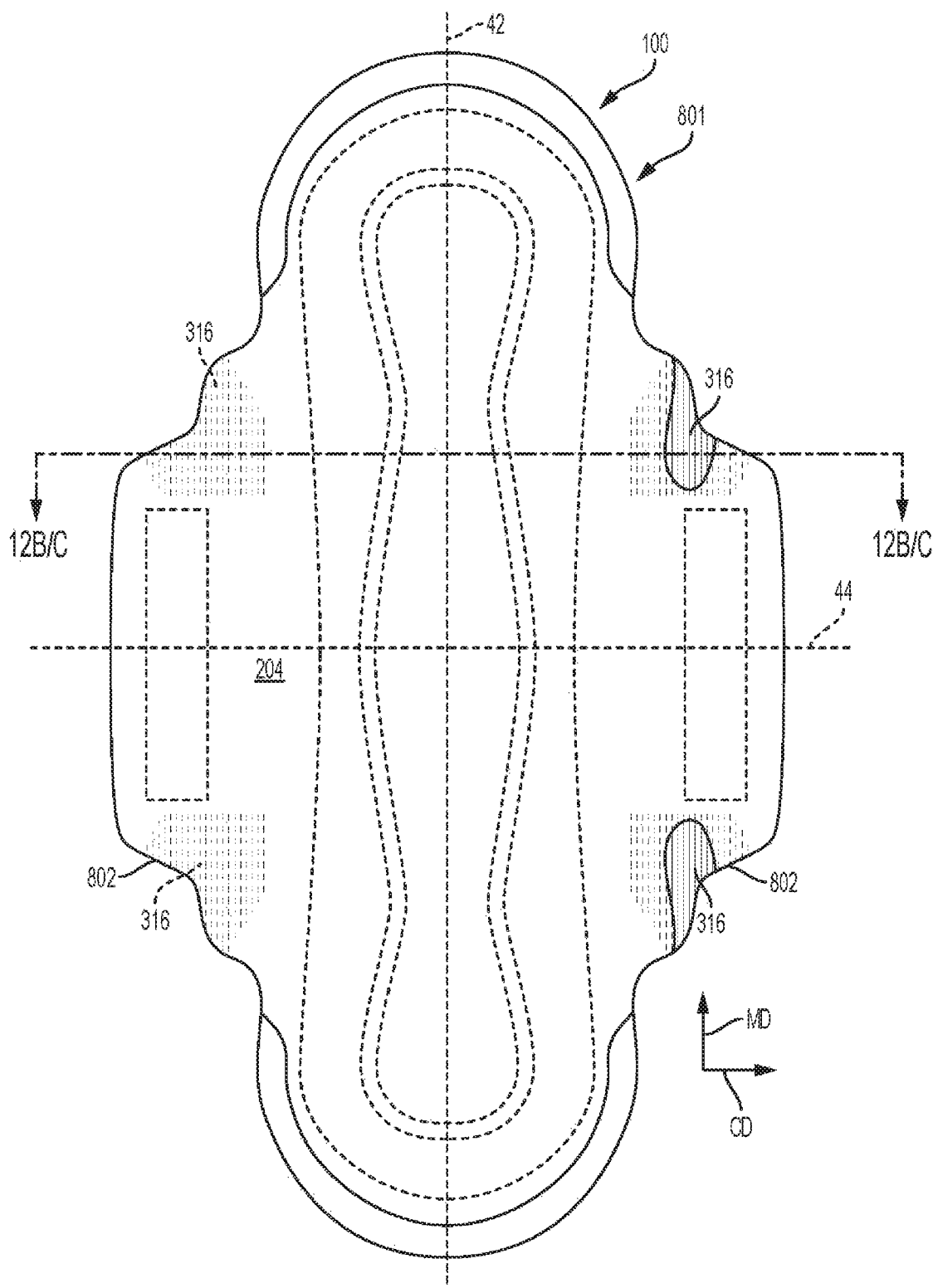
FIG. 12A is an exterior plan view of an alternative embodiment of the feminine hygiene article 801 of FIG. 12 illustrating elasticized wings 802, wherein the plurality of elastics 316 are oriented parallel with the longitudinal axis 42.

Still regarding an elasticized chassis 200, FIGS. 12A, B, and C show an elasticized chassis 200, where a plurality of elastics 316 are disposed between layers of the wings 120.

Figure 12B:
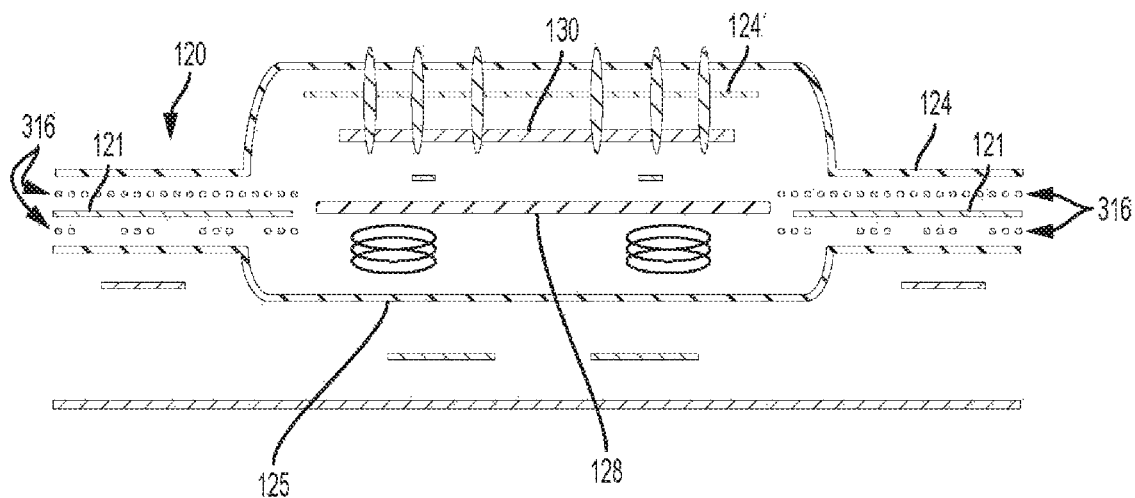
FIG. 12B is a cross section view of the feminine hygiene article 801, along line 12B/C-12B/C of the feminine hygiene article 801 of FIG. 12A, illustrating strands between the layers making up the wings.
Figure 12C:
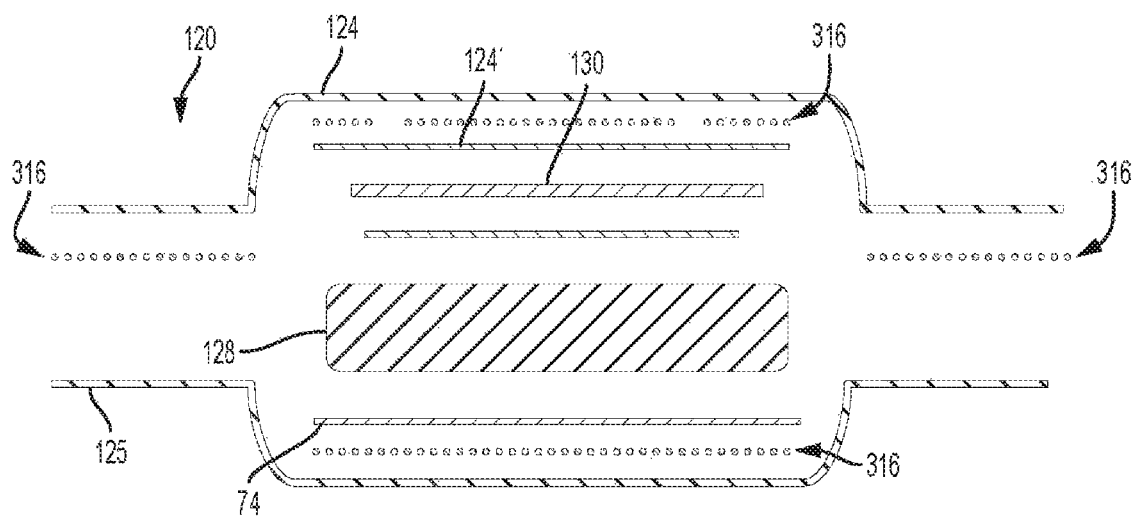
FIG. 12C is a cross section view of an alternative embodiment of the feminine hygiene article 801, along line 12B/C-12B/C of the feminine hygiene article 801 of FIG. 12A, illustrating only one layer of strands between the layers making up the wings, as well as strands underlying or forming a portion of the topsheet 124 and secondary topsheet 124'.

FIG. 12 shows a plurality of elastics 316 oriented at about 45 degrees relative to the longitudinal axis 42 and the lateral axis 44. FIG. 12A is an alternate embodiment of FIG. 12, showing the plurality of elastics 316 oriented parallel with the longitudinal axis 42. FIG. 12B shows two layers of elastics 316 in the wings 120, both oriented parallel with the longitudinal axis 42, the lower layer of elastics 316 being spaced with gaps between groupings, and separated by a nonwoven wing layer 121. FIG. 12C is an alternate embodiment of FIG. 12B, where there is only one layer of elastics and no nonwoven wing layer 121. FIG. 12C also shows a plurality of elastics 316 oriented parallel with the longitudinal axis 42 between the topsheet 124 and secondary topsheet 124' (which may alternatively be oriented parallel with the lateral axis 44—not shown), and a plurality of elastics 316 oriented parallel with the longitudinal axis 42 between the backsheet film 126 and the backsheet nonwoven 127 (which may alternatively be oriented parallel with the lateral axis 44—not shown).

A portion or the entirety of the absorbent article 100 may be made to be laterally elastically extensible. The extensibility of the absorbent article 100 may be desirable in order to allow the absorbent article 100 to conform to a body of a wearer during movement by the wearer. The extensibility may also be desirable, for example, in order to allow the caregiver to extend the front waist region 36, the back waist region 38, the crotch region 37, and/or the chassis 200 to provide additional body coverage for wearers of differing size, i.e., to tailor the fit of the absorbent article 100 to the individual wearer and to aide in ease of application. Such extension may provide the absorbent article 100 with a generally hourglass shape, so long as the crotch region 37 is extended to a relatively lesser degree than the waist regions 36 and/or 38. This extension may also impart a tailored appearance to the absorbent article 100 during use.

Figure 9:
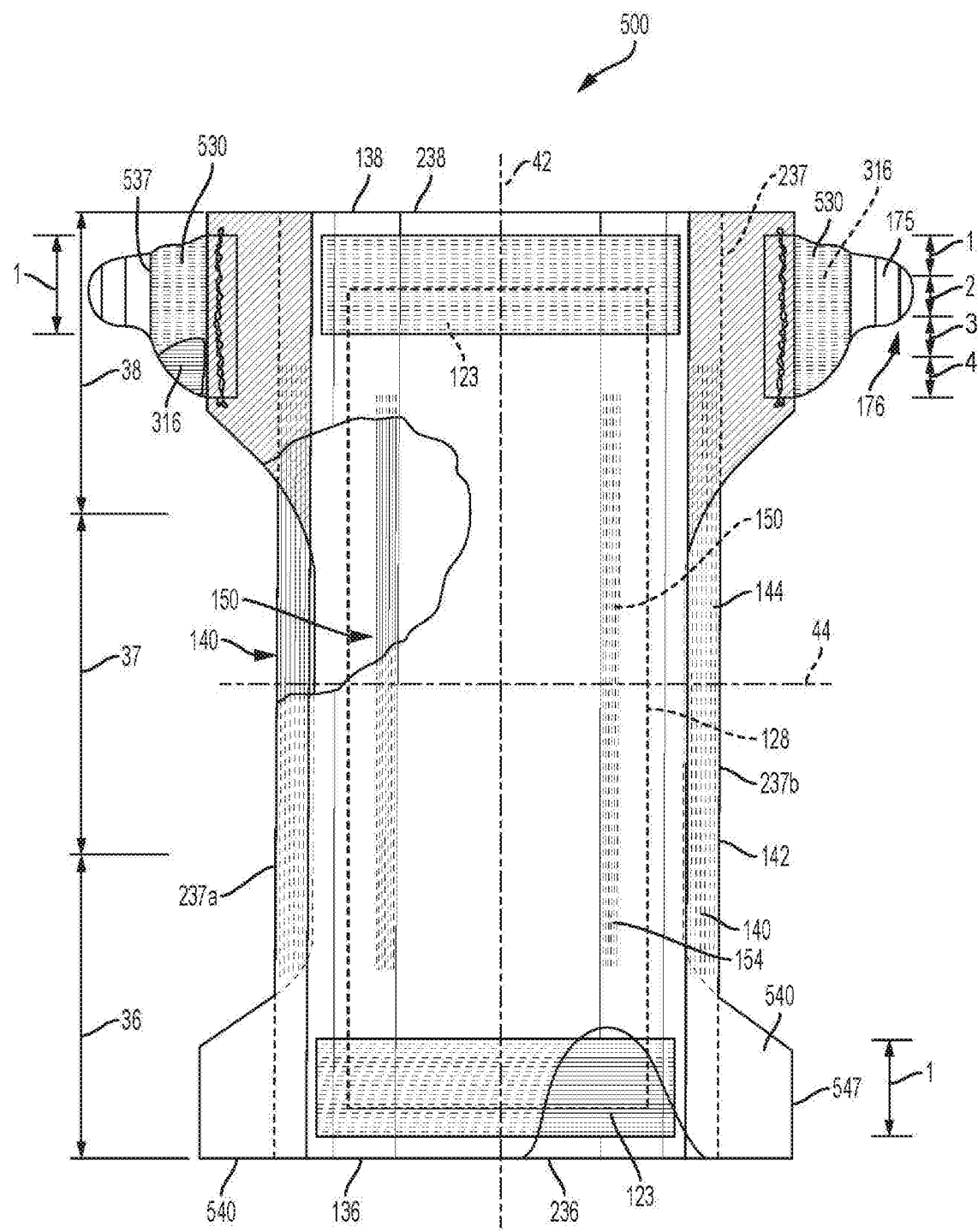
FIG. 9 is a plan view of a taped diaper including a pair of shaped discrete elastomeric ear panels 530 and a pair of non-elastomeric ear panels 540.
Figure 10:
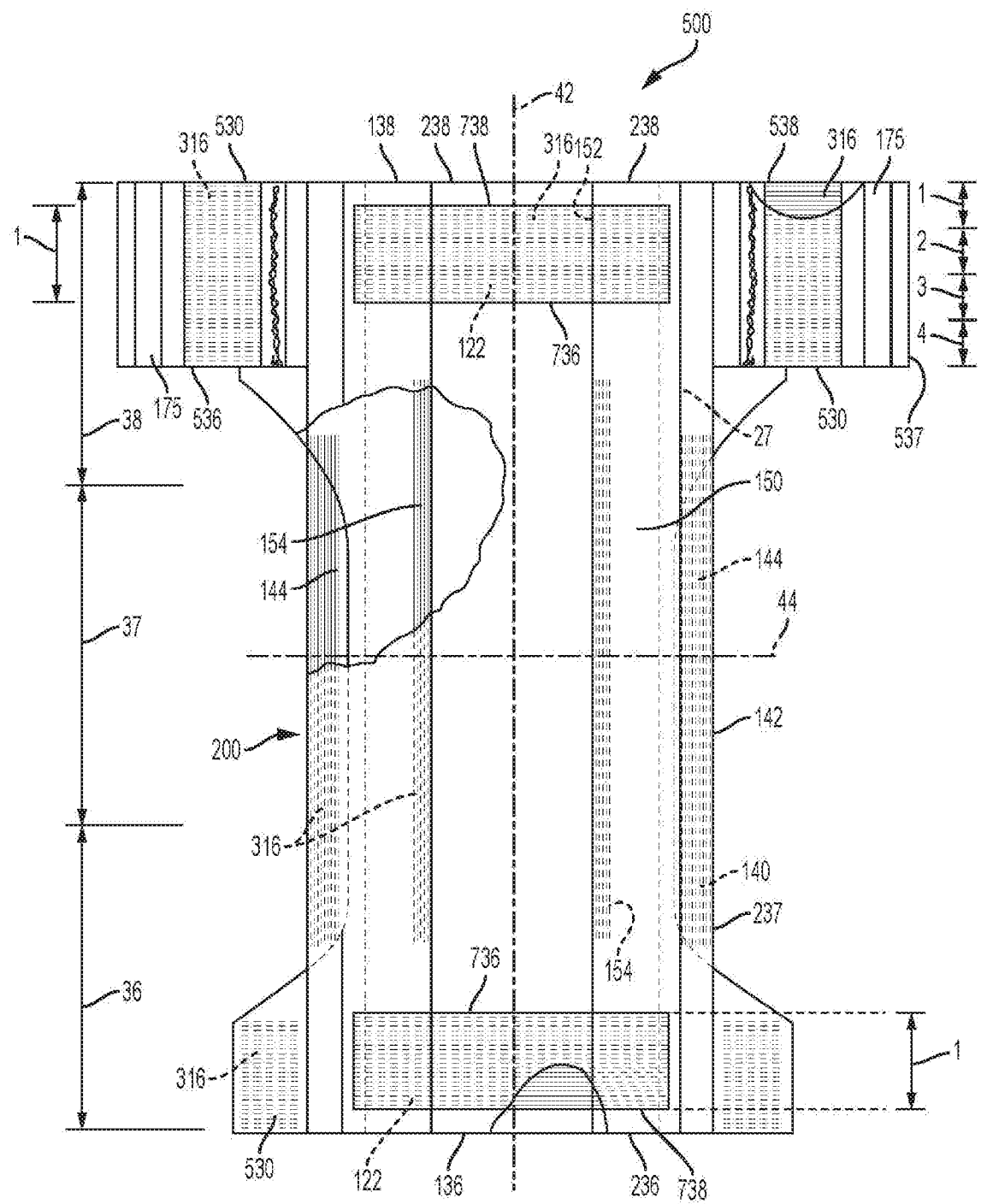
FIG. 10 is a plan view of a taped diaper including a pair of discrete elastomeric ear panels and a pair of non-elastomeric ear panels and a shaped backsheet.
Figure 11:
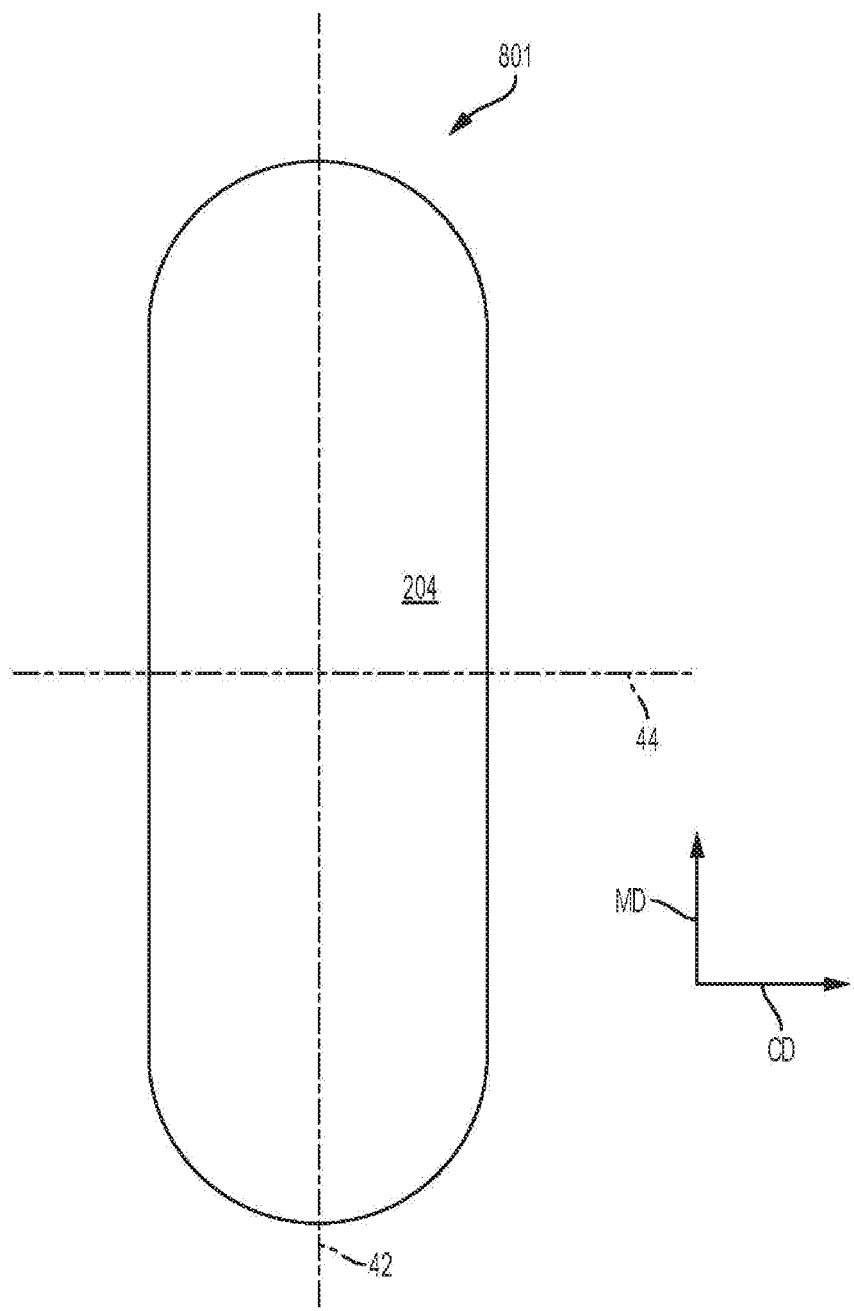
FIG. 11 is an exterior plan view of a feminine hygiene article 801, specifically a liner.
Figure 11A:
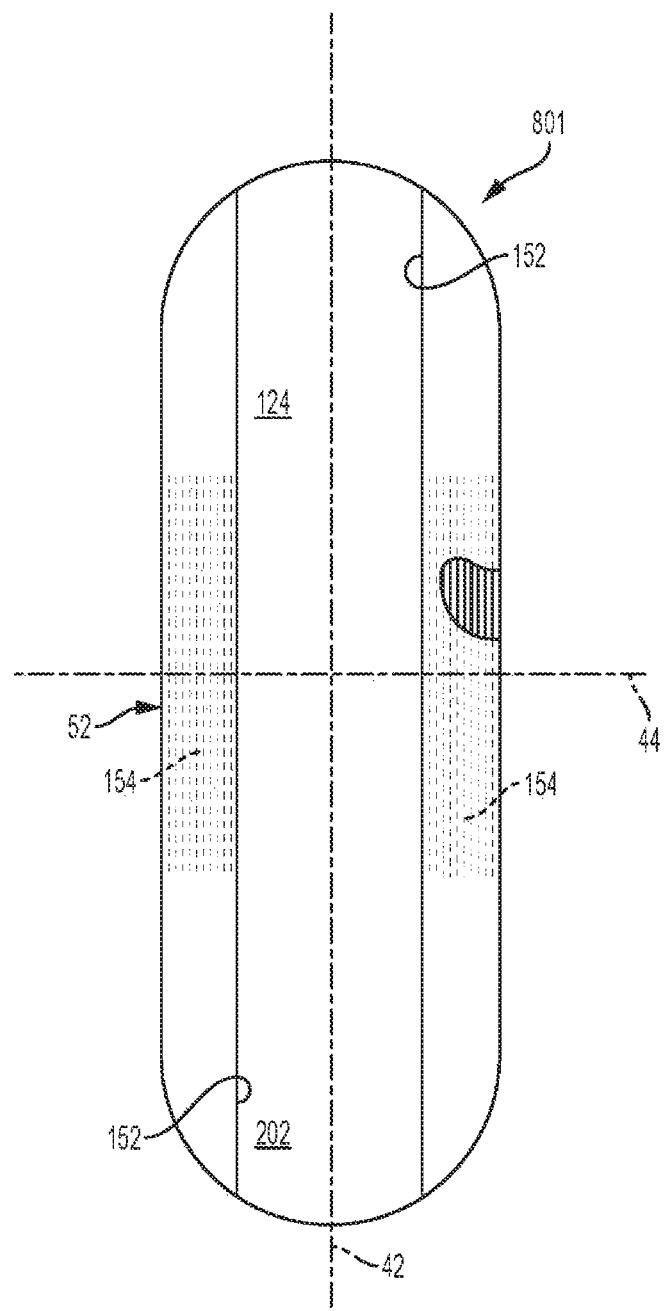
FIG. 11A is an interior plan view of the feminine hygiene article 801 of FIG. 11 illustrating leg longitudinal cuffs 52.
Figure 11B:
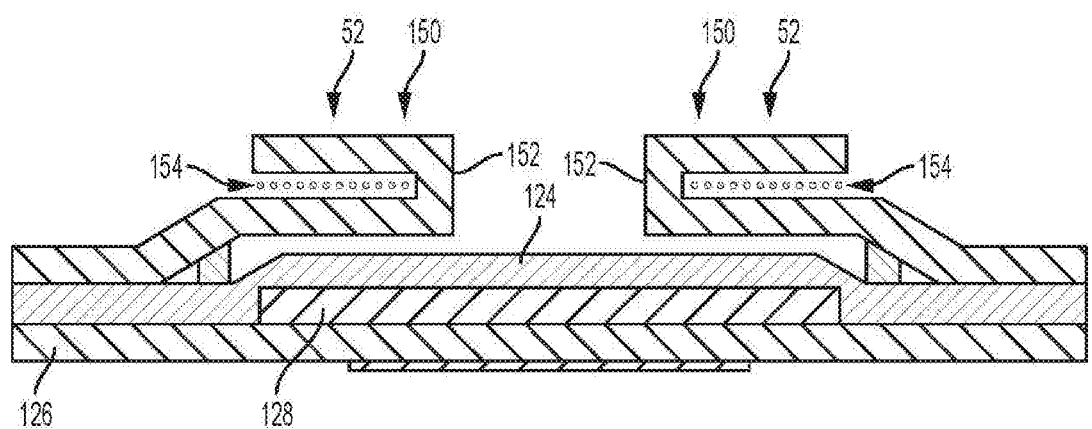
FIG. 11B is a cross section view of the feminine hygiene article 801, along the lateral axis 44 of the feminine hygiene article 801 of FIG. 9.

The chassis 200 may be substantially rectangular and may have discrete side panels 330 (FIG. 3B), extensible ear panels 530 (FIG. 9) and/or non-extensible ear panels 540 (FIG. 9) joined to the chassis 200 at or adjacent the chassis side edges 237 in one or both of the front waist region 36 and back waist region 38. Portions of one or more of the chassis side edges 237, the chassis front end edge 236 and the chassis back end edge 238 may be arcuate or curved either convexly or concavely as shown in FIGS. 11, 11A, and 10A. The chassis 200 may include integral side panels 330 (see FIG. 4), integral extensible ear panels (see FIG. 10), integral belts 430 (see FIG. 8) or integral non-extensible ear panels 540 formed by one or more of the outer cover nonwoven, backsheet film, outer leg cuff material, topsheet or core wrap 74 disposed in one or both of the front and back waist regions (FIG. 9). Alternatively, the chassis 200 may include discrete side panels 330 (see FIG. 3B), discrete extensible ear panels 530 (see FIGS. 9, 9A, and 10), or discrete belts 430 (FIGS. 5-7D). The chassis may be shaped or non-rectangular, in one waist region and substantially rectangular in the opposing waist region. Alternatively, the chassis may be substantially rectangular in one or both of the waist regions and non-rectangular in the crotch region.

An absorbent article may include a plurality of laterally extending elastics wherein the elastics are present in a first waist region, the crotch region and in the opposing second waist region.

Closed-Form Pant Article

Figure 4:
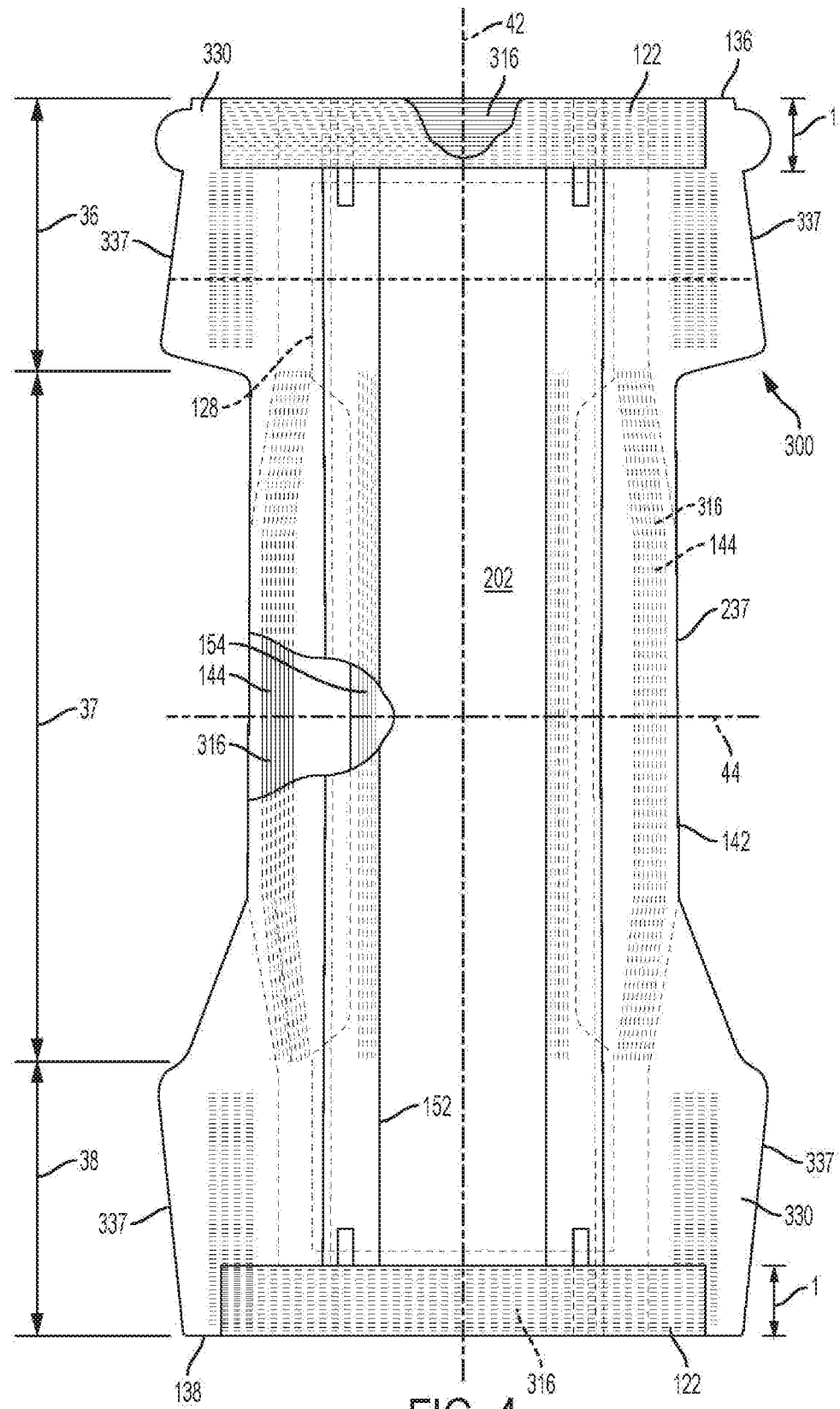
FIG. 4 is a plan view of a pant including integral side panels, prior to joining the side panels to form the waist and leg openings.
Figure 8:
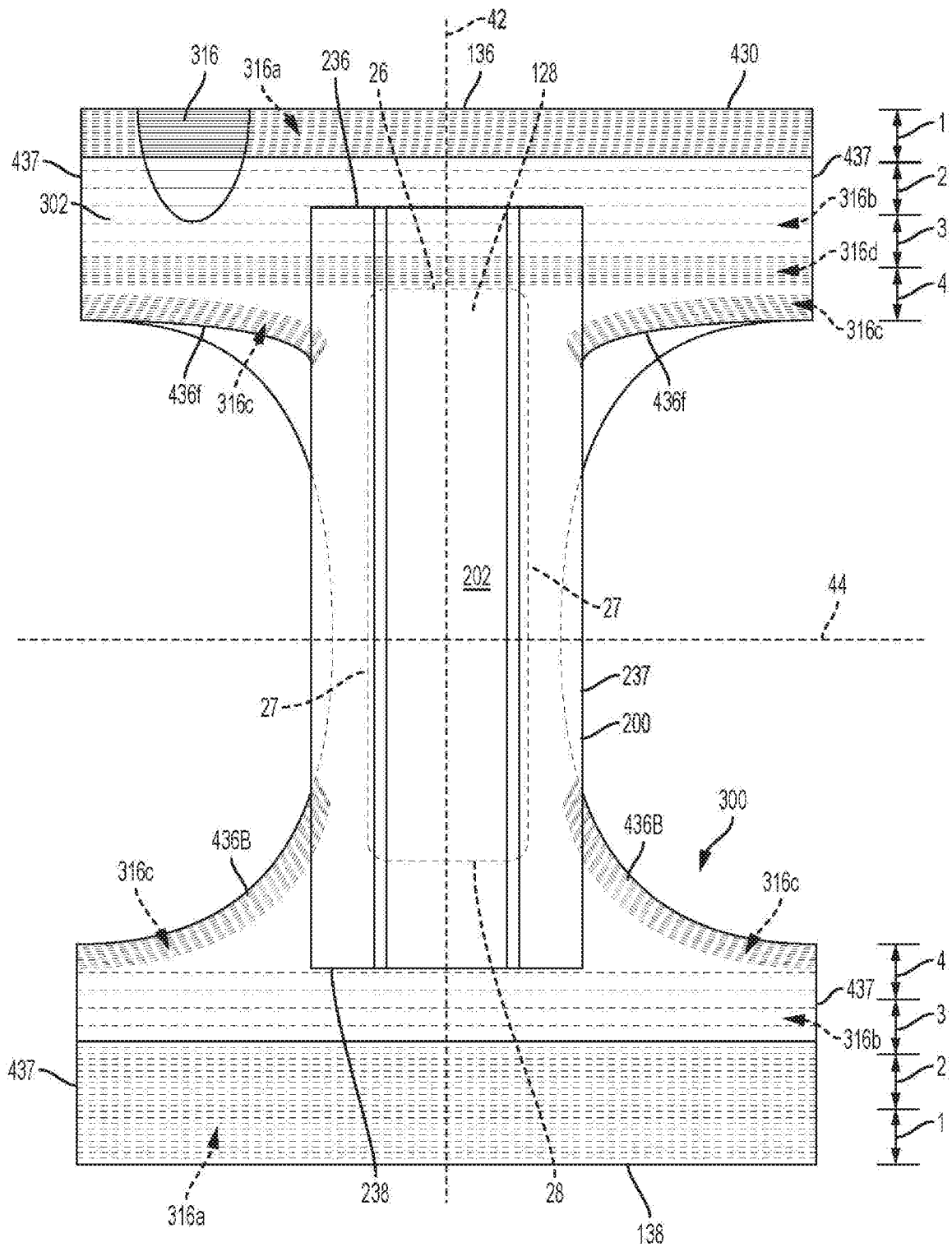
FIG. 8 is a plan view of a pant prior to joining side edges of the belts to form the waist and leg openings, illustrating multiple beamed elastic zones disposed in the low motion zones of a potential wearer.

Closed-form, pant-style, absorbent articles are generally disclosed in FIGS. 3-8, and are designed to be packaged in closed form having a waist opening 190 and two leg openings 192, and designed to be donned onto the wearer like a pair of durable underwear. The pant may include discrete elastomeric side panels 330 (FIG. 3B) and/or discrete belts 430 (FIG. 7) in one or both of the front waist region 36 and back waist region 38. Alternatively, the side panels 330 and/or belts 430 may be formed integrally with other elements of the article such as the chassis 200 (FIGS. 4 and 8).

Figure 5:
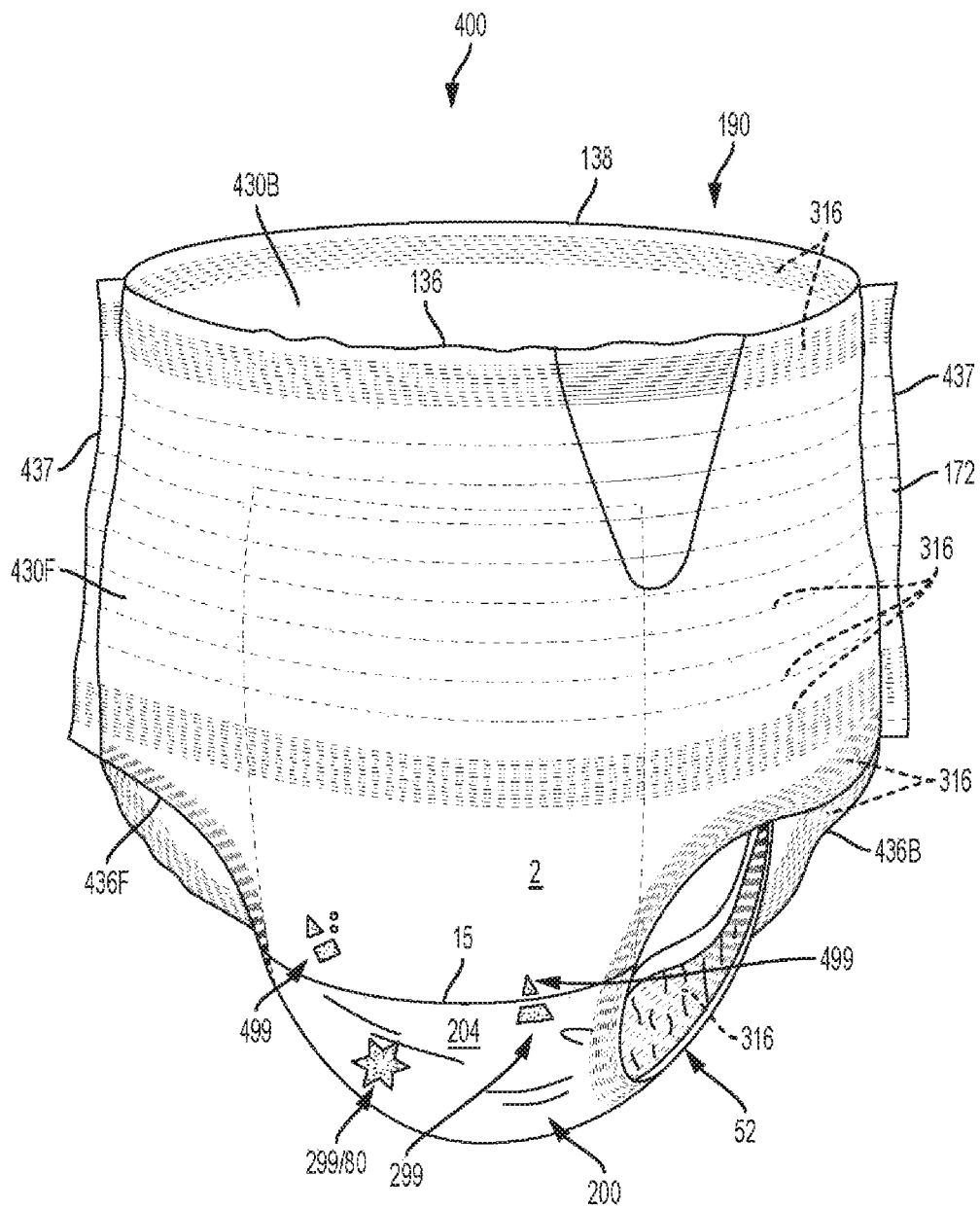
FIG. 5 is a perspective front view of a pant including belts including multiple elastics zones.
Figure 5A:
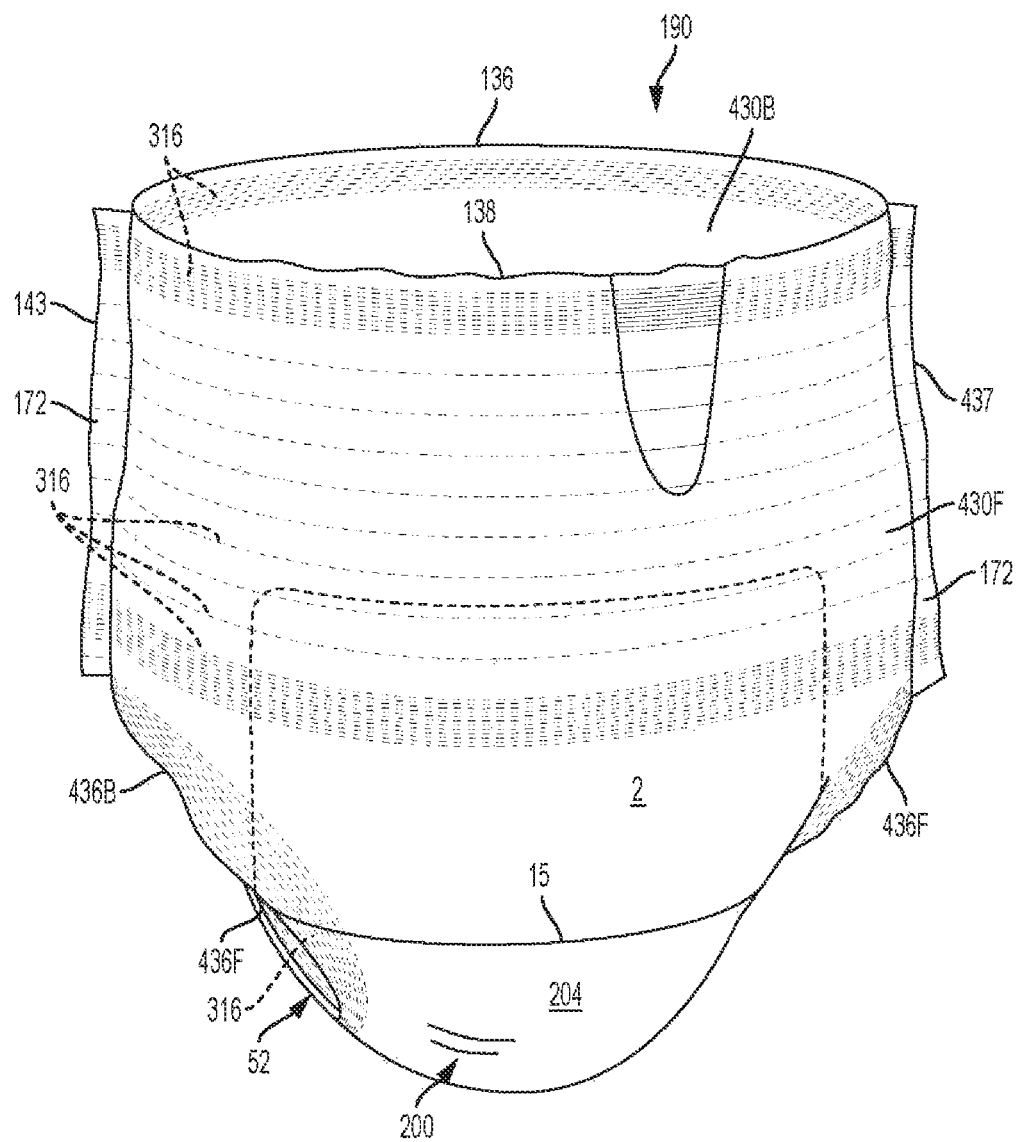
FIG. 5A is a perspective back view of the pant of FIG. 5
Figure 6:
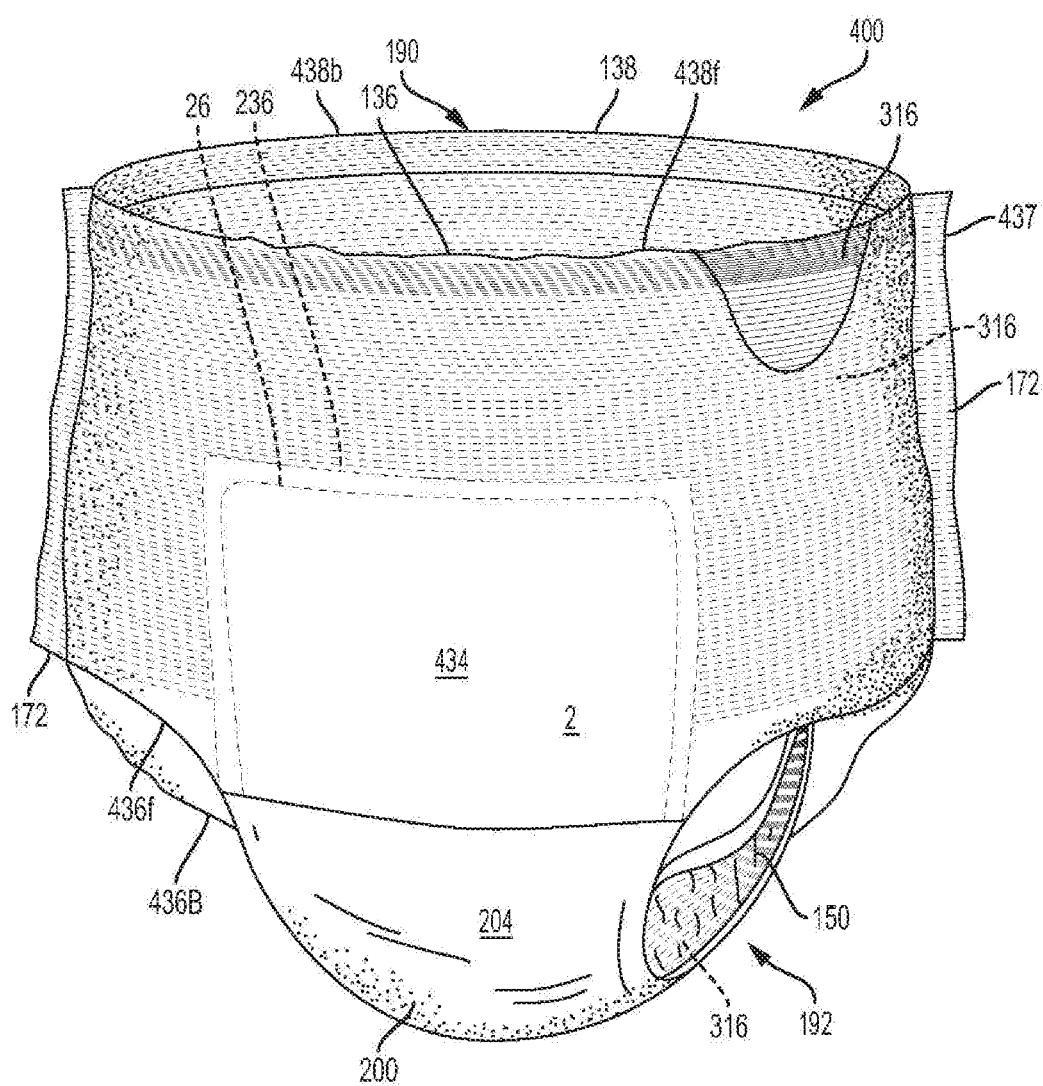
FIG. 6 is a perspective front view of a pant including discrete belts having both continuous and discontinuous elastics.

When the absorbent article includes front and back belts 430, the sides of front and back belts 430 may be joined permanently or refastenably to each other and the front and back side panels on one side of the article may be joined permanently or refastenably to each other to create a waist opening 190 and a pair of leg openings 192 (FIGS. 5, 5A, and 6). The belts 430 provide an elastically extensible feature that provides a more comfortable and contouring fit by initially conformably fitting the article 100 to the wearer and sustaining this fit throughout the time of wear well past when the pant has been loaded with exudates since the elastomeric side panels allow the sides of the pant to expand and contract. Further, the elastomeric belts 430 provide ease of application and develop and maintain wearing forces and tensions to maintain the article 100 on the wearer and enhance the fit, especially when beamed elastic laminates are used to form the belts 430. The elastomeric side panels enable ease of application allowing the pant to be pulled conformably over the hips of the wearer and positioned at the waist where the belts 430 conform to the body and provide tension sufficient to maintain the articles position on the wearer. The tension created by the belts 430 is transmitted from the elastic belts 430 along the waist opening 190 and along at least a portion of the leg opening 192. Typically, particularly regarding discrete side panels 330, the chassis 200 is disposed between the side panels 330 and extends to form a portion of the waist edge 136 and/or 138 of the pant including side panels 330. In other words, a portion of the waist edge 136 and/or 138 in one or both of the front waist region 36 and back waist region 38 may be formed in part by the side panels 330 and in part by the chassis 200.

The pant including side panels 330 may also include a pair of laterally opposing refastenable seams 174 as illustrated in FIGS. 3 and 3A. The refastenable side seam 174 may be formed by refastenably joining an interior surface of a portion of the article, e.g. a side panel 330, to an exterior surface of another portion of the article 100, e.g., a longitudinally opposing side panel 330 or the chassis 200 to form the refastenable side seam 174. FIG. 3A illustrates a front side panel 330f including a fastener 175 including hooks facing away from a wearer (the fastener 175 disposed on an exterior surface of the front side panel 330f) that refastenably attaches to a mating fastener 178 (loops or a suitable nonwoven in FIG. 3A), the mating fastener 178 being disposed on an interior surface of the back side panel 330b. Observe that that FIG. 3A is an alternative embodiment of FIGS. 3 and 3B as the pant of FIGS. 3 and 3B do not include a mating fastener 178—rather, the fastener 175 in FIGS. 3 and 3B refastenably join directly to the back side panels 330.

The pant including belts 430 may also include a first permanent side seam 172 and a laterally opposing second permanent side seam 172 as illustrated, for example, in FIGS. 5, 5A, and 6. The permanent side seam 172 may be formed by joining an interior surface of a portion of the article 100, e.g. a belt 430, to an exterior surface of another portion of the article 100, e.g. a longitudinally opposing belt 430 or the chassis 200 to form the permanent side seam 172. Alternatively, the permanent side seam 172 may be formed by joining an interior surface of a portion of the article 100, e.g. a belt 430, to an interior surface of another portion of the article 100, e.g. a longitudinally opposing belt 430 to form the permanent side seam 172. Any pants including side panels 330 configurations described above may include a waistband 122 wherein at least a portion of the waistband 122 (as illustrated in FIG. 3B) is disposed at or immediately adjacent the waist edge 136 and/or 138 and overlaps a portion of the center chassis 200. The waistband 122 may extend laterally to overlap portions of the inner barrier leg cuffs 150 and/or portions of the elastomeric side panels 330. The waistband 122 may be disposed on the interior surface 202 of the chassis 200 or alternatively between the topsheet 124 and the backsheet 125.

Particularly regarding belts 430, as illustrated in FIG. 7E, the inner belt layer 432 and/or the outer belt layer 434 of the first and second elastomeric belts 430 may be formed by a common belt layer as shown in FIG. 7E. When the first and second elastomeric belts 430 have a common belt layer, the common belt layer may extend from a first waist edge in a first waist region to a longitudinally opposing second waist edge in a second waist region, i.e. front waist edge 136 to back waist edge 138.

Also particularly regarding belted pants 400, as illustrated in FIGS. 7 and 7A, the belt pant 400 may have a first elastomeric belt 430 disposed in a first waist region having a first longitudinal length and a second elastomeric belt 430 disposed in a second waist region having a second longitudinal length wherein the longitudinal length of the first belt is greater than the longitudinal length of the second belt along the side edge of the belt at or adjacent the side seam. This length difference helps provide buttock coverage in the back of the pant providing a more underwear-like appearance. And, while this advantage is disclosed for belted pants 400, there is also an advantage in having longitudinally longer side panels 330 in the back waist region 38.

Open-Form Taped Article

Open-form, taped-style, absorbent articles are generally disclosed in FIGS. 9-10. The taped diaper 500, open-form article, as illustrated in FIGS. 9 and 10 may include elastomeric ear panels 530 in one or both of the front waist region 36 and back waist region 38. The elastomeric ear panels 530 may be unitary structurally with other elements of the article 100 or as a separate element joined to another element of the article 100. The elastomeric ear panels 530 provide an elastically extensible feature that provides a more comfortable and contouring fit by initially conformably fitting the article 100 to the wearer and sustaining this fit throughout the time of wear well past when the taped diaper 500 has been loaded with exudates since the elastomeric ear panels 530 allows the diaper to expand and contract to fit the wearer. Further, the elastomeric ear panels 530 develop and maintain wearing forces (tensions) and enhance the tensions developed and maintained by the fastening system 179 (including the fasteners 175 (e.g., hooks) that may be releasably engaged with a mating fasteners 178 (e.g., loops)), to maintain the article 100 on the wearer and enhance the fit. The elastomeric ear panels 530 especially assist in maintaining the primary line of tension formed by the fastening system 179 allowing the diaper to conformably fit over the hips of the wearer where there is dynamic motion, and initially pre-tensioning the waist opening 190 and leg opening 192 since the caregiver applying the diaper typically stretches the elastomeric ear panels 530 when applying the taped diaper 500 on the wearer so that when the elastomeric ear panels 530 contract, tension is transmitted from the elastomeric ear panels 530 along the waist opening 190 and along at least a portion of the leg opening 192. While the open-form article as contemplated herein may have the elastomeric ear panels 530 disposed in the back waist region 38, alternatively, the taped diaper 500 may be provided with elastomeric ear panels 530 disposed in the front waist region 36 or in both the front waist region 36 and the back waist region 38. The open-form article may also have elastomeric ear panels 530 disposed in a first waist region and elastomeric ear panels 530 or non-elastomeric ear panels 540 disposed in a second waist region.

In an alternative embodiment the open-form, taped-style, absorbent articles may include an elastomeric belt 430 disposed in one of the waist regions. The elastomeric belt 430 may be joined and/or positioned in a particular place or position and may be unitary structurally with other elements of the article 100 or as a separate element joined to another element of the article 100. A belted taped diaper the elastomeric belt 430 may be disposed in the back waist region 38. The elastomeric belt 430 may have fasteners disposed at or adjacent the laterally opposing ends of the belt. Fasteners 175 may be disposed on the interior surface of the belt 430 to engage with a discrete mating fastening component 178 or with the exterior surface 204 of the article (like the backsheet nonwoven 127) to fasten the article on the wearer.

Outer Cover Material

The backsheet 125 may include a backsheet film 126 and backsheet nonwoven 127. The backsheet nonwoven 127 may also be referred to as the outer cover material. The outer cover material forms at least a portion of the garment-facing surface of the absorbent article 100 and effectively "covers" the backsheet film 126 so that the film is not present on the garment-facing surface. The outer cover material may include a bond pattern, apertures, and/or three-dimensional features.

Absorbent Core

As used herein, the term "absorbent core" refers to the component of the absorbent article 100 having the most absorbent capacity and that includes an absorbent material. Referring to FIGS. 7, 7B, and 7C, in some instances, absorbent material (e.g., 51 and 53) may be positioned within a core bag or a core wrap 74. The absorbent material may be profiled or not profiled, depending on the specific absorbent article. The absorbent core 128 may include, consist essentially of, or consist of, a core wrap, absorbent material, and glue enclosed within the core wrap. The absorbent material may include superabsorbent polymers, a mixture of superabsorbent polymers and air felt, only air felt, and/or a foam. In some instances, the absorbent material may include at least 80%, at least 85%, at least 90%, at least 95%, at least 99%, or up to 100% superabsorbent polymers, by weight of the absorbent material. In such instances, the absorbent material may free of air felt, or at least mostly free of air felt—in such cases the AGM 51 may be held in place by an adhesive 54, such as a thermoplastic adhesive. And, for swim diapers, the article may be free of superabsorbent polymers. The absorbent core periphery, which may be the periphery of the core wrap, may define any suitable shape, such as rectangular, "T," "Y," "hour-glass," or "dog-bone" shaped, for example. An absorbent core periphery having a generally "dog bone" or "hour-glass" shape may taper along its width towards the crotch region 37 of the absorbent article 100.

Referring to FIGS. 7, 7B, and 7C, the absorbent core 128 may have areas having little or no absorbent material, where a wearer-facing surface of the core bag 74 may be joined to a garment-facing surface of the core bag 74. These areas having little or no absorbent material may be referred to as "channels" 129. These channels can embody any suitable shapes and any suitable number of channels may be provided. In other instances, the absorbent core may be embossed to create the impression of channels. The absorbent core in FIGS. 7, 7B, and 7C is merely an example absorbent core. Many other absorbent cores with or without channels are also contemplated herein.

As used herein, a loaded absorbent core is one holding (or capable of holding) a load of at least 50, 100, or 200 milliliters (mls) for diapers, pants, and adult incontinence articles. A disposable absorbent article contemplated herein and including an absorbent core may be designed to fit the wearer with an empty absorbent core (i.e., one that is not loaded), as well as being capable of fitting the wear for an appreciable time (2 or more hours) even when the core is loaded.

Acquisition Materials

One or more acquisition materials (e.g., 130) may be present at least partially intermediate the topsheet 124 and the absorbent core 128. The acquisition materials are typically hydrophilic materials that provide significant wicking of bodily exudates. These materials may draw liquid from the topsheet 124 and quickly move bodily exudates into the absorbent core 128. The acquisition materials 130 may include one or more nonwoven materials, foams, cellulosic materials, cross-linked cellulosic materials, air laid cellulosic nonwoven materials, spunlace materials, or combinations thereof, for example. In some instances, portions of the acquisition materials may extend through portions of the topsheet 124, portions of the topsheet 124 may extend through portions of the acquisition materials, and/or the topsheet 124 may be nested with the acquisition materials. Typically, an acquisition material or layer may have a width and length that are smaller than the width and length of the topsheet 124. The acquisition material may be a secondary topsheet in the feminine pad context. The acquisition material may have one or more channels as described in the absorbent core 128 section (including the embossed version). The channels in the acquisition material may align or not align with channels in the absorbent core 128. In an example, a first acquisition material may include a nonwoven material and as second acquisition material may include a cross-linked cellulosic material.

Landing Zone

Figure 9A:
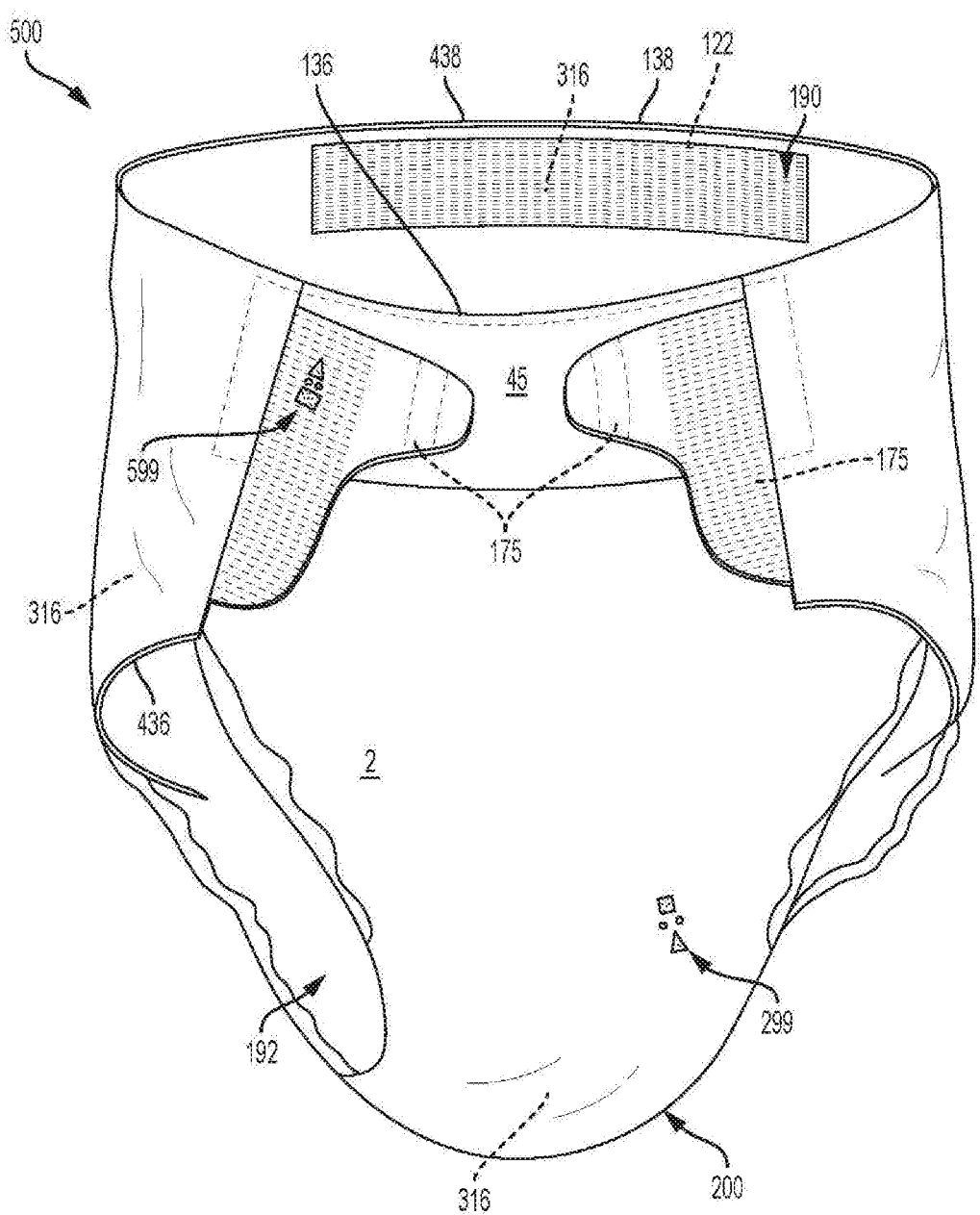
FIG. 9A is a perspective front view of the taped diaper of FIG. 9.

Referring to FIG. 9A, the absorbent article 100 may have a landing zone area 45 that is formed in a portion of the garment-facing surface 2 of the outer cover material. The landing zone area 45 may be in the back waist region 38 if the absorbent article 100 fastens from front to back or may be in the front waist region 36 if the absorbent article 100 fastens back to front. In some instances, the landing zone 45 may be or may include one or more discrete nonwoven materials that are attached to a portion of the outer cover material in the front waist region 36 or the back waist region 38 depending upon whether the absorbent article fastens in the front or the back. In essence, the landing zone 45 is configured to receive the fasteners 175 and may include, for example, a plurality of loops configured to be engaged with, a plurality of hooks on the fasteners 175, or vice versa.

Wetness Indicator/Graphics

Absorbent articles 100 as contemplated herein may include graphics (e.g., a chassis graphic 299, a side panel graphic 399, a belt graphic 499, or an ear panel graphic 599) and/or wetness indicators 80 that are visible from the garment-facing surface 2. The graphics may be printed on the landing zone 45, the backsheet 125, topsheet 124, belts 430, side panels 330, ear panels 530 and/or at other locations. The wetness indicators are typically applied to the absorbent core facing side of the backsheet film 126, so that they can be contacted by bodily exudates within the absorbent core 128. In some instances, the wetness indicators may form portions of the graphics e.g., 299. For example, a wetness indicator may appear or disappear and create/remove a character within some graphics. In other instances, the wetness indicators 80 may coordinate (e.g., same design, same pattern, same color) or not coordinate with the graphics. Alternatively, graphics and/or wetness indicators 80 may be disposed on, and/or visible from, the wearer-facing surface 204.

One or more of the side/ear panels 330, 530 may include a graphic disposed thereon. One or more of the elastomeric side/ear panels 330, 530 include a graphic (e.g., 399, 599) substantially aligned to a chassis graphic 299 to form a composite graphic element. Further, the front and back belts 430f and 430b may include graphics. The graphics may extend substantially around the entire circumference of the absorbent article 100 and may be disposed across side seams 172 and/or across proximal front and back belt edges 15 (see FIG. 5); or, alternatively, adjacent to the seams in the manner described in U.S. Pat. No. 9,498,389 to create a more underwear-like article. The graphics may also be discontinuous.

Topsheets

An absorbent article 100 as contemplated herein may include a topsheet 124. The topsheet 124 is the part of the absorbent article 100 that is in contact with the wearer's skin. The topsheet 124 may be joined to portions of the backsheet 125, the absorbent core 128, the leg longitudinal cuffs 52, and/or any other layers as is known to those of ordinary skill in the art. The topsheet 124 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Backsheets

An absorbent article 100 as contemplated may include a backsheet 125. The backsheet 125 is generally that portion of the absorbent article 100 positioned proximate to the garment-facing surface of the absorbent core 128. The backsheet 125 may be joined to portions of the topsheet 124, the backsheet nonwoven 127, the absorbent core 128, and/or any other layers of the absorbent article by any attachment methods known to those of skill in the art. The backsheet film 126 prevents, or at least inhibits, the bodily exudates absorbed and contained in the absorbent core 128 from soiling articles such as bedsheets, undergarments, and/or clothing. The backsheet is typically liquid impermeable, or at least substantially liquid impermeable. The backsheet may, for example, be or include a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Longitudinal Cuffs

An absorbent article 100 may include longitudinal cuffs 52, which may include inner barrier leg cuffs 150 and outer leg cuffs 140. The inner barrier leg cuffs 150 may be positioned laterally inboard of outer leg cuffs 140. Each of the longitudinal cuffs 52 may be formed of one or more sections of web material bonded to other components of absorbent article 100, so it can extend upward or outward from a wearer-facing surface of the absorbent article 100 and provide improved containment of body exudates, approximately at the junction of the torso and legs of the wearer. Each of the inner barrier leg cuffs 150 are delimited by a base portion 152 joined directly or indirectly to (or formed by extensions of) the topsheet and/or the backsheet and a barrier cuff free edge, which is adapted to contact with the wearer's skin so as to provide a gasketing function to contain liquid exudates within the article. The inner barrier leg cuffs 150 may extend longitudinally at least partially (or fully) between the front end edge 136 and the back end edge 138 of the absorbent article 100 on opposite sides of the chassis and may be at least present in the crotch region 37. The inner barrier leg cuffs 150 may each include one or more elastics 316 (e.g., elastic strands or strips) near or at the free terminal edge. These elastics 316 cause the inner barrier leg cuffs 150 to help form a gasketing structure about the legs and/or torso of a wearer. The outer leg cuffs 140 extend at least partially (or fully) between the front end edge 136 and the back end edge 138. The outer leg cuffs 140 may be adapted to cause portions of the absorbent article 100 proximate to the chassis side edges 237a and 237b to help form a gasketing structure about the legs of the wearer. The outer leg cuffs 140 may extend at least within the crotch region 37.

Longitudinal cuffs of currently available articles are typically elasticized by from 1 to 5 elastic strands of a dtex of from 470 to 940 or higher, incorporated into the structure at a pre-strain greater than 150%, often substantially greater. At these typical combinations of values, the non-elastic web material components of cuff structures form ruffles or gathers (also sometimes called "rugosities" or "corrugations"), of web material affixed to the strands, that are of a substantially low frequency (along the cross direction of formation of the cuff structures) and substantially high z-direction amplitude or height, such that they are highly visible and impart a rough, even ragged appearance to the cuff structures. Further, as the material ruffles are pressed against the wearer's skin by tensile forces in the elastic strands, they subject the skin to uneven distributions of pressure beneath the elastic strands, with pressure points at the inward-facing ruffles, which can promote undesirable skin marking and even skin irritation. Even further, the ruffles can present gaps between the cuff structure and the wearer's skin, through which liquid (such as urine) can pass and thereby escape the article.

It has been learned that substituting beamed elastic strands as the elasticizing element of an elasticized cuff enables, as discussed elsewhere herein, inclusion of a substantially greater number of finer elastic strands per unit cross-direction width to form a band-like skin-contacting portion of a cuff, with dramatically smaller ruffles of substantially higher machine direction frequency and lower z-direction amplitude, than is practically available using non-beamed elastic strand technology. Use of a warp beam as a supply mechanism for supplying elastic strands to a stretch laminate manufacturing process enables provision of a plurality of beamed elastic strands, to the cuff structure, that are comparatively substantially higher in number and substantially closer in spacing. Beamed elastic strands can be selected for this purpose to be substantially lower in decitex and lower in pre-strain, than those in a cuff structure exhibiting similar cumulative tensile, expansion and contraction characteristics, formed using conventional elastic strand technology.

Referring to FIGS. 3, 3B, 2A-2E, 2I and 2J, an absorbent article may include a pair of longitudinal barrier cuffs 150. Barrier cuffs are also known sometimes as "gasketing cuffs" or "standing cuffs." The latter designation results from the tendency of the elasticized structure to "stand" or extend away from the other wearer-facing surfaces of the article (such as the topsheet) as a result of longitudinal tension in the pre-strained elastic strands 154 proximate barrier cuff free edge 153 which draw the cuff upward toward the wearer when the article is wrapped about and through the wearer's crotch area.

As illustrated in FIG. 1, longitudinal tension LT within an elastic strand in a barrier cuff structure results in normal force NF along the length of the strand, directed toward the wearer's body WB, when the article is worn. This normal force may manifest itself in pressure against the wearer's skin, localized along the length of each strand. The pressure may be even further localized where gathers or ruffles in the cuff material, caused by contraction of the strands, extend and protrude toward the wearer. When a relatively lower number of strands of a decitex and pre-strain level selected to provide suitable tension are present, skin marking and even irritation about the wearer-contacting portions of the cuff structure may be more likely.

For purposes contemplated herein, barrier cuff 150 may have a base portion 152 affixed to other components of the article such as topsheet 124, and a barrier cuff free edge 153. Barrier cuff free edge 153, or barrier cuff free edge 153 along with an elasticized band 156 of material proximate edge 153, may be present. Longitudinally-oriented barrier cuff elastic strands 154 may be included to form elasticized band 156. In some examples, barrier cuff elastic strands 154 may be beamed elastic strands, and thereby may be incorporated at a Manufacturing Strand Spacing no more than 2.0 mm, 1.5 mm, 1.0 mm, 0.8 mm, 0.50 mm, or even no more than 0.25 mm. In some examples, barrier cuff elastic strands 154 may be beamed elastic strands, and thereby may be disposed so as to result in an Average-Strand-Spacing no more than 2.0 mm, 1.5 mm, 1.0 mm, 0.8 mm, 0.50 mm, or even no more than 0.25 mm.

Strands 154 may be formed of elastomeric material such as Spandex and similar materials disclosed herein. In order to provide a total tensile force in the band, suitable for providing a gasketing function while not exerting an uncomfortable amount of pressure against the wearer's skin, and also to preserve spacing between the strands to maintain breathability, the strands may be selected to have a Manufacturing Decitex and/or to result in an Average Decitex no greater than 400, more preferably no greater than 300, 200, 150, or most preferably no greater than 100.

In combination with relatively close spacing and low decitex, it may be desired to impart the strands with a Manufacturing Pre-Strain, during their incorporation into the cuff structure, no greater than 300%, 200%, 150%, 100% or even no greater than 75%; or alternatively, to impart the strands with an amount of pre-strain that results in a laminate with an Average-Pre-Strain within these ranges. Finally, to balance a suitable amount of total tensile force in the band as a whole, with the relatively lowered values of decitex, strand spacing and pre-strain identified, it may be desired that the elasticized band have a width BW of 5 mm to 30 mm, more preferably 10 mm to 25 mm, and even more preferably 15 mm to 20 mm. For purposes of the description of cuff structures herein, an elasticized "band" is characterized by the presence of a plurality of longitudinally-oriented, laterally-spaced elastic strands of the same decitex, spacing, and pre-strain level, and the width of a band is measured from the outside of the first strand in the plurality to the outside of the last strand in the plurality.

With appropriate selection of beamed elastic strand spacing and decitex, and amount of pre-strain imparted to the strands as they are incorporated in to the cuff structure, a cuff structure having longitudinal tension within an elasticized band suitable, and comparable to, that in conventional barrier cuff structures can provide for substantially fewer pressure points or localizations, i.e., evenly distributed, pressure against the wearer's skin, resulting in substantially reduced possibility for skin marking and greater wearer comfort. Additionally, combinations of comparatively and appropriately selected reduced spacing, reduced decitex and reduced pre-strain discussed herein causes ruffles of gathered cuff material that are comparatively much smaller in size (i.e., greater machine direction frequency, lesser z-direction amplitude) than the ruffles in conventional cuff structures. As a result, the cuff structures can lay against the wearer's skin more closely, with fewer and smaller gaps between ruffles. In summary, the formation of an elasticized band in a cuff structure by inclusion of a plurality of relatively closely-spaced, low decitex, low pre-strain beamed elastic strands in a stretch laminate structure provides a greater and more even area of contact between the band and the wearer's skin, with lower average and lower maximum pressure against the skin—than a conventionally manufactured cuff structure having similar total longitudinal tensile force characteristics. This provides for improved gasketing to retain liquids within the absorbent article, and greater wearer comfort.

Strands 154 may be directly or indirectly joined to a layer of web material forming barrier cuff wall 157. Barrier cuff wall 157 may form, and may extend from, barrier cuff base portion 152, to barrier cuff free edge 153. Barrier cuff wall 157 may be formed of any web material having suitably comfortable softness and pliability, and preferably, is resistant to passage of liquid therethrough, absent a forcing pressure, to provide the barrier cuff 150 with liquid containment capability. In some examples, barrier cuff wall 157 may be formed of a nonwoven web material that includes a distribution of fine fibers, such as meltblown fibers or nanofibers. A dense distribution of fine fibers spun from a hydrophobic material, or material treated to be hydrophobic, can impart the web with resistance to passage of aqueous liquid therethrough, while retaining vapor permeability/breathability of the material through spaces between the fiber components, which can help the article vent humid air in the region between the article and the wearer's skin, and thereby improve wearer comfort and skin health. Accordingly, in some examples the material used to form barrier cuff wall 157 may be a spunbond-meltblown-spunbond (SMS) material, a spunbond-meltblown-nanofiber-spunbond material (SMNS) or any other web material having a layer of, or combination of consolidated layers of, fibers including meltblown fibers and/or nanofibers.

As may be appreciated from the figures, strands 154 may be disposed or sandwiched between material forming the barrier cuff wall 157 and a second layer 158 of barrier cuff wall 157. Similar to the material forming barrier cuff wall 157, second layer 158 may be formed of any web material having suitably comfortable softness and pliability. In some examples, second layer 158 may be formed of a nonwoven web material, which may or may not be selected to be resistant to the passage of liquid therethrough. In some examples second layer 158 may be a conventional spunbond nonwoven web material. In other examples, second layer 158 may also be formed of a nonwoven web material that includes a distribution of fine fibers, such as meltblown fibers or nanofibers, and may be formed of the same material as that used to form barrier wall 157. In some examples, second layer 158 is formed of an extended portion of the same material forming barrier wall 157, folded over to enclose or envelope strands 154 as suggested in FIGS. 2A-2E. Such a folded-over configuration may be useful for providing assurance that strands 154 cannot escape the cuff structure in the event they become dislodged from their affixed positions within the structure. In this configuration, it may be desired that the edge strand (i.e., the strand closest the barrier cuff free edge 153) be as close to the barrier cuff free edge 153 as can be achieved. This helps assure that ruffles or gathers in the barrier cuff wall and second layer material(s), at the folded barrier cuff free edge 153, formed by contraction of the strands 154 from their pre-strained condition, are as small as possible. Thus, it may be desired that the outer surface of the edge strand be spaced no more, along the active (pre-strained) length of the strand, than 3.0 mm, more preferably no more than 2.0 mm, even more preferably no more than 1.5 mm and still more preferably no more than 1.0 or even 0.8 mm from the outside of barrier cuff free edge 153.

It may be desired that the material(s) forming barrier cuff wall 157 and/or second layer 158 be selected to as to be of low enough caliper and substantial enough pliability (which affect bending stiffness) such that they can easily flex and form the comparatively fine, high-frequency, low amplitude ruffles or gathers contemplated herein, made possible by beamed elastics used to form elasticized bands as described herein. Accordingly, it may be desired that the materials(s) used to form one or both of barrier cuff wall 157 and second layer 158 have a basis weight no greater than 25 gsm, more preferably no greater than 20 gsm, and even more preferably no greater than 15 gsm, or when barrier cuff wall 157 and second layer 158 are combined in a laminate, that they have a combined basis weight no greater than 50 gsm, more preferably no greater than 40 gsm, and even more preferably no greater than 30 gsm. (Herein, "gsm" means grams of material per square meter. For a nonwoven web material, its basis weight is expressed in gsm. For an added material such as adhesive applied to a nonwoven web material, the quantity applied is expressed in gsm, meaning grams of added material applied per square meter of the web material.)

The material forming barrier cuff wall 157 and second layer 158 may be bonded together to form a laminate structure about strands 154 by any suitable mechanism. In some examples, these layers may be bonded together by applying adhesive to the strand-facing surface of one or both layers, and then bringing the layers together about or sandwiching the strands 154, in the nip between a pair of rollers, to form a laminate structure. Adhesive may be applied in any suitable quantity sufficient to hold the laminate structure together, but it may be desired to avoid application of adhesive to an extent that it significantly compromises elastic contractibility of the beamed elastic strands 154 and of the laminate structure. Accordingly, it may be desired that adhesive holding the laminate structure together be applied to a basis weight of 1.5 to 5.0 gsm, or 2.0 to 4.0 gsm, or even 2.5 to 3.5 gsm. Adhesive may be applied to one or both of the material forming the barrier wall and the second layer by any suitable method, such as by a slot coating process. The adhesive may be any adhesive formulation having elastic properties and deemed suitable for assembly of components of wearable absorbent articles, such as any hot melt adhesive known for use in the manufacture of disposable diapers.

Alternatively, or in addition, the material forming barrier cuff wall 157 and second layer 158 may be bonded together to form a laminate structure about strands 154 by a pattern of mechanical bonds. Herein, "mechanical bonds" are bonds formed by application of pressure with or without heat or heating energy applied, in which bonds are formed between the material layers by deformation and in some examples fusing of components of the respective layers together. In some examples, the material forming barrier cuff wall 157 and second layer 158 may be bonded together to form a laminate structure by methods described in U.S. application Ser. No. 15/832,929 or U.S. application Ser. No. 15/833,057.

In some examples, a folded-over portion of the material forming barrier cuff wall 157 and thereby forming second layer 158 may be bonded together by a line or pattern of mechanical bonds at cuff bonds 159, disposed proximate an end edge of the cuff material, to form a closed, enveloping laminate structure about strands 154—as suggested in FIGS. 2A-2E.

As reflected in FIGS. 2A-2E, 2I and 2J, barrier cuff wall 157 and/or base portion of barrier cuff 150 may be affixed to the other components of the article along a longitudinal cuff bond 155. Longitudinal cuff bond 155 may be formed between the material forming barrier cuff wall 157 and/or base portion of barrier cuff 150, and underlying materials, which may include topsheet 124 and backsheet 128 or components thereof. In some examples, longitudinal cuff bond 155 may be formed by a longitudinally-extending mechanical bond or series of mechanical bonds. In addition, or alternatively, longitudinal cuff bond 155 may be formed by one or more longitudinally-oriented deposit(s) of adhesive amongst these layers. In some examples adhesive may be preferred alone, or to supplement mechanical bonding, to provide a liquid seal at the base of the base portion of barrier cuff 150, reaching down through the porous web materials to the liquid-impermeable component of the backsheet 125, for liquid containment purposes.

A plurality of longitudinally-extending, laterally spaced elastic strands such as strands 154, when laminated between two layers and closely spaced together as described herein, results in a band portion 156 that will have greater lateral bending stiffness than regions of cuff 150 below/without elastic strands. As a result, formation of an elasticized band 156 as described herein may result in a barrier cuff 150 structure that tends to hinge or bend along a longitudinal bend line 149 proximate the first strand of the band (see FIG. 2I). Thus, the structure described herein provides for an elasticized band portion 156 of a barrier cuff 150 that will lie flat against the wearer's skin—enhancing the effect of dispersing and evenly distributing pressure, enhancing wearer comfort, and enhancing gasketing performance.

Figure 2A:
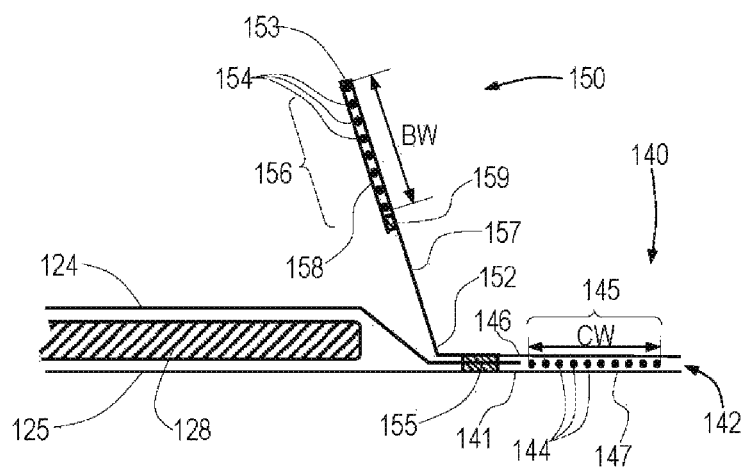
FIGS. 2A-2J are schematic lateral cross sections of various examples of cuff structures that may be included with a disposable absorbent article such as depicted in FIG. 3B, taken along line 2-2 in FIG. 3B.
Figure 2B:
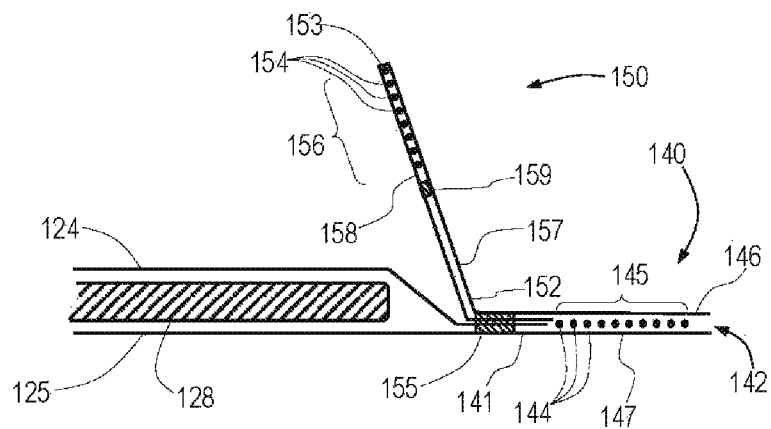
Figure 2C:
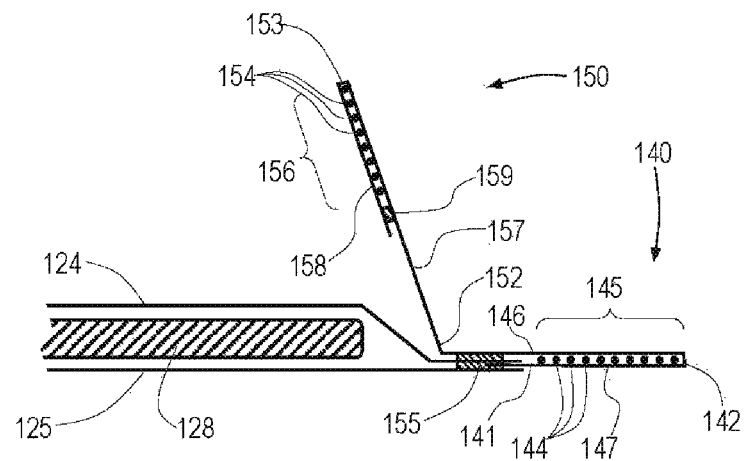
Figure 2D:
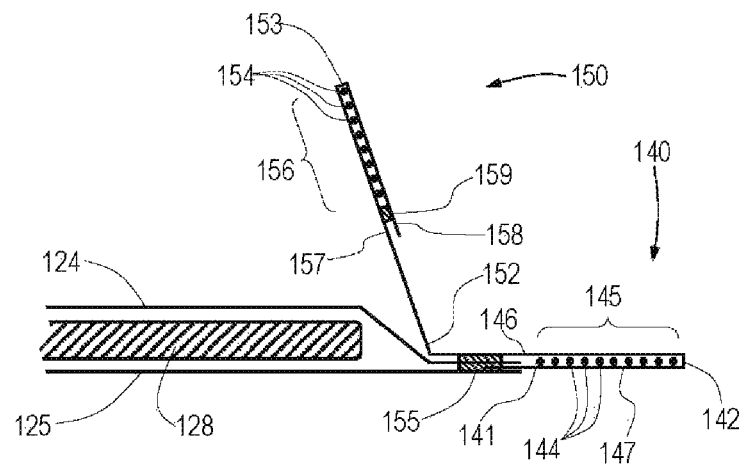
Figure 2E:
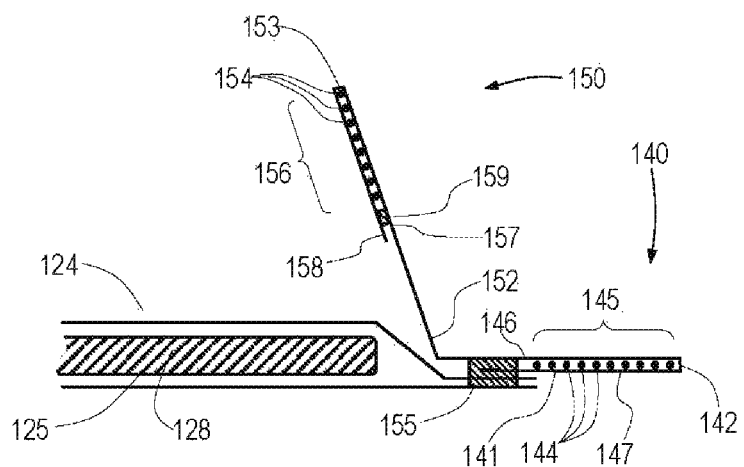
Figure 2F:
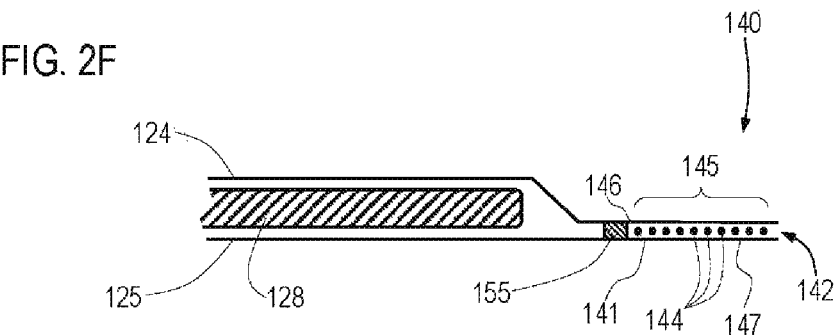
Figure 2G:
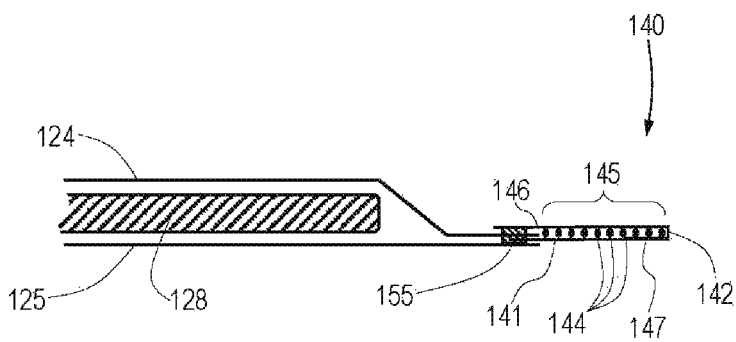
Figure 2H:
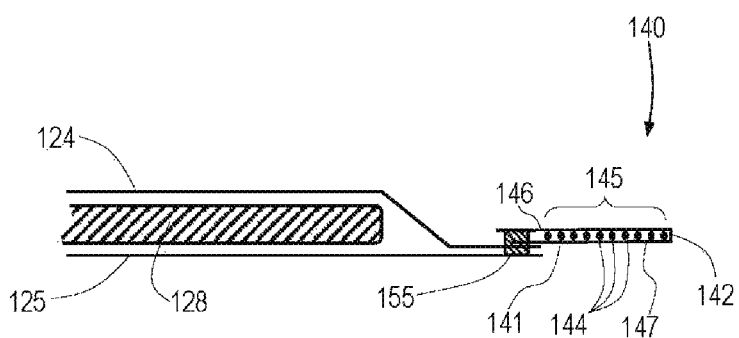
Figure 2I:
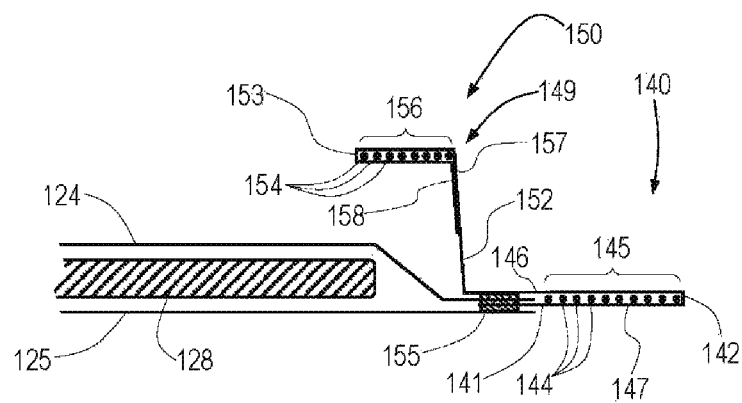
Figure 2J:
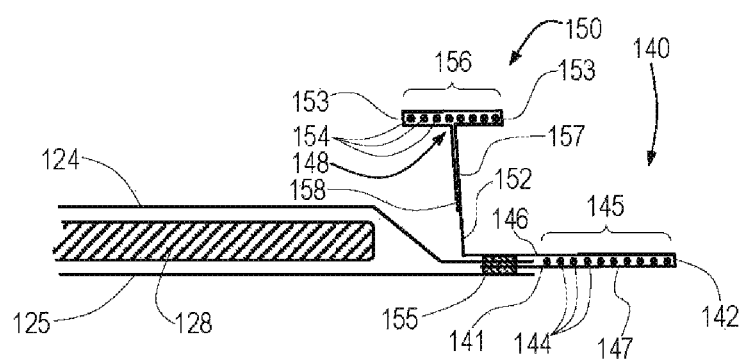

In another example reflected in FIG. 2J a barrier cuff 150 may be formed in a T-structure wherein barrier cuff wall 157 meets elasticized band portion 156 at a lateral midpoint, or some other intersecting location 148 disposed between the outermost two of elastic strands 154 defining either side or longitudinal edge of the elasticized band 156. A T-structure as depicted may be desired in some examples because it may more securely lay flat against the wearer's skin, being less vulnerable to be being pulled away from the skin along one side or the other, as in other possible barrier cuff structures in which barrier cuff wall 157 meets elasticized band portion 156 at one side or longitudinal edge or the other of the band 156 as, for example, reflected in FIG. 2I.

Referring to FIGS. 3, 3B and 2A-2J, an absorbent article may include a pair of outer leg cuffs 140 to provide containment gasketing and/or close and neat fit of the article about the wearer's legs. Longitudinal tension within an elastic outer leg cuff strand 144 in a barrier cuff structure results in normal force along the length of the strand, against the wearer's body, when the article is worn. This normal force is manifest in pressure against the wearer's skin, localized along the length of each strand where it lies proximate a leg. The pressure may be even further localized about gathers or ruffles in the cuff material, protruding toward the wearer and caused by contraction of the strands. When a relatively lower number of strands of a suitable decitex and pre-strain level are present, skin marking and even irritation about the wearer-contacting portions of the cuff structure may be more likely.

For purposes contemplated herein, leg cuff 140 may have a proximal portion 141 affixed to or extending laterally from other components of the article such as topsheet 124 and/or backsheet 125, and a free distal edge 142. Free distal edge 142, or free distal edge 142 along with an elasticized band 145 of material proximate edge 142, may be present. Generally longitudinally-oriented outer leg cuff elastic strands 144 may be included to form elasticized band 145.

In some examples, outer leg cuff elastic strands 144 may be beamed elastic strands, and thereby may be incorporated at a Manufacturing Strand Spacing no more than 2.0 mm, 1.5 mm, 1.0 mm, 0.8 mm, 0.50 mm, or even no more than 0.25 mm. In some examples, outer leg cuff elastic strands 144 may be beamed elastic strands, and thereby may be disposed so as to result in an Average-Strand-Spacing no more than 2.0 mm, 1.5 mm, 1.0 mm, 0.8 mm, 0.50 mm, or even no more than 0.25 mm.

Strands 144 may be formed of elastomeric material such as Spandex and similar materials as disclosed herein. In order to collectively provide a total tensile force in the band, suitable for providing a gasketing function while not exerting an uncomfortable amount of pressure against the wearer's skin, and also to preserve spacing between the strands to maintain breathability, the strands may be selected to have a Manufacturing Decitex and/or to result in an Average Decitex no greater than 400, more preferably no greater than 300, 200, 150, or most preferably no greater than 100.

In combination with relatively close spacing and low decitex, it may be desired to impart the strands with a Manufacturing Pre-Strain, during their incorporation into the cuff structure, no greater than 300%, 200%, 150%, 100% or even no greater than 75%; or alternatively, to impart the strands with an amount of pre-strain that results in a laminate with an Average-Pre-Strain within these ranges. Finally, to balance a suitable amount of total tensile force in the band as a whole, with the relatively lowered values of decitex, strand spacing and pre-strain identified, it may be desired that the elasticized band 145 have a width CW of 5 mm to 30 mm, more preferably 10 mm to 25 mm, and even more preferably 15 mm to 20 mm.

With appropriate selection of beamed elastic strand spacing and decitex, and amount of pre-strain imparted to the strands as they are incorporated in to the cuff structure, an outer leg cuff structure having longitudinal tension within an elasticized band suitable, and comparable to, that in conventional outer leg cuff structures can provide for evenly distributed pressure against the wearer's skin resulting from the longitudinal tension in the strands, resulting in substantially reduced possibility for skin marking and greater wearer comfort. Additionally, combinations of comparatively and appropriately selected reduced spacing, reduced decitex and reduced pre-strain discussed herein causes ruffles of gathered cuff material that are comparatively much smaller in size (i.e., greater machine direction frequency, lesser z-direction amplitude) than the ruffles in conventional leg cuff structures. As a result, the leg cuff structures contemplated herein can lay against the wearer's skin more closely (i.e., with fewer/smaller gaps between ruffles) and more comfortably (i.e., with reduced pressure points at the ruffles).

Where both barrier cuffs and outer leg cuffs are included with an article, they may respectively have elasticized bands 156, 145 that differ in one or more of width, Average Decitex or Manufacturing Decitex, Average-Pre-Strain or Manufacturing Pre-Strain, or Average-Strand-Spacing or Manufacturing Strand Spacing. In some examples, elasticized band 156 may have a width less than that of elasticized band 145; in other examples, elasticized band 145 may have a width less than that of elasticized band 156.

Strands 144 may be directly or indirectly joined to a layer of material forming outer leg cuff wall 146. Outer leg cuff wall 146 may form, and may extend from, outer leg cuff proximal portion 141, to outer leg cuff distal edge 142. Outer leg cuff wall 146 may be a web material that separates the outer leg cuff strands 144 from the wearer's skin when the article is worn normally. Outer leg cuff wall 146 may be formed of any web material having suitably comfortable softness and pliability. In some examples, outer leg cuff wall 146 may be formed of a spunbond nonwoven web material. In some examples, outer leg cuff wall 146 may be formed of any of the materials described above as useful for formation of barrier cuff wall 157 or second layer 158. In some examples, outer leg cuff wall 146 may be formed of laterally extended portion(s) of material(s) forming the topsheet 124 and/or backsheet 125, as suggested in FIGS. 2A and 2F. In some examples, outer leg cuff wall 146 may be formed of a laterally extended portion of material forming the barrier cuff wall 157, as suggested in FIGS. 2A-2E.

As may be appreciated from the figures, strands 144 may be disposed or sandwiched between material forming the outer leg cuff wall 146 and a second layer 147 of outer leg cuff wall 146. Similar to the material forming outer leg cuff wall 146, second layer 147 may be formed of any web material having suitably comfortable softness and pliability. In some examples, second layer 147 may be a conventional spunbond nonwoven web material. In other examples, second layer 147 may be formed of the same type material as that used to form outer leg cuff wall 146. In some examples, second layer 147 is formed of an extended portion of the same material forming outer leg cuff wall 146, which may be folded over to enclose or envelope strands 144 as suggested in FIGS. 2C-2E and 2G-2J. Such a configuration may be useful for providing assurance that strands 144 cannot escape the distal edge of the outer leg cuff structure in the event they become dislodged from their affixed positions within the structure. In some examples, second layer 147 may be formed of laterally extended portion(s) of material(s) forming the topsheet 124 and/or backsheet 125, as suggested in FIGS. 2A, 2B and 2F. In some examples, second layer 147 may be formed of a laterally extended portion of material forming the barrier cuff wall 157, as suggested in FIGS. 2C, 2D, 2E, 2I and 2J.

The materials forming outer leg cuff wall 146 and second layer 147 may be bonded to together for form a laminate structure about strands 144 in any manner described above, for bonding together material forming barrier cuff wall 157 and second layer 158.

As suggested in FIGS. 2A-2E, 2I and 2J, in some examples, the absorbent article may have both a pair of longitudinal barrier cuffs 150 and a pair of outer leg cuffs 140, in combination. As reflected in these figures, in some examples, a barrier cuff 150 and an outer leg cuff 140 may be parts of a combination structure made unitary by sharing a common web component, for example, by having the same web material continuously form, at least, the outer leg cuff wall 146 and the barrier cuff wall 157.

In other examples, structures including both barrier cuffs and outer leg cuffs with beamed elastic strands as described above may be formed, and have features, as described in U.S. Pat. No. 8,939,957 and/or US 2016/0270977.

Waistbands/Waistcaps

The absorbent articles 100 may include one or more elastic waistbands 122. The elastic waistbands 122 may be positioned on the garment-facing surface or the wearer-facing surface, or may be formed therebetween. As an example, a first elastic waistband 122 may be present in the front waist region 36 near the front waist edge 136 and a second elastic waistband 122 may be present in the back waist region 38 near the back waist edge 138. The elastic waistbands 122 may aid in sealing the absorbent article 100 around a waist of a wearer and at least inhibiting bodily exudates from escaping the absorbent article 100 through the waist opening circumference. In some instances, an elastic waistband may fully surround the waist opening 190 of the absorbent article 100. A waist cap 123 may be formed by an extension of the waistband 122 and may remain unattached to the underlying structure in the central portion of the waist cap 123 to allow bodily exudates that flow along the topsheet 124 to be trapped between the topsheet 124 and the underside of the waist cap 123. In other words, the waist cap 123 may be joined to the underlying structure, e.g., center chassis 200 of the absorbent article 100 along the longitudinally distal edge of the waist cap 123 and/or along the laterally opposing side edges of the waist cap 123.

Belts

Beyond what was disclosed about belts in the OPEN-FORM TAPED ARTICLE and CLOSED-FORM PANT ARTICLE Sections above, the front and back belts 430*f* and 430*b* may include front and back inner belt layers 432 and front and back outer belt layers 434 having an elastomeric material (e.g., a plurality of elastics 316 or a film (which may be apertured)) disposed at least partially therebetween. The plurality of elastics 316 or the film may be relaxed (including being cut) to reduce elastic strain over the absorbent core 128 or, alternatively, may run continuously across the absorbent core 128. The plurality of elastics 316 may have uniform or variable spacing therebetween in any portion of the belts. The plurality of elastics 316 may also be pre-strained the same amount or different amounts. The front and/or back belts 430*f* and 430*b* may have one or more elastics-free zones where the chassis 200 overlaps the belts 430*f* and 430*b*. In other instances, at least some of the plurality of elastics 316 may extend continuously across the chassis 200.

The front and back inner belt layers 432 and the front and back outer belt layers 434 may be joined using adhesives, heat bonds, pressure bonds, ultrasonic, or thermoplastic bonds. Various suitable belt layer configurations can be found in U.S. Pat. Appl. Pub. No. 2013/0211363.

Front and back belt end edges 438*f* and 438*b* may extend longitudinally beyond the front and back chassis end edges 236 and 238 or they may be co-terminus. The front and back belt side edges 437 may extend laterally beyond the chassis side edges 237*a* and 237*b*. The front and back belts 430*f* and 430*b* may be continuous (i.e., having at least one layer that is continuous (see 434 in FIG. 7E) from belt end edge 438*f* to the opposite belt end edge 438*b*). Alternatively, the front and back belts 430*f* and 430*b* may be discontinuous from belt end edge 438*f* to the opposite belt end edge 438*b* (see 432 and 434 in FIG. 7D), such that they are discrete.

As disclosed in U.S. Pat. No. 7,901,393, the longitudinal length (along the central longitudinal axis 42) of the back belt 430*b* may be greater than the longitudinal length of the front belt 430*f*, and this may be particularly useful for increased buttocks coverage when the back belt 430*b* has a greater longitudinal length versus the front belt 430*f* adjacent to or immediately adjacent to the side seams 172. Alternatively, the bottom corners of the longer back belt may be trimmed in diagonal lines or curves.

The front and back belts 430*f* and 430*b* may include slits, holes, and/or perforations providing increased breathability, softness, and a garment-like texture. Underwear-like appearance can be enhanced by substantially aligning the waist and leg edges at the side seams 172.

Transverse Barrier

Figure 13:
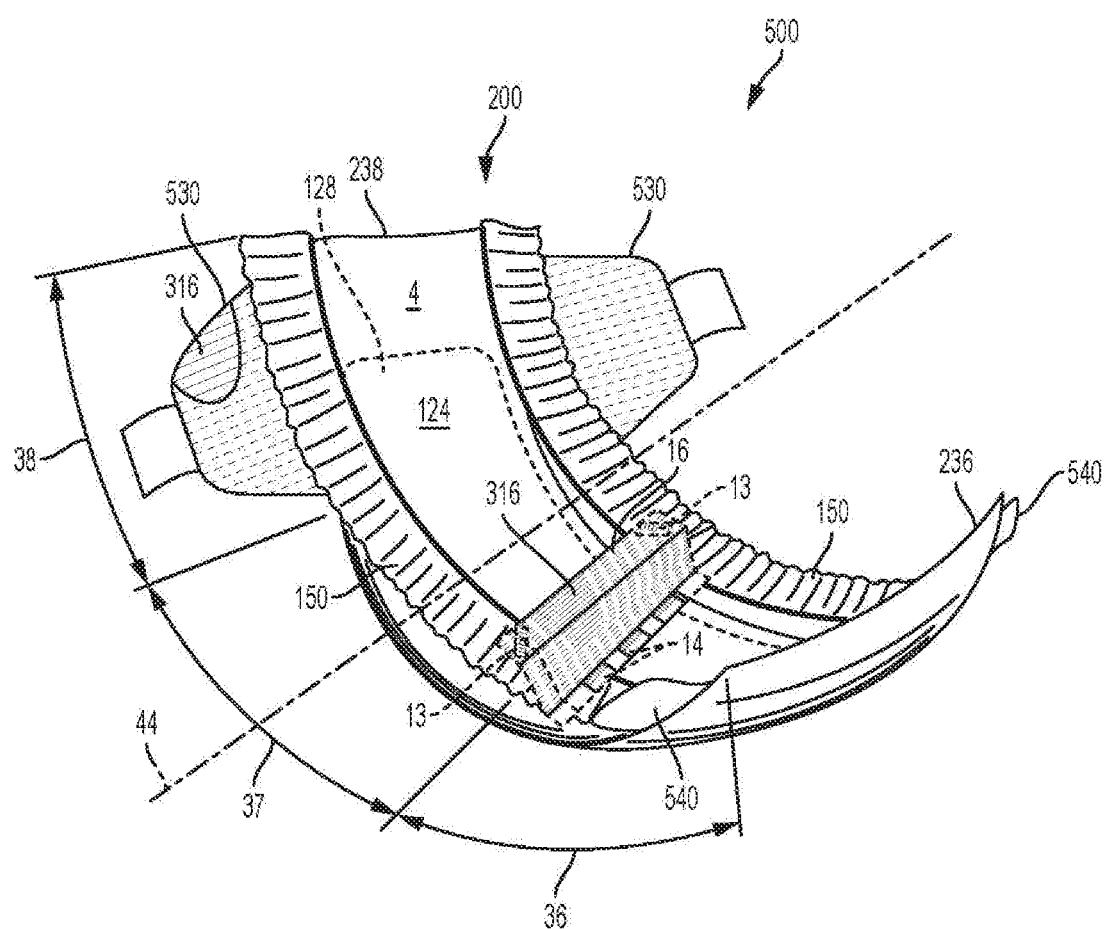
FIG. 13 is a perspective interior top view of a taped article including a transverse barrier.

As shown in FIG. 13, the transverse barrier 16 may extend parallel with the lateral axis 44 and may be joined via bonds 13 to the cuffs 150 and joined by bonds 14 to the topsheet 124 such that the transverse barrier extends in a Z direction away from the topsheet when the article (e.g., 500) is opened and worn. More particularly, the transverse barrier 16 may extend in a Z direction due in part to the cuffs standing upward in the Z direction as the article is opened for wear. The transverse barrier 16 may prevent fecal matter from migrating into the front waist region 36. Thus, the transverse barrier 16 may be oriented proximate to where the front waist region 36 and crotch region 37 meet, or may be disposed between the juncture of where the front waist region 36 and the crotch region 37 meet and the lateral axis 44. Offsetting the bond locations 13 and 14 will influence the angle of the transverse barrier 16 relative to the topsheet 124. The bond locations 13 and 14 may be oriented such that the transvers barrier extends in a Z direction that is approximately 90 degrees from the surface of the topsheet 124.

Feminine Hygiene Article

Referring to FIGS. 11-12C, an absorbent article may be a feminine hygiene article 801 also referred to as a sanitary napkin, and includes feminine pads, and liners. The sanitary napkin 801 may include a liquid permeable topsheet 124, a liquid impermeable, or substantially liquid impermeable, backsheet 125 and an absorbent core 128. The liquid impermeable backsheet 125 may or may not be vapor permeable. The absorbent core 128 may have any or all of the features described herein with respect to the absorbent core 128 and, in some forms, may have a secondary topsheet 124' (STS) instead of the acquisition materials disclosed above. The STS 124' may include one or more channels, as described above (including the embossed version). In some forms, channels in the STS 124' may be aligned with channels in the absorbent core 128. The sanitary napkin 801 may also include wings 120 extending outwardly with respect to a longitudinal axis 42 of the sanitary napkin 801. The sanitary napkin 801 may also include a lateral axis 44. The wings 120 may be integral to TS, BS joined to the topsheet 124, the backsheet 125, and/or the absorbent core 128.

Process

Figure 14:
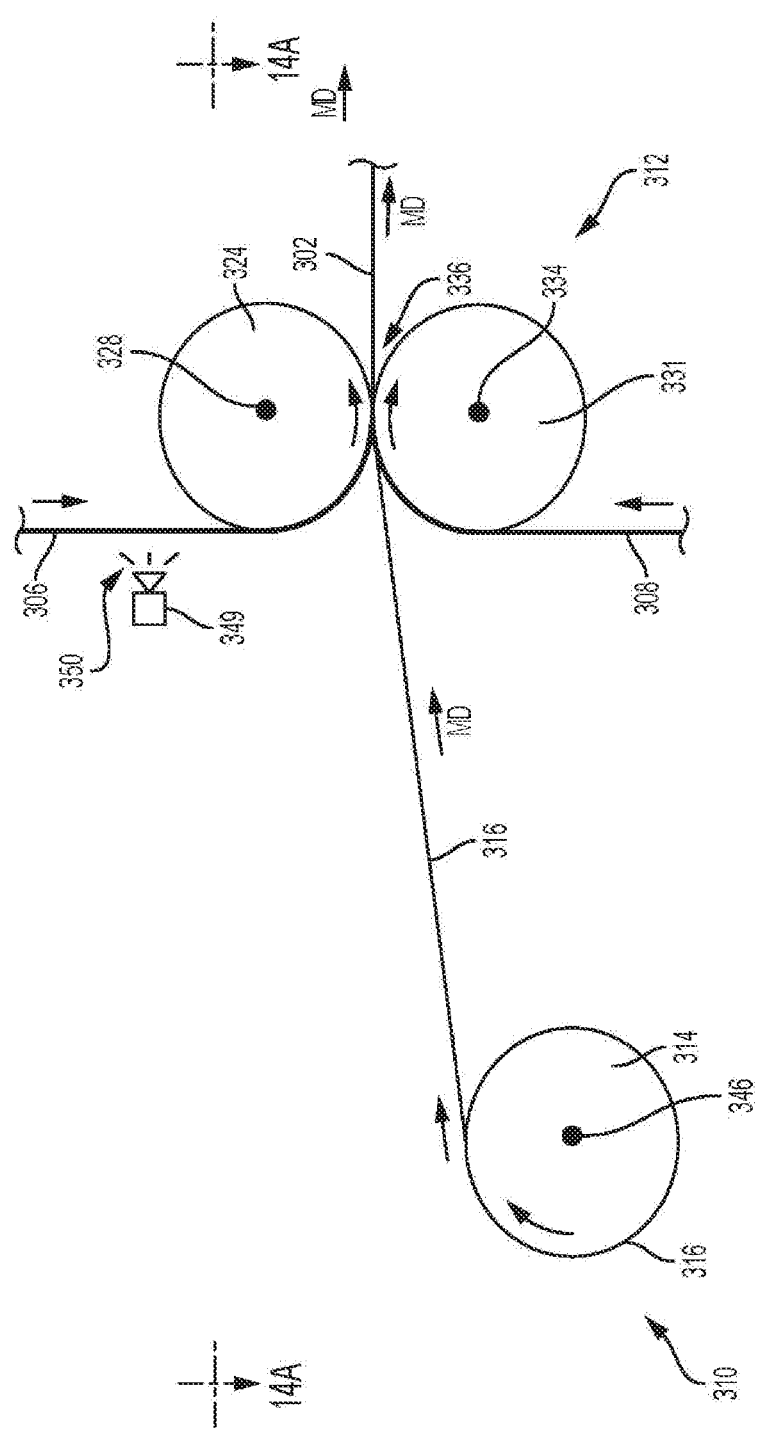
FIG. 14 is a schematic side view of a converting apparatus adapted to manufacture an elastic laminate including a first plurality of elastics positioned between a first substrate and a second substrate.
Figure 15:
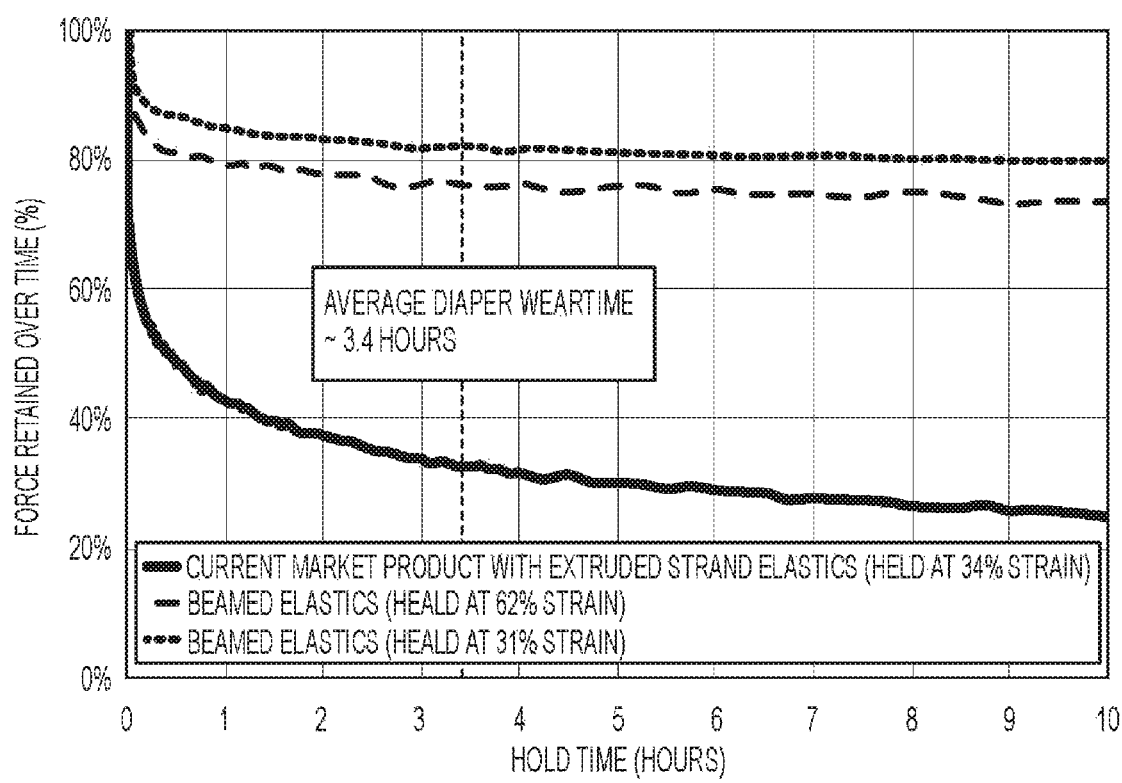
FIG. 15 is a chart showing force relaxation over time for various elastic laminates.

Referring to FIGS. 14 and 14A, a plurality of elastics 316 (from about 10 strands to about 1500 strands having a decitex from about 10 to about 500) unwind about a first axis of rotation 346 from a first beam 314 (which is a first metering device 310) in the machine direction MD and transfer the plurality of elastics 316 from the first beam 314 to a second metering device 312 (which includes a first roller 324 having a second axis of rotation 328 and a second roller 331 having a third axis of rotation 334, which form a nip 336). The plurality of elastics 316 may be stretched along the machine direction MD between the first metering device 310 and the second metering device 312 to pre-strain the elastics (from about 50% to about 400%). The stretched elastic strands 316 are also joined via an adhesive 350 from an adhesive applicator 349 with a first substrate 306 and a second substrate 308 at the second metering device 312 to produce an elastic laminate 302, such that each of the strands are spaced (in the CD) in the elastic laminate from about 0.25 mm to about 5 mm. It is this elastic laminate 302 that may be further incorporated into the various absorbent article components such as the belts, ear panels, side panels, transverse barriers, topsheets, backsheets, cuffs, waistbands, and/or chassis to offer the benefits described in this patent application. Further details of the process of creating beamed elastic laminate(s) for use in disposable absorbent articles are disclosed in U.S. App. Ser. No. 62/43658, titled "METHODS AND APPARATUSES FOR MAKING ELASTOMERIC LAMINATES WITH ELASTIC STRANDS UNWOUND FROM BEAMS," first-named inventor being Schneider, filed on Dec. 20, 2016. The elastic laminate 302 may be produced as part of the absorbent article manufacturing line, or may be produced offline, and unwound as an elastic laminate that is fed into the absorbent article manufacturing line.

Elastomeric Laminate(s) Having Beamed Elastics

When the elastic laminate 302 may form at least a portion of one or more of the group of article components including a belt 430, a side panel 330, chassis 200, a topsheet 124, backsheet 125, and an ear panel 530, the elastic laminate 302 may include a plurality of elastics incorporated with a Manufacturing Strand Spacing, or having an Average-Strand-Spacing of from about 40 to about 1000 elastic strands with an average strand spacing from about 0.25 mm to about 4 mm, an average dtex from about 10 to about 500, a pre-strain from about 50% to about 400%; and a first substrate 306 and a second substrate 308 each having a basis weight from about 6 grams per square meter to about 30 grams per square meter.

When the elastic laminate 302 may form at least a portion of one or more of the group of article components including a belt 430, a side panel 330, chassis 200, a topsheet 124, backsheet 125, and an ear panel 530, the elastic laminate 302 may include a plurality of elastics incorporated with a Manufacturing Strand Spacing, or having an Average-Strand-Spacing, of from about 50 to about 825 elastic strands. Further, the plurality of elastics may include from about 100 to about 650 elastic strands. Still further, the plurality of elastics may include from about 150 to about 475 elastic strands.

When the elastic laminate 302 may form at least a portion of one or more of the group of article components including a belt 430, a side panel 330, chassis 200, a topsheet 124, backsheet 125, and an ear panel 530, the elastic laminate 302 may include a plurality of elastics incorporated with a Manufacturing Strand Spacing, or incorporated to have an Average-Strand-Spacing, of from about 0.5 mm to about 3.5 mm. Further, the plurality of elastics may be incorporated with a Manufacturing Strand Spacing, or incorporated to have an Average-Strand-Spacing, of from about 0.75 mm to about 2.5 mm.

When the elastic laminate 302 may form at least a portion of one or more of the group of article components including a belt 430, a side panel 330, chassis 200, a topsheet 124, backsheet 125, and an ear panel 530, the elastic laminate 302 may include a plurality of elastics selected to have an Average Decitex and/or Manufacturing Decitex from about 30 to about 400. Further, the elastic laminate 302 may have an Average Decitex and/or Manufacturing Decitex of the plurality of elastics from about 50 to about 250.

When the elastic laminate 302 may form at least a portion of one or more of the group of article components including a belt 430, a side panel 330, chassis 200, a topsheet 124, backsheet 125, and an ear panel 530, the elastic laminate 302 may include a plurality of elastics incorporated with a Manufacturing Pre-Strain of from about 75% to about 300%; or alternatively, incorporated with an amount of pre-strain that results in a laminate with an Average-Pre-Strain within this range. Further, the elastic laminate may include a plurality of elastics 316 incorporated with a Manufacturing Pre-Strain of from about 100% to about 250%; or alternatively, incorporated with an amount of pre-strain that results in a laminate with an Average-Pre-Strain within this range.

The elastic laminate 302 may form at least a portion of one or more of the group of article components including a waistband 122, waistcap 123, inner barrier leg cuff 150, outer leg cuff 140 and a transverse barrier 16, and may include a plurality of elastics having from about 10 to about 400 elastic strands with an Average-Strand-Spacing and/or Manufacturing Strand Spacing from about 0.25 mm to about 4 mm, selected to have an Average Decitex and/or Manufacturing Decitex of from about 10 to about 500, incorporated with a Manufacturing Pre-Strain of from about 50% to about 400%; or alternatively, incorporated with an amount of pre-strain that results in a laminate with an Average-Pre-Strain within this range, and a first substrate 306 and/or second substrate 308 each having a basis weight from about 6 grams per square meter to about 30 grams per square meter.

The elastic laminate 302 may form at least a portion of one or more of the group of article components including a waistband 122, waistcap 123, inner barrier leg cuff 150, outer leg cuff 140 and a transverse barrier 16, and may include a plurality of elastics having from about 15 to about 300 elastic strands. Further, the plurality of elastics may include from about 20 to about 225 elastic strands. Further, the plurality of elastics may include from about 25 to about 150 elastic strands.

The elastic laminate 302 may form at least a portion of one or more of the group of article components including a waistband 122, waistcap 123, inner barrier leg cuff 150, outer leg cuff 140 and a transverse barrier 16, and may include a plurality of elastics having an Average-Strand-Spacing and/or Manufacturing Strand Spacing from about 0.5 mm to about 3.0 mm. Further, the plurality of elastics 316 may have an Average-Strand-Spacing and/or Manufacturing Strand Spacing from about 0.75 mm to about 2.5 mm.

The elastic laminate 302 may form at least a portion of one or more of the group of article components including a waistband 122, waistcap 123, inner barrier leg cuff 150, outer leg cuff 140 and a transverse barrier 16, and may include a plurality of elastics selected to have an Average Decitex and/or Manufacturing Decitex from about 30 to about 400. Alternatively, the plurality of elastics 316 of the elastic laminate 302 may be selected to have an Average Decitex and/or Manufacturing Decitex from about 50 to about 250.

The elastic laminate 302 may form at least a portion of one or more of the group of article components including a waistband 122, waistcap 123, inner barrier leg cuff 150, outer leg cuff 140 and a transverse barrier 16, and may include a plurality of elastics incorporated with a Manufacturing Pre-Strain from about 75% to about 300%; or alternatively, incorporated with an amount of pre-strain that results in a laminate with an Average-Pre-Strain within this range. Alternatively, the elastic laminate may include a plurality of elastics incorporated with a Manufacturing Pre-Strain from about 100% to about 250%; or alternatively, incorporated with an amount of pre-strain that results in a laminate with an Average-Pre-Strain within this range.

An absorbent article may have an elastic laminate 302 forming a portion of one or more of a belt 430, side panel 330, ear panel 530, waistband 122, chassis 200, topsheet 124 and backsheet 125. The elastic laminate 302 may include a plurality of elastics having a specific elastic decitex, nonwoven type, nonwoven basis weight, elastic spacing and elastic strain. And, the article may include two or more absorbent article components (including a belt 430, side panel 330, ear panel 530, waistband 122, chassis 200, topsheet 124 and backsheet 125) including an elastic laminate 302 having one or more identical or substantially identical elastic laminate elements (including elastic decitex, nonwoven type, nonwoven basis weight, elastic spacing and elastic strain).

Beyond the beamed elastic strands 316 that may be used in each of the absorbent article components, other elastic components such as elastic nonwovens, elastomeric films, elastomeric foams, elastomeric scrims, and elastomeric ribbons, or combinations thereof, may be used with the beamed elastics 316.

The elastic laminate 302 may include a plurality of elastics 316 that may be the same color as one or both of the first substrate layer 306 and second substrate layer 308 so the elastic material may be more hidden, i.e. masked or may be of a different color so the elastic material is visible in the elastic laminate 302. Furthermore, the plurality of elastic 316 may be transparent or translucent such that it is virtually invisible. Transparency or translucency combined with the very low decitex of the elastic 316 may render the elastic 316 visibly and tactilely unnoticeable by users of absorbent articles including elastic laminate 302 including such elastics 316.

Multiple Beams

It should be appreciated that one or more of a waistband 122, waistcap 123, inner barrier leg cuff 150, outer leg cuff 140 and/or a transverse barrier may be formed from multiple beams of elastic. For example, one beam may form a first portion of one or more of a waistband 122, waistcap 123, inner barrier leg cuff 150, outer leg cuff 140 and/or a transverse barrier and a second beam may form a second portion of one or more of a waistband 122, waistcap 123, inner barrier leg cuff 150, outer leg cuff 140 and/or a transverse barrier, where the separate beams may include a different number of elastics, and/or the beams may have elastics having different decitex, and/or the elastics of the two beams may be disposed at different spacing, and/or the separate beams may deliver elastics having different pre-strain, and/or the different beams may deliver elastics having different orientations in the product, e.g. liner, arcuate, angled, etc. The resultant portions of the waistband 122, waistcap 123, inner barrier leg cuff 150, outer leg cuff 140 and/or transverse barrier created from such a multi-beam approach may have different texture, garment-like appearance, modulus and/or different force.

It is also to be appreciated that one or more of the absorbent article components including a belt 430, side panel 330, ear panel 530, waistband 122, chassis 200, topsheet 124 and backsheet 125, may include an elastic laminate 302 formed from multiple beams of elastic. For example, one beam may form a first portion of one or more absorbent article components including a belt 430, side panel 330, ear panel 530, waistband 122, chassis 200, topsheet 124 and backsheet 125, and a second beam may form a second portion of an absorbent article component including a belt 430, side panel 330, ear panel 530, waistband 122, chassis 200, topsheet 124 and backsheet 125. The separate beams may include a different number of elastics and the beams may have a plurality of elastics 316 having different decitex. The elastics of the two beams may be disposed at different spacing and/or the separate beams may deliver elastics having different pre-strain and/or the different beams may deliver elastics having different orientations in the product, e.g. liner, arcuate, angled, etc. The resultant portions of the absorbent article components including a belt 430, side panel 330, ear panel 530, waistband 122, chassis 200, topsheet 124 and/or backsheet 125 created from such a multi-beam approach may have different texture, garment-like appearance, modulus and/or different force.

Laterally Extending Elastics

A wearable article may include one or more elastic laminates 302 having a plurality of laterally extending a plurality of elastics, where the one or more elastic laminates may be present in a first waist region, the crotch region and/or in the opposing second waist region, and where the plurality of elastics 316 may be disposed in one or both of the first and second waist regions may have one or more of a higher elastic decitex, higher percent strain, and smaller average strand spacing than some or all of the laterally extending a plurality of elastics disposed in the crotch region. Such a wearable article may include one or more elastic laminates 302 having a plurality of elastics 316 having from about 100 to about 1500 elastic strands disposed at a Manufacturing Strand Spacing, or disposed so as to result in an Average-Strand-Spacing, from about 0.25 mm to about 4 mm, selected to have an Average Decitex and/or Manufacturing Decitex of from about 10 to about 500, imparted with a Manufacturing Pre-Strain of, imparted with an amount of pre-strain that results in a laminate with an Average-Pre-Strain of, from about 50% to about 400%, and a first substrate 306 and/or second substrate 308 each having a basis weight from about 6 grams per square meter to about 30 grams per square meter.

Elastic Strand Composition (Spandex Vs. Extruded Strands)

Beamed elastic uses Spandex fibers. One type of Spandex fiber is "PolyUrethane Urea" elastomer or the "high hard segment level PolyUrethane" elastomer, which must be formed into fibers using a solution (solvent) spinning process (as opposed to being processable in the molten state.) The Urea linkages in PolyUrethane Urea provides strong mutual chemical interactions crucial for providing "anchoring" that enables good stress relaxation performance at temperatures near body temperature on timescales corresponding to diaper wear, including overnight. This type of anchoring enables better force relaxation (i.e. little force decay with time when held in stretched condition at body temperature) over many thermoplastic polyurethane (PolyUrethane with hard segment melting below 200 deg. C.) or thermoplastic Styrenic block copolymers.

In contrast, extruded strands and scrims are typically made of Styrenic block copolymers or thermoplastic elastomers that can be formed in the molten state by conventional extrusion processes. Thermoplastic elastomers include compositions like polyolefin, polyurethane (PolyUrethane with hard segment melting below 200 deg. C.) elastomers, etc. Because these thermoplastic elastomers like Polyurethane (PolyUrethane with hard segment melting below 200 deg. C.) can be melted/re-melted, and extruded it makes them susceptible to higher stress relaxation in use, which is a major negative. The styrenic block copolymers used in extruded strands include a comparatively long rubbery midblock situated between comparatively short end blocks. End blocks sufficiently short to enable good flow conventional extrusion processes often have a greater propensity to stress relax and undergo force relaxation over time see FIG. 23.

The Urea linkage present in Spandex requires it to be made by spinning process. Spandex can't be melted/re-melted or extruded like Styrenic block copolymers. Spandex pre-polymer is combined with solvent and additives, and the solution is spun to make solid spandex fiber. Multiple fibers are then formed together to make one spandex strand. The Spandex strands may have surface finish to avoid blocking and wound onto spools. The one spandex fiber may have a decitex of about 15, so a 500 decitex strand may have nominally 33 fibers wound together to make one strand. Depending on the decitex we use for beam approach, we may have 15 fibers (or filaments), 8 fibers, 5 fibers, 3 fibers or even as low as 2 fibers. Spandex fiber can be monocomponent or bi-component (as disclosed in WO201045637A2).

Further related to the chemistry of beamed elastics, it may be desirable to coat the beamed elastics with an oil, such as a silicone oil, including about 10%, about 7%, about 5%, about 3%, or about 1% silicone oil. Treating the beamed elastics with silicone oil helps to prevent blocking (crosslinking) when the strands are wound to a spool or a beam and it also lowers the COF for the strand in textile machinery (for weaving, knitting and warping processes).

Commercially available Spandex strands may also be known as Lycra, Creora, Roica, or Dorlastan. Spandex is often referred as Elastane fiber or Polyurethane fiber.

Beamed Elastomeric Laminate Examples

Consumer interactions and research has shown that a longstanding unmet consumer need exists to provide absorbent articles which have the right balance of modulus for application and removal ease and freedom of movement while providing an article with low elastic pressure (relative to today's stranded products) to provide a comfortable wearing experience free from skin marks. It has been found that elastic laminate structures having a Section-Modulus of between about 2 gf/mm and 15 gf/mm, alternatively from about 4 gf/mm to about 10 gf/mm, are most desirable for ease of application, ease of removal, conforming fit and freedom of movement. Depending on the elastic configuration in these structures they may exhibit very high Pressure-Under-Strand, e.g., elastic strands, leading to increased skin marking and reduced comfort. One approach to reduce the pressure of the elastic on the skin is to increase the number of elastics for a given area. Increasing the number of elastics within a given area alone may reduce the Pressure-Under-Strand, however, if that is the only change it can also significantly increase the overall modulus of the elastic laminate structure. In order to achieve the right balance of modulus and pressure on the skin it is necessary to reduce the elastic decitex and/or the elastic strain as the spacing between the elastics is reduced thereby increasing the elastic number in order to balance the modulus and pressure on the skin and maintain these parameters within the consumer preferred range. This breakthrough has been enabled through delivery of very low decitex elastic at very low strain levels and with very tight elastic spacing that have never before been seen in disposable absorbent articles. Delivery of such low decitex elastic at low strain and tight spacing is enabled via a new to absorbent article technology created from the textile warp beam technology approach. The examples below are some embodiments of such elastomeric structures.

TABLE 1

Inventive Belt Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A Front Belt | | | | | | | |
| 1 | 40 | 140 | 100% | 0.6 | 79.2% | 10.9 | 0.328 |
| 2 | 40 | 70 | 150% | 0.6 | 85.3% | 5.5 | 0.463 |
| 3 | 40 | 70 | 150% | 0.6 | 85.3% | 5.5 | 0.463 |
| 4 | 40 | 140 | 100% | 0.6 | 79.2% | 10.9 | 0.328 |
| Back Belt | | | | | | | |
| 4 | 40 | 140 | 100% | 0.6 | 79.2% | 10.9 | 0.328 |
| 3 | 40 | 70 | 150% | 0.6 | 85.3% | 5.5 | 0.463 |
| 2 | 40 | 70 | 150% | 0.6 | 85.3% | 5.5 | 0.463 |
| 1 | 40 | 140 | 100% | 0.6 | 79.2% | 10.9 | 0.328 |

TABLE 1-continued

Inventive Belt Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| B |
| Front Belt |
| 1 | 50 | 70 | 175% | 0.5 | 82.4% | 6.6 | 0.386 |
| 2 | 50 | 70 | 175% | 0.5 | 82.4% | 6.6 | 0.386 |
| 3 | 50 | 70 | 175% | 0.5 | 82.4% | 6.6 | 0.386 |
| 4 | 50 | 70 | 175% | 0.5 | 82.4% | 6.6 | 0.386 |
| Back Belt |
| 4 | 50 | 70 | 175% | 0.5 | 82.4% | 6.6 | 0.386 |
| 3 | 50 | 70 | 175% | 0.5 | 82.4% | 6.6 | 0.386 |
| 2 | 50 | 70 | 175% | 0.5 | 82.4% | 6.6 | 0.386 |
| 1 | 50 | 70 | 175% | 0.5 | 82.4% | 6.6 | 0.386 |
| C |
| Front Belt |
| 1 | 30 | 70 | 200% | 0.8 | 89.0% | 4.1 | 0.618 |
| 2 | 20 | 210 | 150% | 1.1 | 86.1% | 8.9 | 0.490 |
| 3 | 30 | 70 | 200% | 0.8 | 89.0% | 4.1 | 0.618 |
| 4 | 30 | 70 | 200% | 0.8 | 89.0% | 4.1 | 0.618 |
| Back Belt |
| 4 | 30 | 70 | 200% | 0.8 | 89.0% | 4.1 | 0.618 |
| 3 | 30 | 70 | 200% | 0.8 | 89.0% | 4.1 | 0.618 |
| 2 | 30 | 70 | 200% | 0.8 | 89.0% | 4.1 | 0.618 |
| 1 | 30 | 210 | 150% | 1.1 | 86.1% | 8.9 | 0.490 |

TABLE 2

Inventive Ear/Side Panel Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A |
| 1 | 30 | 140 | 125% | 1.0 | 87.5% | 6.6 | 0.546 |
| 2 | 30 | 140 | 125% | 0.8 | 84.4% | 8.2 | 0.437 |
| 3 | 30 | 140 | 125% | 1.0 | 87.5% | 6.6 | 0.546 |
| 4 | 30 | 140 | 125% | 1.0 | 87.5% | 6.6 | 0.546 |
| B |
| 1 | 60 | 70 | 125% | 0.5 | 82.4% | 6.6 | 0.386 |
| 2 | 60 | 70 | 125% | 0.5 | 82.4% | 6.6 | 0.386 |
| 3 | 60 | 70 | 125% | 0.5 | 82.4% | 6.6 | 0.386 |
| 4 | 60 | 70 | 125% | 0.5 | 82.4% | 6.6 | 0.386 |
| C |
| 1 | 15 | 210 | 165% | 2.0 | 92.4% | 4.9 | 0.892 |
| 2 | 15 | 210 | 165% | 1.1 | 86.1% | 8.9 | 0.490 |
| 3 | 15 | 210 | 165% | 2.0 | 92.4% | 4.9 | 0.892 |
| 4 | 15 | 210 | 165% | 2.0 | 92.4% | 4.9 | 0.892 |

Note:
Side panels/ears may have the same Open Area(s) as the belt(s) of Table 1.

TABLE 3

Inventive Waistband Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A | | | | | | | |
| 1 | 40 | 111 | 100% | 0.6 | 81.5% | 8.7 | 0.368 |
| B | | | | | | | |
| 1 | 50 | 90 | 110% | 0.5 | 80.0% | 8.4 | 0.341 |
| C | | | | | | | |
| 1 | 35 | 120 | 200% | 0.7 | 83.5% | 8.0 | 0.413 |

Note:
Waistbands may have the same Open Area(s) as the belt(s) of Table 1.

TABLE 4

Inventive Cuff Elastic Profiles

| Section | Number of Elastics | Average-Dtex | Average-Pre-Strain | Average-Strand-Spacing (mm) | Open Area (%) | Section-Modulus (gf/mm) | Pressure-Under-Strand (psi) |
|---|---|---|---|---|---|---|---|
| A | | | | | | | |
| Inner | 50 | 30 | 200% | 0.5 | 88.5% | 2.8 | 0.590 |
| Outer | 50 | 70 | 200% | 0.5 | 82.4% | 6.6 | 0.386 |
| B | | | | | | | |
| Inner | 25 | 70 | 170% | 0.5 | 82.4% | 6.6 | 0.386 |
| Outer | 25 | 140 | 200% | 1.0 | 87.5% | 6.6 | 0.546 |
| C | | | | | | | |
| Inner | 25 | 140 | 85% | 0.5 | 75.1% | 13.1 | 0.273 |
| Outer | 25 | 140 | 200% | 1.0 | 87.5% | 6.6 | 0.546 |

Note:
Cuffs may have the same Open Area(s) as the belt(s) of Table 1.

Example 1—Belt Pant Article (See, for Example, FIGS. 5, 5A, 6, 7, 7A, and 8)

Example 1 is a belted pant absorbent article. The pant includes a belt laminate disposed in both the waist regions and the following materials and construction.
Outer Belt Layer (first substrate layer 306): 13 gsm spunbond nonwoven
Inner Belt Layer (second substrate layer 308): 13 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Belt Elastic Profile: Table 1, col B
Cuff Elastic Profile: Table 4, col C Example 2—Taped Article (see, for Example, FIGS. 9, 9A, and 10)

Example 2 is a side panel taped absorbent article. The taped article includes a pair of side panels disposed in a first waist region and the following materials and construction.
Elastomeric Ear Panel Outer Layer (first substrate layer 306): 17 gsm carded nonwoven
Elastomeric Ear Panel Inner Layer (second substrate layer 308): 17 gsm spunbond nonwoven
Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Side Panel Elastic Profile: Table 2, col A
Cuff Elastic Profile: Table 4, col B
Front Waistband: Table 3, col A
Back Waistband: Table 3, col A Example 4—Side Panel Pant Article (see, for Example, FIGS. 3 and 3B)

Example 4 is a side panel pant absorbent article. The pant article has a pair of side panels disposed in each waist region and includes the following materials and construction.
Side Panel Outer Layer (first substrate layer 306): 17 gsm carded nonwoven
Side Panel Inner Layer (second substrate layer 308): 17 gsm spunbond nonwoven Backsheet Film 126: 12 gsm liquid impermeable polyethylene film
Core Wrap: 10 gsm hydrophilic spunbond nonwoven
AGM: absorbent gelling material
Distribution Layer: crosslinked cellulosic fiber
Acquisition Layer: 43 gsm synthetic acquisition layer
Topsheet 124: 12 gsm hydrophilic spunbond nonwoven
Front Side Panel Elastic Profile: Table 2, col B
BackSide Panel Elastic Profile: Table 2, col B
Cuff Elastic Profile: Table 4, col A
Front Waistband: Table 3, col C
Back Waistband: Table 3, col C It is desirable for the elastomeric laminate of the present invention to have a Pressure-Under-Strand of from about 0.1 psi to about 1.0 psi. In certain embodiments, the Pressure-Under-Strand may be from about 0.2 to about 0.8 psi.

It is desirable for the elastomeric laminate of the present invention to have a Pressure-Under-Strand of from about 0.1 psi to about 1.0 psi. In certain embodiments, the Pressure-Under-Strand may be from about 0.2 to about 0.8 psi.

It is desirable for the elastomeric laminate of the present invention to have a Pressure-Under-Strand of from about 0.1 psi to about 1.0 psi. In certain embodiments, the Pressure-Under-Strand may be from about 0.2 to about 0.8 psi.

as the region disposed between and including the distal most elastic and the proximal most elastic.

Methods

General Sample Preparation

The General Sample Preparation is intended to be used for methods that do not have specific sample preparation instructions within the method itself.

The When collecting a specimen for testing, the specimen must contain a plurality of elastic strands and/or an elastic material; film, elastic scrim, elastic foam, elastic ribbons, elastic strips, etc. In situations where the elastic material and/or elastic strands is not fully secured within the sample, the test specimen must be obtained in a way that elastic material and/or elastic strands within the test region of the specimen are as they were intended and not altered as a result of collection of the specimen. If the elastic material or any elastic strands release, creep or become separated within or from the laminate, the specimen is discarded and a new specimen prepared.

For pants, remove the side panels where they are attached to the chassis and separate the side panels at the side seams. Identify the elastic material that transverses the entire width of the panel. Identify the longitudinally distal most edge of the elastic material or elastic strand (closest to the waist

TABLE 5

Performance Characteristics of Existing and Inventive Belt Sections

| Example Belt Sections | Average-Dtex | Average-Strand-Spacing (mm) | Open Area (%) | Section-Modulus (gf/mm) | Pressure-Under-Strand (psi) |
|---|---|---|---|---|---|
| Pampers Easy Ups Training Underwear for Boys size 4T-5T (example section 1 of 4) | 1100 | 9.0 | 96.1% | 5.7 | 1.753 |
| Pampers Easy Ups Training Underwear for Boys size 4T-5T (example section 2 of 4) | 940 | 9.0 | 96.4% | 7.3 | 1.897 |
| Pampers Easy Ups Training Underwear for Boys size 4T-5T (example section 3 of 4) | 680 | 9.0 | 97.0% | 3.5 | 2.230 |
| Always Discreet Underwear Maximum Classic Cut size S/M (example section 1 of 4) | 800 | 7.0 | 95.7% | 5.4 | 1.599 |
| Always Discreet Underwear Maximum Classic Cut size S/M (example section 2 of 4) | 680 | 7.0 | 96.1% | 4.6 | 1.734 |
| Always Discreet Boutique Maximum Protection size S/M (example section 1 of 4) | 470 | 4.0 | 94.3% | 5.5 | 1.192 |
| Always Discreet Boutique Maximum Protection size S/M (example section 2 of 4) | 680 | 4.0 | 93.1% | 8.0 | 0.991 |
| Inventive Example (example section 1 of 4) | 160 | 0.5 | 73.4% | 15.0 | 0.255 |
| Inventive Example (example section 2 of 4) | 140 | 0.5 | 75.1% | 13.1 | 0.273 |
| Inventive Example (example section 3 of 4) | 250 | 0.8 | 79.2% | 14.6 | 0.327 |

It may be for the elasticized laminate of the present invention to have a Pressure-Under-Strand of from about 0.1 psi to about 1.0 psi. In certain examples, the Pressure-Under-Strand may be adjusted to be from about 0.2 to about 0.8 psi.

Absorbent Article Sections

Components of absorbent articles comprising elastomeric laminates 302 may be sectioned to enable measurement and detailed characterization of the structure. Waistband 122, waistcap 123, inner leg cuff 150, outer leg cuff 140 and transverse barrier 165 all comprise 1 section. With regard to the waistband 122, waistcap 123, inner leg cuff 150, outer leg cuff 140 and transverse barrier 165 the section is defined edge) and the longitudinally proximal most edge of the elastic material or elastic strand (closest to the leg edge) determine the midpoint between the distal most elastic strand or elastic material edge and the proximal most elastic strand or elastic material edge. Cut a 40 mm wide strip laterally across the entire panel centered at the midpoint. Repeat for each front and rear side panel that contains elastic material and/or elastic strands.

For taped diapers, remove ear panels where they are attached to the chassis. Identify the elastic material that transverses the entire width of the panel. Identify the distal most elastic material edge or elastic strand (closest to the waist edge) and the proximal most elastic material edge or elastic strand (closest to the leg edge) determine the midpoint between the distal most elastic strand or elastic material edge and the proximal most elastic strand or elastic material edge. Cut a 40 mm wide strip laterally across the entire ear panel centered at the midpoint. Repeat for each front and rear ear panel that contains elastic material and/or elastic strands.

For a belted article, mark the product on the front and back by extending a line from along the side of the core to the waist edge. Remove the belt from the article, using an appropriate means (e.g. freeze spray), taking care not to delaminate the belt or release the elastics. Separate the front belt from the back belt along any seams. Identify the distal most elastic material edge or elastic strand (closest to the waist edge) and the proximal most elastic material edge or strand (closest to the leg edge) determine the midpoint between the distal most elastic strand or elastic material edge and the proximal most elastic strand or elastic material edge. Cut a 40 mm wide strip parallel to the waist edge if linear or to the elastic strands if linear and centered at the midpoint, across the entire belt portion. If the strip has a region that does not contain elastic strands or elastic material (e.g., a portion that overlapped the core, etc.) cut along the ends of the elastic strands/elastic material, to remove the non-elastic region and treat as two specimens.

For waistbands, they are tested as a single piece of material. Remove the belt from the article, using an appropriate means (e.g. freeze spray), taking care not to delaminate the belt or release the elastics.

For the leg cuffs, each of the leg cuffs is tested as a single piece of material. The inner leg cuff sample is considered to be the portion of the inner leg cuff that extends from the proximal most edge of the inner leg cuff to and including the distal most elastic of the inner leg cuff and extending longitudinally to the front and back waist edges of the chassis. The outer leg cuff sample is considered to be the portion of the outer leg cuff that extends from the distal most edge of the outer leg cuff to and including the proximal most elastic of the outer leg cuff and extending longitudinally to the front and back waist edges of the chassis.

For all specimen strips calculate a Span Corrected Width (SCW) is calculated as:

$$\text{Span Corrected Width} = d\left(\frac{n}{n-1}\right)$$

where d is the distance (mm) between the two distal strands, and n is the number of strands, when n>1. Clamp the strip at each end and measure the length between the clamps to the nearest 1 mm. Apply a weight equal to 3 g/mm SCW. After 10 seconds measure the final weight to the nearest 1 mm. Calculate the elongation as (Final Length−Initial Length)/Initial length.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

$$\text{Average-Strand-Spacing} = d/(n-1) \text{ where } n>1$$

report to the nearest 0.1 mm.

Pressure-Under-Strand (Also Referred to as Average Pressure-Under-Strand)

Pressure-Under-Strand is defined as the average pressure imparted by each individual elastic strand of a section under specific conditions. These conditions are defined as (refer to FIG. 92):

The section is pulled to a Stress of 7 gf/mm (within a consumer preferred range of stresses as determined experimentally)
The section is pulled over a cylinder whose circumference is defined as a Representative-Circumference
Where:

Pressure-Under-Strand (psi)=1.422*Strand-Force/ (2*Representative-Radius*Average-Strand-Diameter)

Representative-Radius (mm)=Representative-Circumference/(2*pi)

Representative-Circumference (mm)=460 mm

Stress (gf/mm)=(Summation of Strand-Forces within a section)/(Section-Width)

Section-Width (mm)=(Number of Elastics in the section)*Average-Strand-Spacing (mm)

Strand-Force (gf)=Strand-Strain (%)*0.046875*Average-Dtex

Strand-Strain (%)=strain in each elastic strand within a section

Average-Strand-Diameter (mm)=2*sqrt(Strand-Cross-Sectional-Area/pi)

Strand-Cross-Sectional-Area (mm$^2$)=Average-Dtex/ Strand-Density/10,000

Strand-Density (g/cc)=1.15 g/cc (industry standard for PolyUrethaneUrea based spandex elastics)
Dtex (g/10,000 m)=Standard textile unit of measure. Dtex is weight in grams for 10,000 m of the material
Average-Pre-Strain=Amount of stretch in elastic strands in a section prior to combining with substrate layer(s).
Maximum-Strain=Average-Pre-Strain. This is the maximum amount of strain each section can be pulled to. It cannot exceed the Average-Pre-Strain.
Maximum-Section-Force=Summation of each strand in the section pulled to the Maximum-Strain.
Section-Modulus Section-Modulus is defined as the modulus of a given section. Section-Modulus (also referred to as modulus) is the linear slope of the stress vs strain data of the section between 3 gf/mm and 7 gf/mm (refer to FIG. 93). Section-Modulus is calculated as:

Section-Modulus=[7 gf/mm−3 gf/mm]/[(section strain at 7 gf/mm)−(section strain at 3 gf/mm)]

Where:

section strain at 7 gf/mm=7 gf/mm*(Average-Strand-Spacing)/DTEX-FACTOR section strain at 3 gf/mm=3 gf/mm*(Average-Strand-Spacing)/DTEX-FACTOR Average-Strand-Spacing (mm)=d/(n−1)

d is the distance (mm) between the two distal strands of the section
n is the number of strands, when n>1

DTEX-FACTOR=37.5*Average-Dtex/800 (dtex as measured, specified)  (5)

Section-Modulus is reported in units of (gf/mm)

Average Decitex (Average-Dtex)

The Average Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastic laminates containing elastic fibers is often reported by manufacturers as part of a specification for an elastic fiber or an elastic laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g. Quick-Freeze, Miller-Stephenson Company, Danbury, Conn.), or with an appropriate solvent that will remove adhesive but not swell, alter, or destroy elastic fibers. The length of each elastic fiber in its relaxed state is measured and recorded in millimeters (mm) to the nearest mm.

Calculation of Average-Dtex

For each of the individual elastic fibers $f_i$ of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-}Dtex = \frac{\sum_{i=1}^{n}(L_i \times d_i)}{\sum_{i=1}^{n} L_i}$$

where n is the total number of elastic fibers present in an absorbent article or specimen extracted from an absorbent article. The Average-Dtex is reported to the nearest integer value of decitex (grams per 10 000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm. Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross sections exposed are mounted on an SEM sample holder in a relaxed state, sputter coated with gold, introduced into an SEM for analysis, and imaged at a resolution sufficient to clearly elucidate fiber cross sections. Fiber cross sections are oriented as perpendicular as possible to the detector to minimize any oblique distortion in the measured cross sections. Fiber cross sections may vary in shape, and some fibers may consist of a plurality of individual filaments. Regardless, the area of each of the three fiber cross sections is determined (for example, using diameters for round fibers, major and minor axes for elliptical fibers, and image analysis for more complicated shapes), and the average of the three areas $a_k$ for the elastic fiber, in units of micrometers squared ($\mu m^2$), is recorded to the nearest 0.1 $\mu m^2$. The decitex $d_k$ of the kth elastic fiber measured is calculated by:

$$d_k = 10\ 000\ m \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter (g/cm$^3$). For any elastic fiber analyzed, the experimentally determined $L_k$ and $d_k$ values are subsequently used in the expression above for Average-Dtex.

Surface Topography (Percent Contact Area, Rugosity Frequency, Rugosity Wavelength and 2-98% Height Value)

In the Surface Topography Method, an elastic laminate specimen is removed from an absorbent article and extended across and in contact with the convex surface of a transparent horizontal cylindrical tubing segment, allowing the areal surface topology of the body facing side of the laminate to be measured through the transparent tubing segment using optical profilometry. The 3D surface data are then sampled and processed to extract several parameters that describe the percent contact area and height of the elastic laminate specimen surface as well as the frequency and wavelength of its associated rugosities. All sample preparation and testing is performed in a conditioned room maintained at about 23±2° C. and about 50±2% relative humidity, and samples are equilibrated in this environment for at least 24 hours prior to testing.

Sample Preparation

SPECIMEN PREP DESCRIPTION

Each elastic laminate specimen extracted from an article is mounted on a horizontal tubing segment as described below. The tubing segment is cut from a sufficient length of optically clear, colorless cast acrylic cylindrical tubing having an outer diameter of 8.0 inches (203 mm) and a wall thickness of 0.1875 inches (4.76 mm). The segment has a dimension of 4.0 inches (102 mm) along an axis parallel to the central cylindrical axis of the parent tubing and a circumferential outer arc length of 5.5 inches (140 mm).

The elastic laminate specimen is extended in its primary stretch direction to a ratio corresponding to its extension at 3 g/mm (mass per linear width), where its width is determined by the Span Corrected Width metric as defined in the Caliper Test Method, and in which the extension is the average ratio measured under static load for the first ten seconds during which it is applied. In this extended state, the extended elastic laminate specimen is oriented such that its body-facing surface is in contact with the convex surface of the tubing segment and that the axis of extension is oriented around the circumference of the tubing segment. The extended laminate is secured at both ends to the transparent tubing segment such that the body-facing surface of the laminate is viewable through the concave side of the transparent tubing segment.

Five replicate elastic laminate specimens are isolated and prepared in this way from five equivalent absorbent articles for analysis.

3D Surface Image Acquisition

A three-dimensional (3D) surface topography image of the body facing surface of the extended elastic laminate specimen is obtained using a DLP-based, structured-light 3D surface topography measurement system (a suitable surface topography measurement system is the MikroCAD Premium instrument commercially available from LMI Technologies Inc., Vancouver, Canada, or equivalent). The system includes the following main components: a) a Digital Light Processing (DLP) projector with direct digital controlled micro-mirrors; b) a CCD camera with at least a 1600×1200 pixel resolution; c) projection optics adapted to a measuring area of at least 60 mm×45 mm; d) recording optics adapted to a measuring area of 60 mm×45 mm; e) a table tripod based on a small hard stone plate; f) a blue LED light source; g) a measuring, control, and evaluation computer running surface texture analysis software (a suitable software is MikroCAD software with Mountains Map technology, or equivalent); and h) calibration plates for lateral (XY) and vertical (Z) calibration available from the vendor.

The optical 3D surface topography measurement system measures the surface height of a sample using the digital micro-mirror pattern fringe projection technique. The nature of this pattern projection technique allows the surface topography of a specimen to be interrogated through a transparent material. The result of the measurement is a 3D data set of surface height (defined as the Z-axis) versus displacement in the horizontal (X-Y) plane. This 3D data set can also be thought of as an image in which every pixel in the image there is associated an X-Y displacement, and the value of the pixel is the recorded Z-axis height value. The system has a field of view of 60×45 mm with an X-Y pixel resolution of approximately 37 microns, and a height resolution of 0.5 microns, with a total possible height range of 32 mm.

The instrument is calibrated according to manufacturer's specifications using the calibration plates for lateral (X-Y plane) and vertical (Z-axis) available from the vendor.

The elastic laminate specimen mounted on the transparent tubing segment is positioned with the concave surface of the tubing segment surface facing upward so that the body facing surface is facing upward and visible through the transparent material. The tubing segment is placed on a stand such that the convex (downward-facing) specimen surface in the region to be analyzed is suspended freely and not resting on a surface. The tubing segment is oriented such that its circumferential direction (that direction or axis along which the laminate is stretched) is centered and perpendicular relative to the long axis of the camera's field of view (or either of the central axes if the field of view is square). A 3D surface topology image of the elastic laminate specimen is collected by following the instrument manufacturer's recommended measurement procedures, which may include focusing the measurement system and performing a brightness adjustment. No pre-filtering options are used. The collected height image file is saved to the evaluation computer running the surface texture analysis software.

If the field of view of the 3D surface topography measurement system exceeds the evaluation region on the elastic laminate specimen the image may be cropped to remove extraneous areas and retain a rectangular field of view of the relevant portion, while maintaining the X-Y resolution, prior to performing the analysis.

3D Surface Image Analysis

The 3D surface topography image is opened in the surface texture analysis software. The following filtering procedure is then performed on each image: 1) removal of invalid or non-measured points; 2) a 5×5 pixel median filter to remove noise; 3) a 5×5 pixel mean filter to smooth the surface; and 4) subtraction of a two-dimensional, second-order polynomial (determined via least-squares fit of the surface topology image) to remove the general form and flatten the surface. The second-order polynomial is defined by the following equation:

$$f(x,y)=c_1+c_2x+c_3y+c_4x^2+c_5y^2+c_6xy$$

Each data set that has been processed to this point as described above is referred to as a "preprocessed specimen data set." The highest points of the resulting topology image correspond to those areas in contact with the convex surface of the tubing segment, and the lowest points are those points most distal below the convex surface of the tubing segment.

Contact Surface Areas and 2-98% Height

For each of the 3D surface topography images of the five replicate specimens, the following analysis is performed on preprocessed specimen data sets. The Percent Surface Contact Area and 2-98% Height measurements are derived from the Areal Material Ratio (Abbott-Firestone) curve described in the ISO 13565-2:1996 standard extrapolated to surfaces. This curve is the cumulative curve of the surface height distribution histogram versus the range of surface heights measured. A material ratio is the ratio, expressed as a percent, of the area corresponding to points with heights equal to or above an intersecting plane passing through the surface at a given height, or cut depth, to the cross-sectional area of the evaluation region (field of view area). The height at a material ratio of 2% is initially identified. A cut depth of 100 μm below this height is then identified, and the material ratio at this depth is recorded as the Percent Surface Contact Area at 100 μm. This procedure is repeated at a cut depth of 200 μm and 300 μm below the identified height at a material ratio of 2%, and the material ratio at these depths are recorded as the Percent Surface Contact Area at 200 μm and the Percent Surface Contact Area at 300 μm respectively. All of the Percent Contact Area values are recorded to the nearest 0.1%.

The 2-98% Height of the specimen surface is defined as the difference in heights between two material ratios that exclude a small percentage of the highest peaks and lowest valleys. The 2-98% Height of the specimen surface is the height between the two cutting depths corresponding to a material ratio value of 2% to the material ratio of 98%, and is recorded to the nearest 0.01 mm.

Rugosity Frequency and Rugosity Wavelength

The preprocessed 3D surface topology images for each specimen are subjected to Fourier transform spatial frequency analysis to determine Rugosity Frequency and Rugosity Wavelength.

Each 3D surface topology image is deconstructed into individual line profiles by isolating each entire row of single data points that run in the dimension parallel to the elastic strands (if present and evident) of the elastic laminate, or, more generally, perpendicular to the rugosity exhibited by the elastic laminate in the relaxed state. These line profiles are therefore data sets in the form of height (in millimeters) versus distance (in millimeters).

For each replicate 3D surface topology image deconstructed, each line profile is mean centered, and a fast Fourier transform (FFT) is applied to calculate the frequency amplitude spectrum of each line profile. The Fourier transform amplitude versus spatial frequency spectra of all extracted line profiles are averaged, and the resulting average amplitude versus spatial frequency spectrum is defined as $F(1/d)$, where $1/d$ is reciprocal distance in units of $mm^{-1}$. Finally, the function $P(1/d)=d\times F^2(1/d)$, the spatial frequency power spectral density with a prefactor of distance d to correct for the expected $1/d$ noise, is plotted versus $1/d$. The value of reciprocal distance $1/d$ at which $P(1/d)$ is at a maximum is defined as the Rugosity Frequency and is recorded in units of $mm^{-1}$ to the nearest $0.001\ mm^{-1}$. The reciprocal of the Rugosity Frequency is defined as the Rugosity Wavelength and is recorded in units of mm to the nearest 0.01 mm.

Reporting of Method Parameters

After the 3D surface image analysis described above is performed on 3D surface topology images of all five specimen replicates, the following output parameters are defined and reported. The arithmetic mean of all five Percent Surface Contact Area at 100 µm measurements is defined as the Average Percent Surface Contact Area at 100 µm and is reported to the nearest 0.1%. The arithmetic mean of all five Percent Surface Contact Area at 200 µm measurements is defined as the Average Percent Surface Contact Area at 200 µm and is reported to the nearest 0.1%. The arithmetic mean of all five Percent Surface Contact Area at 300 µm measurements is defined as the Average Percent Surface Contact Area at 300 µm and is reported to the nearest 0.1%. The arithmetic mean of all five 2-98% Height measurements is defined as the Average 2-98% Height and is reported in units of mm to the nearest 0.01 mm. The arithmetic mean of all five Rugosity Frequency measurements is defined as the Average Rugosity Frequency and is reported in units of mm to the nearest $0.001\ mm^{-1}$. The arithmetic mean of all five Rugosity Wavelength measurements is defined as the Average Rugosity Wavelength and is reported in units of mm to the nearest 0.01 mm.

Open Area

Open Area is defined as the percentage of a Section not occluded by elastic strands. Un-apertured films have an Open Area 0%. Apertured film Open Area=(area occupied by apertures)/(total film area). None of today's marketed disposable absorbent articles comprising a film in one or more of a belt, sided panel, or ear panel, waistband, cuff, wing are believed to have and Open Area above 50%.

Open Area is defined as:

Open Area (%)=(Average-Strand-Diameter)/Average-Strand-Spacing

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2° C. and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Force Relaxation Over Time

The Force Relaxation over Time of a specimen is measured on a constant rate of extension tensile tester (a suitable instrument is the MTS Insight using Testworks 4.0 Software, as available from MTS Systems Corp., Eden Prairie, Minn.) using a load cell for which the forces measured are within 1% to 90% of the limit of the cell. Articles are conditioned at 23° C.±2° C. and 50%±2% relative humidity for 2 hours prior to analysis and then tested under the same environmental conditions. Prepare a sample size such that it enables a gauge length of 25.4 mm (parallel to the elastic stretch) at a width of 12.7 mm.

Program the tensile tester to perform an elongation to determine the engineering strain at which the tensile force reaches 0.0294 N/mm.

Prepare and condition a second sample as described above for the Force Relaxation over time test. The test is performed on the same equipment as described above. It is performed at a temperature of 37.8° C. Extend the sample to the strain as determined above. Hold the sample for 10 hours and record the force at a rate of 100 Hz throughout the experiment a chart showing the data for an extruded strand prior art product and an inventive elastomeric laminate comprising beam elastic as described herein is show in FIG. 104.

In view of the description above, the following non-limiting examples of combinations of features are contemplated herein:

1. A disposable absorbent article in the form of a diaper or absorbent pant, comprising a central chassis structure having a longitudinal axis, front and rear end edges and left and right side edges, and comprising:
   a liquid permeable topsheet (124), a liquid impermeable backsheet (125) and an absorbent core (128) disposed between the topsheet and the backsheet;
   left and right longitudinal barrier cuffs (150) disposed respectively proximate the left and right side edges, each barrier cuff having a base portion (152) joining one or both of the topsheet and backsheet, a longitudinally-oriented, barrier cuff free edge (153), and a longitudinally elasticized band portion (156) proximate the barrier cuff free edge, the elasticized band portion comprising:
      a first plurality of laterally-spaced elastic strands (154), the strands having an Average Decitex no greater than 300 decitex, more preferably no greater than 200 decitex, even more preferably no greater than 150 decitex, and most preferably no greater than 100 decitex, with lateral Average-Strand-Spacing no greater than 3.0 mm, more preferably no greater than 2.0 mm, and even more preferably no greater than 1.0 mm, and most preferably no greater than 0.8 mm;
      the first plurality of elastic strands being joined with at least a first layer (157) of nonwoven web material;
      the first plurality of elastic strands having an Average-Pre-Strain no greater than 250 percent, more preferably no greater than 200 percent, even more preferably no greater than 150 percent, and most preferably no greater than 100 percent.

2. A disposable absorbent article in the form of a diaper or absorbent pant, comprising a central chassis structure having a longitudinal axis, front and rear end edges and left and right side edges, and comprising:
   a liquid permeable topsheet (124), a liquid impermeable backsheet (125) and an absorbent core (128) disposed between the topsheet and the backsheet;
   left and right longitudinal barrier cuffs (150) disposed respectively proximate the left and right side edges, each barrier cuff having a base portion (152) joining one or both of the topsheet and backsheet, a longitudinally-oriented, barrier cuff free edge (153), and a longitudinally elasticized first band portion (156) proximate the barrier cuff free edge, the elasticized first band portion comprising:
      a first plurality of laterally-spaced beamed elastic strands (154), the stands having a Manufacturing Decitex no greater than 300 decitex, more preferably no greater than 200 decitex, even more preferably no greater than 150 decitex, and most preferably no greater than 100 decitex, and a Manufacturing Strand Spacing no greater than 3.0 mm, more preferably no greater than 2.0 mm, and even more preferably no greater than 1.0 mm, and most preferably no greater than 0.8 mm;
      the first plurality of elastic strands being joined with at least a first layer (157) of nonwoven web material;
      the first plurality of elastic strands having been joined with the first layer of nonwoven web material under a Manufacturing Pre-Strain no greater than 250 percent, more preferably no greater than 200 percent, even more preferably no greater than 150 percent, and most preferably no greater than 100 percent.

3. The article of either of the preceding examples wherein the first plurality of elastic strands is disposed between the first layer of nonwoven web material and a second layer (158) of nonwoven web material.

4. The article of example 3 wherein the second layer is a folded-over portion of the first layer of nonwoven web material.

5. The article of any of the preceding examples wherein the pre-strain level of the strands is substantially uniform across a width of the elasticized first band portion.

6. The article of any of the preceding examples wherein the elasticized first band portion (156) has a width of 5 mm to 30 mm, more preferably 10 mm to 25 mm, and even more preferably 15 mm to 20 mm.

7. The article of any of examples 3-6 wherein the first and second layers of nonwoven material are adhered together by adhesive.

8. The article of example 7 wherein some or all of the elastic strands are held in position laterally by adhesive.

9. The article of any of any the preceding examples wherein the first and second layers of nonwoven material are adhered together by mechanical bonds.

10. The article of any of the preceding examples wherein one or both of the first and second layers of nonwoven material comprise meltblown fibers or nanofibers.

11. The article of any of the preceding examples, further comprising:
    left and right outer leg cuffs disposed respectively proximate the left and right side edges, each leg cuff having a proximal portion joining one or both of the topsheet and backsheet, a longitudinally-oriented, free distal edge, and a longitudinally elasticized second band portion proximate the free distal edge, the elasticized second band portion comprising:
       a second plurality of laterally-spaced elastic strands, the strands having an Average Decitex no greater than 300 decitex, more preferably no greater than 200 decitex, even more preferably no greater than 150 decitex, and most preferably no greater than 100 decitex, with lateral Average Spacing no greater than 3.0 mm, more preferably no greater than 2.0 mm, and even more preferably no greater than 1.0 mm, and even more preferably no greater than 1.0 mm, and most preferably no greater than 0.8 mm;
       the second plurality of elastic strands having an Average-Pre-Strain no greater than 250 percent, more preferably no greater than 200 percent, even more preferably no greater than 150 percent, and most preferably no greater than 100 percent.
       the second plurality of elastic strands being disposed between first and second layers of web material forming at least a portion of the leg cuff.

12. The article of any of examples 1-10, further comprising:
    left and right outer leg cuffs disposed respectively proximate the left and right side edges, each leg cuff having a proximal portion joining one or both of the topsheet and backsheet, a longitudinally-oriented, free distal edge, and a longitudinally elasticized second band portion proximate the free distal edge, the elasticized second band portion comprising:
       a second plurality of laterally-spaced elastic strands, the strands having a Manufacturing Decitex no greater than 300 decitex, more preferably no greater than 200 decitex, even more preferably no greater than 150 decitex, and most preferably no greater than 100 decitex, a Manufacturing Strand Spacing no greater than 3.0 mm, more preferably no greater than 2.0 mm, and even more preferably no greater than 1.0 mm, and even more preferably no greater than 1.0 mm, and most preferably no greater than 0.8 mm;

the second plurality of elastic strands having been joined with first and second layers of web material forming at least a portion of the leg cuff, under Manufacturing Pre-Strain no greater than 250 percent, more preferably no greater than 200 percent, even more preferably no greater than 150 percent, and most preferably no greater than 100 percent.

13. A disposable absorbent article in the form of a diaper or absorbent pant, comprising a central chassis structure having a longitudinal axis, front and rear end edges and left and right side edges, and comprising:

a liquid permeable topsheet, a liquid impermeable backsheet and an absorbent core structure disposed between the topsheet and the backsheet;

left and right outer leg cuffs disposed respectively proximate the left and right side edges, each leg cuff having a proximal portion joining one or both of the topsheet and backsheet, a longitudinally-oriented, free distal edge, and a longitudinally elasticized band portion proximate the free distal edge, the elasticized band portion comprising:

a plurality of laterally-spaced elastic strands, the strands having an Average Decitex no greater than 300 decitex, more preferably no greater than 200 decitex, even more preferably no greater than 150 decitex, and most preferably no greater than 100 decitex, with lateral Average Spacing no greater than 3.0 mm, more preferably no greater than 2.0 mm, and even more preferably no greater than 1.0 mm, and even more preferably no greater than 1.0 mm, and most preferably no greater than 0.8 mm;

the plurality of elastic strands having an Average-Pre-Strain no greater than 250 percent, more preferably no greater than 200 percent, even more preferably no greater than 150 percent, and most preferably no greater than 100 percent.

the plurality of elastic strands being disposed between first and second layers of web material forming at least a portion of the leg cuff.

14. A disposable absorbent article in the form of a diaper or absorbent pant, comprising a central chassis structure having a longitudinal axis, front and rear end edges and left and right side edges, and comprising:

a liquid permeable topsheet, a liquid impermeable backsheet and an absorbent core structure disposed between the topsheet and the backsheet;

left and right outer leg cuffs disposed respectively proximate the left and right side edges, each leg cuff having a proximal portion joining one or both of the topsheet and backsheet, a longitudinally-oriented, free distal edge, and a longitudinally elasticized band portion proximate the free distal edge, the elasticized band portion comprising:

a plurality of laterally-spaced elastic strands, the strands having a Manufacturing Decitex no greater than 300 decitex, more preferably no greater than 200 decitex, even more preferably no greater than 150 decitex, and most preferably no greater than 100 decitex, a Manufacturing Strand Spacing no greater than 3.0 mm, more preferably no greater than 2.0 mm, and even more preferably no greater than 1.0 mm, and even more preferably no greater than 1.0 mm, and most preferably no greater than 0.8 mm;

the plurality of elastic strands having been joined with first and second layers of web material forming at least a portion of the leg cuff, under a Manufacturing Pre-Strain no greater than 250 percent, more preferably no greater than 200 percent, even more preferably no greater than 150 percent, and most preferably no greater than 100 percent.

15. The article of either of examples 11 or 12 wherein the barrier cuff and leg cuff are formed as a unitary combination cuff structure.

16. The article of any of examples 11-15 wherein the leg cuff free distal edge is disposed laterally outboard of a side edge of one or both of the topsheet and backsheet.

17. The article of any of the preceding examples wherein all of at least one of the pluralities of elastic strands, or all of a sub-plurality thereof, have been unwound simultaneously from a warp beam (314).

18. A method for manufacturing the disposable absorbent article of any of the preceding examples, comprising the step of unwinding all of at least one of the pluralities of elastic strands, or all of a sub-plurality thereof, simultaneously from a single warp beam (314), and incorporating them into a stretch laminate.

CONCLUSION

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments contemplated have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article in the form of a diaper or absorbent pant, comprising a central chassis structure having a longitudinal axis, front and rear end edges and left and right side edges, and comprising:

a liquid permeable topsheet, a liquid impermeable backsheet and an absorbent core disposed between the topsheet and the backsheet;

left and right longitudinal barrier cuffs disposed respectively proximate the left and right side edges, each barrier cuff having a base portion joining to one or both of the topsheet and backsheet, a longitudinally-oriented, barrier cuff free edge, and a longitudinally elasticized band portion proximate the barrier cuff free edge, the elasticized band portion comprising:
a first plurality of at least 25 laterally-spaced elastic strands, the strands having an Average Decitex no greater than 300 decitex, with lateral Average-Strand-Spacing no greater than 3.0 mm;
the first plurality of elastic strands being joined with at least a first layer of nonwoven web material;
the first plurality of elastic strands having an Average-Pre-Strain no greater than 250 percent; and
wherein the first plurality of elastic strands is disposed between the first layer of nonwoven web material and a second layer of nonwoven web material and wherein the first and second layers of nonwoven web material are adhered together by adhesive.

2. The article of claim 1 wherein the second layer is a folded-over portion of the first layer of nonwoven web material.

3. The article of claim 1 wherein the pre-strain level of the strands is substantially uniform across a width of the elasticized first band portion.

4. The article of claim 1 wherein the elasticized first band portion has a width of 5 mm to 30 mm.

5. The article of claim 1 wherein some or all of the elastic strands are held in position laterally by adhesive.

6. The article of claim 1 wherein the first and second layers of nonwoven material are adhered together by mechanical bonds.

7. The article of claim 1 wherein the first layer of nonwoven web material comprises meltblown fibers or nanofibers.

8. The article of claim 1, wherein the first plurality of elastic strands are free from mechanical bonds.

9. A disposable absorbent article in the form of a diaper or absorbent pant, comprising a central chassis structure having a longitudinal axis, front and rear end edges and left and right side edges, and comprising:
a liquid permeable topsheet, a liquid impermeable backsheet and an absorbent core disposed between the topsheet and the backsheet;
left and right longitudinal barrier cuffs disposed respectively proximate the left and right side edges, each barrier cuff having a base portion joining to one or both of the topsheet and backsheet, a longitudinally-oriented, barrier cuff free edge, and a longitudinally elasticized first band portion proximate the barrier cuff free edge, the elasticized first band portion comprising:
a first plurality of at least 25 laterally-spaced beamed elastic strands, the stands having an Average Decitex no greater than 300 decitex, and an Average Strand Spacing no greater than 3.0 mm;
the first plurality of elastic strands being joined with at least a first layer of nonwoven web material; and
the first plurality of elastic strands having an Average Pre-Strain no greater than 250 percent; and
left and right outer leg cuffs disposed respectively proximate the left and right side edges, each leg cuff having a proximal portion joining one or both of the topsheet and backsheet, a longitudinally-oriented, free distal edge, and a longitudinally elasticized second band portion proximate the free distal edge, the elasticized second band portion comprising:
a second plurality of laterally-spaced elastic strands, the strands having an Average Decitex no greater than 300 decitex, with lateral Average Spacing no greater than 3.0 mm;
the second plurality of elastic strands having an Average-Pre-Strain no greater than 250 percent,
the second plurality of elastic strands being disposed between first and second layers of web material forming at least a portion of the leg cuff; and
wherein the first plurality of elastic strands is disposed between the first layer of nonwoven web material and a second layer of nonwoven web material and wherein the first and second layers of nonwoven web material of the first band portion are adhered together by adhesive.

10. The article of claim 9 wherein the second layer of the first band portion is a folded-over portion of the first layer of nonwoven web material.

11. The article of claim 9 wherein the pre-strain level of the strands is substantially uniform across a width of the elasticized first band portion.

12. The article of claim 9 wherein the elasticized first band portion has a width of 5 mm to 30 mm.

13. The article of claim 9 wherein some or all of the elastic strands of the first band portion are held in position laterally by adhesive.

14. The article of claim 9 wherein the first and second layers of nonwoven web material of the first band portion are adhered together by mechanical bonds.

15. The article of claim 9 wherein the first layer of nonwoven web material of the first band portion comprises meltblown fibers or nanofibers.

16. The article of claim 9, wherein the first plurality of elastic strands are free from mechanical bonds.

17. A method for manufacturing the disposable absorbent article of claim 9, comprising the step of unwinding all of the first plurality of elastic strands, or all of a sub-plurality thereof, simultaneously from a single warp beam, and incorporating them into a stretch laminate.

18. A disposable absorbent article in the form of a diaper or absorbent pant, comprising a central chassis structure having a longitudinal axis, front and rear end edges and left and right side edges, and comprising:
a liquid permeable topsheet, a liquid impermeable backsheet and an absorbent core disposed between the topsheet and the backsheet;
left and right longitudinal barrier cuffs disposed respectively proximate the left and right side edges, each barrier cuff having a base portion joining to one or both of the topsheet and backsheet, a longitudinally-oriented, barrier cuff free edge, and a longitudinally elasticized band portion proximate the barrier cuff free edge, the elasticized band portion comprising:
a first plurality of at least 25 laterally-spaced elastic strands, the strands having an Average Decitex no greater than 300 decitex, with lateral Average-Strand-Spacing no greater than 3.0 mm;
the first plurality of elastic strands being joined with at least a first layer of nonwoven web material;
the first plurality of elastic strands having an Average-Pre-Strain no greater than 250 percent; and
wherein the first plurality of elastic strands is disposed between the first layer of nonwoven web material and a second layer of nonwoven web material and wherein some or all of the elastic strands are held in position laterally by adhesive.

19. The article of claim 18 wherein the second layer is a folded-over portion of the first layer of nonwoven web material.

20. The article of claim 18 wherein the pre-strain level of the strands is substantially uniform across a width of the elasticized first band portion.

21. The article of claim 18 wherein the elasticized first band portion has a width of 5 mm to 30 mm.

22. The article of claim 18 wherein some or all of the elastic strands are held in position laterally by adhesive.

23. The article of claim 18 wherein the first and second layers of nonwoven material are adhered together by mechanical bonds.

24. The article of claim 18 wherein the first layer of nonwoven web material comprises meltblown fibers or nanofibers.

25. The article of claim 18, wherein the first plurality of elastic strands are free from mechanical bonds.

26. A disposable absorbent article in the form of a diaper or absorbent pant, comprising a central chassis structure having a longitudinal axis, front and rear end edges and left and right side edges, and comprising:
- a liquid permeable topsheet, a liquid impermeable backsheet and an absorbent core disposed between the topsheet and the backsheet;
- left and right longitudinal barrier cuffs disposed respectively proximate the left and right side edges, each barrier cuff having a base portion joining to one or both of the topsheet and backsheet, a longitudinally-oriented, barrier cuff free edge, and a longitudinally elasticized first band portion proximate the barrier cuff free edge, the elasticized first band portion comprising:
- a first plurality of at least 25 laterally-spaced beamed elastic strands, the strands having an Average Decitex no greater than 300 decitex, and an Average Strand Spacing no greater than 3.0 mm;
- the first plurality of elastic strands being joined with at least a first layer of nonwoven web material; and
- the first plurality of elastic strands having an Average Pre-Strain no greater than 250 percent; and
- left and right outer leg cuffs disposed respectively proximate the left and right side edges, each leg cuff having a proximal portion joining one or both of the topsheet and backsheet, a longitudinally-oriented, free distal edge, and a longitudinally elasticized second band portion proximate the free distal edge, the elasticized second band portion comprising:
- a second plurality of laterally-spaced elastic strands, the strands having an Average Decitex no greater than 300 decitex, with lateral Average Spacing no greater than 3.0 mm;
- the second plurality of elastic strands having an Average-Pre-Strain no greater than 250 percent,
- the second plurality of elastic strands being disposed between first and second layers of web material forming at least a portion of the leg cuff; and wherein the first plurality of elastic strands is disposed between the first layer of nonwoven web material and a second layer of nonwoven web material and wherein some or all of the elastic strands of the first band portion are held in position laterally by adhesive.

27. The article of claim 26 wherein the second layer of the first band portion is a folded-over portion of the first layer of nonwoven web material.

28. The article of claim 26 wherein the pre-strain level of the strands is substantially uniform across a width of the elasticized first band portion.

29. The article of claim 26 wherein the elasticized first band portion has a width of 5 mm to 30 mm.

30. The article of claim 26 wherein some or all of the elastic strands of the first band portion are held in position laterally by adhesive.

31. The article of claim 26 wherein the first and second layers of nonwoven web material of the first band portion are adhered together by mechanical bonds.

32. The article of claim 26 wherein the first layer of nonwoven web material of the first band portion comprises meltblown fibers or nanofibers.

33. The article of claim 26 wherein the first plurality of elastic strands are free from mechanical bonds.

* * * * *